(12) United States Patent
Amini et al.

(10) Patent No.: US 10,597,714 B2
(45) Date of Patent: Mar. 24, 2020

(54) AUTOMATED PRIMING AND LIBRARY LOADING DEVICE

(71) Applicant: Clear Labs, Inc., Menlo Park, CA (US)

(72) Inventors: Sasan Amini, Redwood City, CA (US); Ramin Khaksar, Redwood City, CA (US); Michael Taylor, Kensington, MD (US); Shadi Shokralla, Danville, CA (US); Christopher Haney, Mountain View, CA (US); Pavan Vaidyanathan, Palo Alto, CA (US); Adam Allred, Menlo Park, CA (US); David Tran, Santa Rosa, CA (US); Hossein Namazi, Menlo Park, CA (US); Julius Barsi, Menlo Park, CA (US)

(73) Assignee: Clear Labs, Inc., Menlo Park, CA (US)

( * ) Notice: Subject to any disclaimer, the term of this patent is extended or adjusted under 35 U.S.C. 154(b) by 0 days.

(21) Appl. No.: 16/262,747

(22) Filed: Jan. 30, 2019

(65) Prior Publication Data

US 2019/0203287 A1 Jul. 4, 2019

Related U.S. Application Data

(63) Continuation of application No. PCT/US2018/067750, filed on Dec. 27, 2018.
(Continued)

(51) Int. Cl.
*C12Q 1/6869* (2018.01)
*C12Q 1/6883* (2018.01)
*C12Q 1/689* (2018.01)

(52) U.S. Cl.
CPC .......... *C12Q 1/6869* (2013.01); *C12Q 1/689* (2013.01); *C12Q 1/6883* (2013.01);
(Continued)

(58) Field of Classification Search
None
See application file for complete search history.

(56) References Cited

U.S. PATENT DOCUMENTS 5,578,270 A * 11/1996 Reichler ................. B01L 3/502
422/510
8,124,355 B2 2/2012 Miller
(Continued)

FOREIGN PATENT DOCUMENTS

WO WO-2012024658 A2 2/2012
WO WO-2014039963 A1 3/2014
(Continued)

OTHER PUBLICATIONS

Greninger et al., "Rapid metagenomic identification of viral pathogens in clinical samples by real-time nanopore sequencing analysis," Genome Medicine, vol. 7, pp. 1-13 (Year: 2015).*
(Continued)

*Primary Examiner* — Young J Kim
(74) *Attorney, Agent, or Firm* — Wilson Sonsini Goodrich & Rosati

(57) ABSTRACT

Provided herein are methods and apparatus for the identification of pathogenic and non-pathogenic microorganisms in food and environmental samples. The disclosure solves existing challenges encountered in identifying food borne pathogens, including pathogens of the *Salmonella, Campylobacter, Listeria*, and *Escherichia* genera in a timely and efficient manner. The disclosure also provides methods for differentiating a transient versus a resident pathogen, correlating presence of non-pathogenic with pathogenic microorganisms, distinguishing live versus dead microorganisms by sequencing.

13 Claims, 26 Drawing Sheets

Related U.S. Application Data

(60) Provisional application No. 62/730,288, filed on Sep. 12, 2018, provisional application No. 62/646,135, filed on Mar. 21, 2018, provisional application No. 62/611,846, filed on Dec. 29, 2017.

(52) U.S. Cl.
CPC .. *C12Q 2531/113* (2013.01); *C12Q 2600/142* (2013.01); *C12Q 2600/154* (2013.01)

(56) References Cited

U.S. PATENT DOCUMENTS

| | | | |
|---|---|---|---|
| 8,840,848 B2* | 9/2014 | Kraihanzel | G01N 35/1081 422/417 |
| 9,034,597 B2 | 5/2015 | Bitinaite et al. | |
| 10,101,328 B1 | 10/2018 | Amini et al. | |
| 10,246,704 B1 | 4/2019 | Amini et al. | |
| 2012/0040343 A1 | 2/2012 | Timp et al. | |
| 2014/0161686 A1 | 6/2014 | Bort et al. | |
| 2015/0176064 A1 | 6/2015 | Fach et al. | |
| 2015/0294065 A1 | 10/2015 | Gautier et al. | |
| 2015/0322426 A1 | 11/2015 | Zografos et al. | |
| 2016/0178576 A1* | 6/2016 | Maney | G01N 33/48721 204/451 |
| 2016/0239732 A1* | 8/2016 | Amini | C12Q 1/6874 |
| 2016/0257984 A1 | 9/2016 | Hardenbol et al. | |
| 2017/0044598 A1 | 2/2017 | Armes et al. | |
| 2017/0113216 A1 | 4/2017 | Amini et al. | |

FOREIGN PATENT DOCUMENTS

| | | |
|---|---|---|
| WO | WO-2016179190 A1 | 11/2016 |
| WO | WO-2016196942 A1 | 12/2016 |
| WO | WO-2017106542 A1 | 6/2017 |
| WO | WO-2017165269 A1 | 9/2017 |

OTHER PUBLICATIONS

Biomerieux Vidas, Available at www.biomerieux-usa.com/phage, Accessed on Nov. 21, 2017.
Bio-Rad. iQ-Check® Listeria monocytogenes II PCR Detection Kit #3578124.Available at http://www.bio-rad.com/en-us/sku/3578124-iq-check-listeria-monocytogenes-ii-per-detection-kit?ID=3578124. Accessed Mar. 8, 2019.
Cardinali, et al. Next Generation Sequencing: problems and opportunities for next generation studies of microbial communities in food and food industry. Current Opinion in Food Science. 2017, 17:62-67.
Co-pending U.S. Appl. No. 15/927,958, filed Mar. 21, 2018 by Amini et al.
Co-pending U.S. Appl. No. 16/054,682, filed Aug. 3, 2018 by Amini et al.
Corvium. Improve Food Safety and Quality with Our Risk Reducing Software; Our food safety software helps you to reduce your risk and protect your brand from food recalls. Available at: https://www.corvium.com. Accessed on Mar. 8, 2019.
Crowley, et al., Evaluation of VIDAS *Salmonella* (SLM) easy *Salmonella* method for the detection of *Salmonella* in a variety of foods: collaborative study, J. AOAC Int. Nov.-Dec. 2011; 94(6):1821-34.
Enviromap. Environmental monitoring has never been easier. Available at: https://digital-solutions.merieuxnutrisciences.com/en/content/enviromap. Accessed on Mar. 8, 2019.
GB1805548.3 Combined Search and Examination Report dated Dec. 11, 2018.
Greninger, et al., Rapid metagenomic identification of viral pathogens in clinical samples by real-time nanopore sequencing analysis, Genome Medicine, (2015) 7:99, 13 pages.
Hyeon, et al., Quasimetagenomics-Based and Real-Time-Sequencing-Aided Detection and Subtyping of *Salmonella enterica* from Food Samples, Appl Environ Microbiol. Feb. 15, 2018; 84(4): e02340-17, Prepublished online Dec. 1, 2017.
Hygiena. RiboPrinter System; Microbial Identification & Characterization. 2003; Rev 01. Available at: http://www.fcbiotech.com.tw/wp-content/uploads/2017/10/%E9%A3%9F%E5%93%81%E5%BE%AE%E7%94%9F%E7%89%A92.pdf. Accessed on Mar. 8, 2019.
Jain et al., The Oxford Nanopore MinION: delivery of nanopore sequencing to the genomics community, Genome Biology, (2016) 17:239, 11 pages.
Juul, et al., What's in my pot? Real-time species identification on the MinIONTM, first posted online Nov. 6, 2015 9 pages.
Kerkhof, et al., Profiling bacterial communities by MinION sequencing of ribosomal operons, Microbiome (2017) 5:116, 11 pages.
Laszlo, et al. Detection and mapping of 5-methylcytosine and 5-hydroxymethylcytosine with nanopore MspA. Proc Natl Acad Sci U S A. Nov. 19, 2013;110(47):18904-9. doi: 10.1073/pnas.1310240110. Epub Oct. 28, 2013.
Masser et al. Targeted DNA Methylation Analysis by Next-generation Sequencing, J Vis. Exp. (96):52488 (2015).
Mitsuhashi, et al., A portable system for metagenomic analyses using nanopore-based sequencer and laptop computers can realize rapid on-site determination of bacterial compositions, biorxiv, first posted online, Jan. 20, 2017, 36 pages.
Mitsuhashi, et al., A portable system for rapid bacterial composition analysis using a nanopore-based sequencer and laptop computer, Sci Rep. Jul. 18, 2017;7(1):5657.
Nguyen, et al. Real-time demultiplexing Nanopore barcoded sequencing data with npBarcode. Bioinformatics. Dec. 15, 2017;33(24):3988-3990. doi: 10.1093/bioinformatics/btx537.
Nocker, et al. Selective detection of live bacteria combining propidium monoazide sample treatment with microarray technology. Journal of Microbiological Methods, 2009, 76(3):253-261.
PCT/US2018/067750 International Search Report and Written Opinion dated Mar. 8, 2019.
Pincus, Microbial Identification Using the Biomérieux Vitek® 2 System, Available at https://store.pda.org/tableofcontents/ermm_v2_ch01.pdf, Accessed on Nov. 21, 2017.
Quick, et al., Rapid draft sequencing and real-time nanopore sequencing in a hospital outbreak of *Salmonella*, Genome Biology, (2015) 16:114, 14 pages.
Smith, et al. Reading canonical and modified nucleotides in 16S ribosomal RNA using nanopore direct RNA sequencing. Preprint available Apr. 29, 2017 on bioRxiv at https://doi:https://doi.org/10.1101/132274; Year: 2017.
Hygiena. BAX® System X5 PCR Pathogen Detection. MPB-2002_Rev 02.
Tyler, et al. Evaluation of Oxford Nanopore's MinION Sequencing Device for Microbial Whole Genome Sequencing Applications. Sci Rep. 2018; 8: 10931. Published online Jul. 19, 2018.doi: 10.1038/s41598-018-29334-5.
UMass, Indexing and Barcoding for Illumina NextGen Sequencing, available at https://www.umassmed.edu/contentassets/5ea3699998c442bb8c9b1a3cf95dbb24/indexing-and-barcoding-for-illunnina-nextgen-sequencing.pdf, accessed Jul. 31, 2018.
U.S. Appl. No. 15/927,913 Notice of Allowance dated Aug. 10, 2018.
U.S. Appl. No. 15/928,023 Office Action dated Jul. 20, 2018.
U.S. Appl. No. 15/927,958 Office Action dated Mar. 4, 2019.
U.S. Appl. No. 15/927,958 Office Action dated Oct. 5, 2018.
U.S. Appl. No. 15/928,023 Notice of Allowance dated Dec. 18, 2018.
U.S. Appl. No. 15/928,023 Notice of Allowance dated Jan. 17, 2019.
Wescoe, et al. Nanopores discriminate among five C5-cytosine variants in DNA. J Am Chem Soc. Nov. 26, 2014;136(47):16582-7. doi: 10.1021/ja508527b. Epub Nov. 14, 2014.
Ziller et al. Targeted bisulfite sequencing of the dynamic DNA methylome, Epigenetics & Chromatin 9:55 (2016).

* cited by examiner

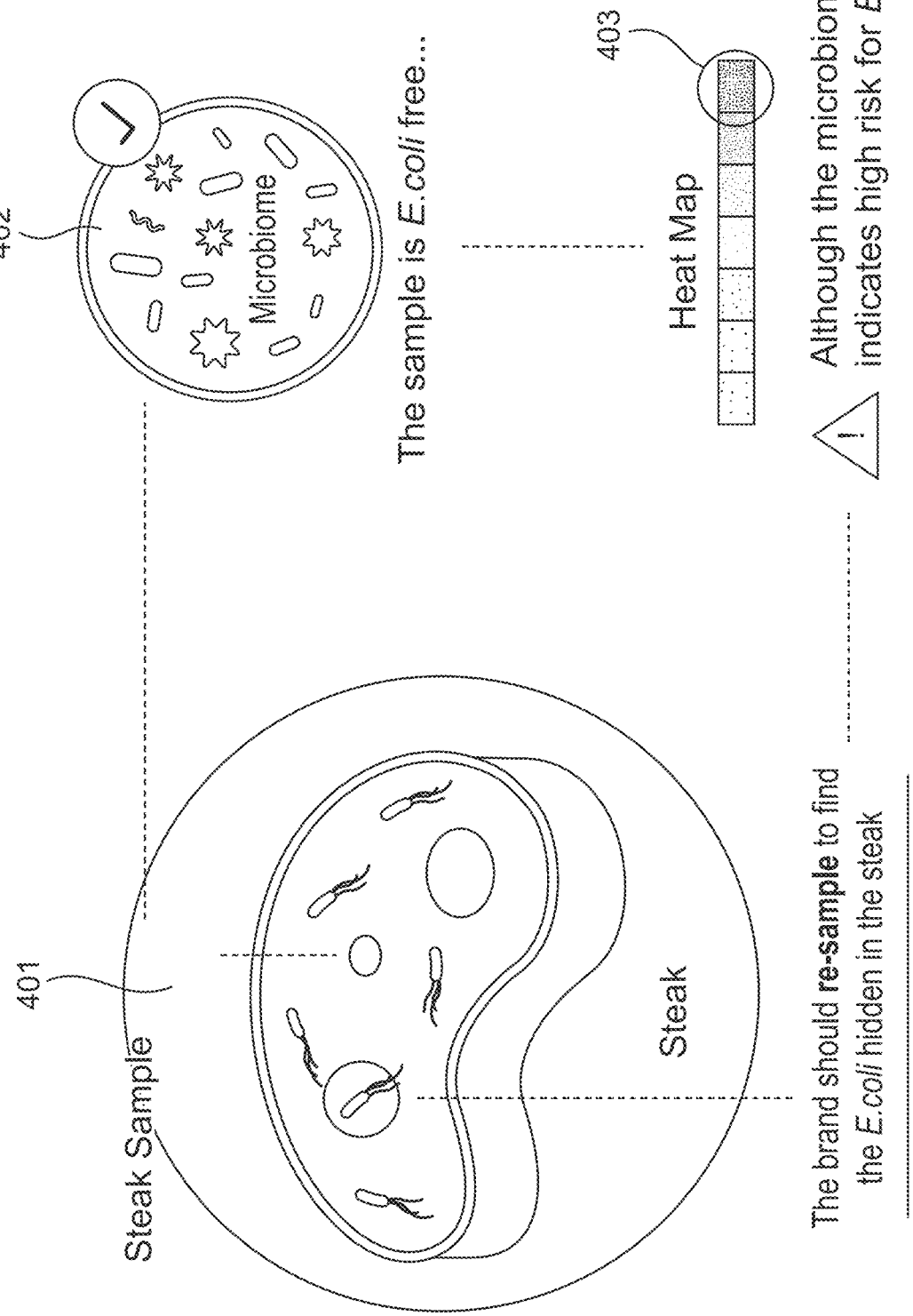

Fig. 5

Predictive Pathogen Detection Through Machine Learning

Measure Values: -0.280 to 1.000

| Pathogen\Bacteria1 | Enterobacter asburiae | Enterobacter bugandensis | Enterobacter cancerogenus | Enterobacter cloacae | Enterobacter endosymbiont | Enterobacter hormaechei | Enterobacter kobei | Enterobacter ludwigii | Enterobacter mori | Enterobacter soli |
|---|---|---|---|---|---|---|---|---|---|---|
| Vibrio parahaemolyticus | | | | | | | | | | |
| Escherichia coli | | | | | | | | | | |
| Salmonella enterica | | | ■ | ■ | | ■ | | | | |
| Shigella boydii | | | | | | | | | | |
| Campylobacter jejuni | | | | | | | | | | |
| Staphylococcus aureus | | | | | | | | | | |
| Listeria monocytogenes | | | | | | | | | | |
| Clostridium botulinum | | | | | | | | | | |
| Yersinia pseudotuberculosis | | | | | | | | ■ | | |
| Clostridium perfringens | | | | | | | | | | |
| Vibrio vulnificus | | | | | | | | | | |

Pathogens Can be Predicted from Microbiome

Model Performance

| Pathogen | Accuracy | Precision |
|---|---|---|
| Salmonella enterica | 96.16% | 94.39% |
| Escherichia coli | 97.48% | 98.40% |

Tunable Resolution

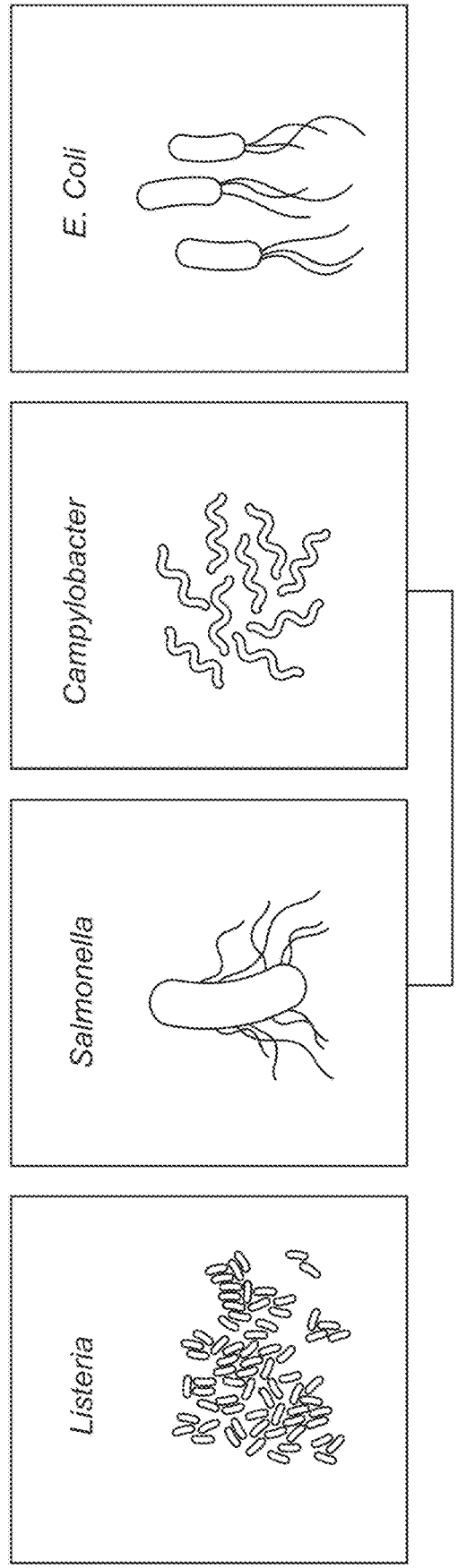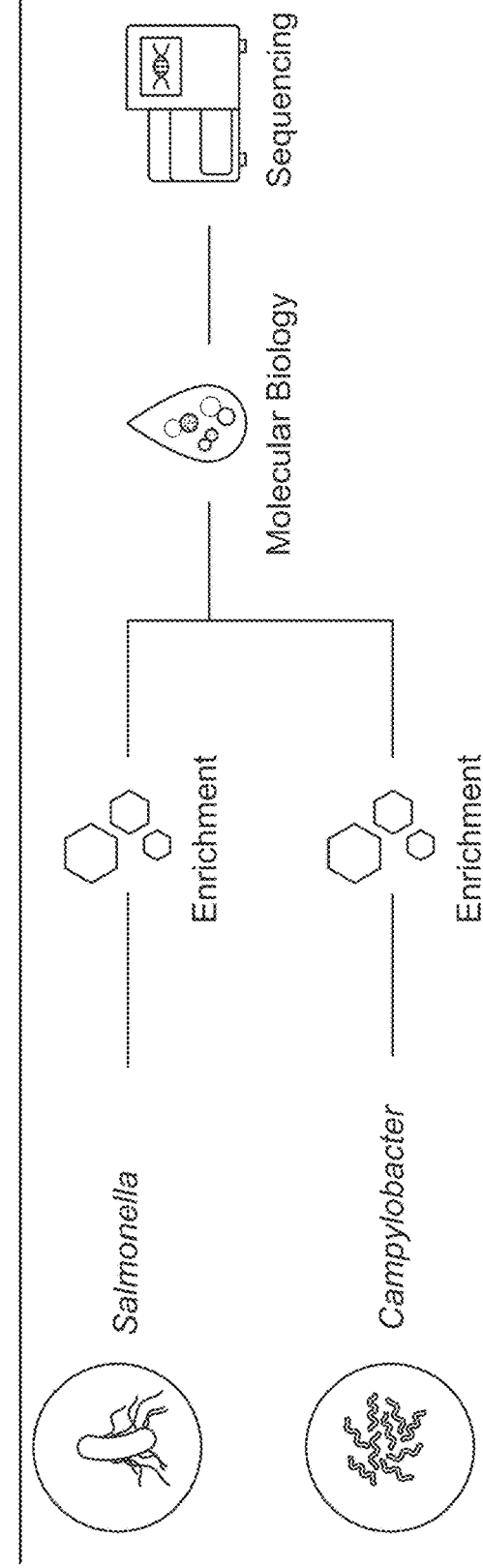
Fig. 16
Multi-Target Pathogens Same Sample

Fig. 20

|  | Manual | Automated | Manual | Automated | Manual | Automated | Manual | Automated |
|---|---|---|---|---|---|---|---|---|
| All Reads | 2196000 | 2213000 | 1945661 | 1961292 | 2342638 | 2467129 | 1267892 | 1305108 |
| Enteritidis | ✓ | ✓ | ✓ | ✓ | ✓ | ✓ | ✓ | ✓ |
| Thyphimurium | ✓ | ✓ | ✓ | ✓ | ✓ | ✓ | ✓ | ✓ |
| 14_[5]_12:i:- | ✓ | ✓ | ✓ | ✓ | ✓ | ✓ | ✓ | ✓ |
| Newport | ✓ | ✓ | ✓ | ✓ | ✓ | ✓ | ✓ | ✓ |
| Javiana | ✓ | ✓ | ✓ | ✓ | ✓ | ✓ | ✓ | ✓ |
| Infantis | ✓ | ✓ | ✓ | ✓ | ✓ | ✓ | ✓ | ✓ |
| Montevideo | ✓ | ✓ | ✓ | ✓ | ✓ | ✓ | ✓ | ✓ |
| Heidelberg | ✓ | ✓ | ✓ | ✓ | ✓ | ✓ | ✓ | ✓ |
| Muenchen | ✓ | ✓ | ✓ | ✓ | ✓ | ✓ | ✓ | ✓ |
| Saintpaul | ✓ | ✓ | ✓ | ✓ | ✓ | ✓ | ✓ | ✓ |

Fig. 23
Generating blocks with pairwise Levenshtein distance as large as possible.
Periodic Block Design: Create barcodes by repeating each block multiple times, in the example figured below 3 times.
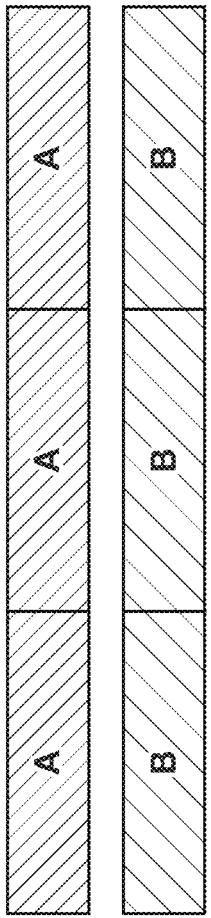
Nonperiodic Block Design: Create barcodes by concatenating multiple blocks that are unique to each barcode.

AUTOMATED PRIMING AND LIBRARY LOADING DEVICE

CROSS-REFERENCE

This application is a continuation of PCT Application No. PCT/US18/67750, filed Dec. 27, 2018; which claims priority to provisional patent application Ser. No. 62/611,846, filed on Dec. 29, 2017; provisional patent application Ser. No. 62/646,135 filed on Mar. 21, 2018; and provisional patent application Ser. No. 62/730,288, filed on Sep. 12, 2018; all of which are incorporated herein by reference in their entirety.

BACKGROUND

Food producers recall their products from the marketplace when the products are mislabeled or when the food may present a health hazard to consumers because the food is contaminated or has caused a foodborne illness outbreak. Although these producers rely on several existing monitoring programs for pathogens, natural toxins, pesticides, and other contaminants about 48 million cases of foodborne illness are still identified annually in the United States alone—the equivalent of sickening 1 in 6 Americans each year. And each year these illnesses result in an estimated 128,000 hospitalizations and 3,000 deaths. The threats are numerous and varied, with symptoms ranging from relatively mild discomfort to very serious, life-threatening illness. While the very young, the elderly, and persons with weakened immune systems are at greatest risk of serious consequences from most foodborne illnesses, some of the microorganisms detected in foods pose grave threats to all persons.

SUMMARY

In some aspects the disclosure provides a method comprising: (a) deploying an assay to one or more food processing facilities; (b) performing a sequencing reaction of a food sample or of an environmental sample from said one or more food processing facilities; (c) transmitting an electronic communication comprising a data set associated with said sequencing reaction of said food sample or of said environmental sample from said one or more food processing facilities to a server; and (d) scanning, by a computer, at least a fraction of said transmitted data set for one or more polymorphic regions associated with a microorganism.

In some aspects the disclosure provides a method comprising: (a) obtaining a plurality of nucleic acid sequences from a sample; (b) scanning, by a computer, at least a fraction of said plurality of said nucleic acid sequences for a plurality of nucleic acid regions from one or more microorganisms selected from the group consisting of: a microorganism of the *Salmonella* genus, a microorganism of the *Campylobacter* genus, a microorganism of the *Listeria* genus, and a microorganism of the *Escherichia* genus, wherein said scanning characterizes said one or more microorganisms with greater than 99.5% sensitivity.

In some aspects the disclosure provides a method comprising: (a) sequencing a plurality of nucleic acid sequences from a food sample or from an environmental sample associated with said food sample for a period of time; and (b) performing an assay on said food sample or said environment associated with said food sample if said sequencing for said period of time identifies a threshold level of nucleic acid sequences from a microorganism in said food sample.

In some aspects the disclosure provides a method comprising: (a) obtaining a first plurality of nucleic acid sequences from a first sample of a food processing facility; (b) creating a data file in a computer that associates one or more of said first plurality of nucleic acid sequences with said food processing facility; (c) obtaining a second plurality of nucleic acid sequences from a second sample of said food processing facility; and (d) scanning a plurality of sequences from said second plurality of nucleic acid sequences for one or more sequences associated with said food processing facility in (b).

In some aspects, the disclosure provides a method comprising: (a) obtaining a first sample of a food processing facility; (b) sequencing said first sample of said food processing facility, thereby generating a first set of sequencing data from said food processing facility; (c) obtaining a second sample of said food processing facility; (d) sequencing said second sample of said food processing facility, thereby generating a second set of sequencing data from said food processing facility; and (e) comparing said second set of sequencing data to said first set of sequencing data; and (d) decontaminating said food processing facility if said comparing identifies a pathogenic microorganism in said food processing facility.

In some aspects, the disclosure provides a method comprising: (a) obtaining a first plurality of nucleic acid sequences from a first sample of a food processing facility; (b) obtaining a second plurality of nucleic acid sequences from a second food sample of said food processing facility; and (c) performing sequence alignments in a computer between said first plurality of nucleic acid sequences and said second plurality of nucleic acid sequences thereby determining a similarity between said first sample and said second sample from said food processing facility.

In some aspects the disclosure provides a method comprising: (a) adding a reagent to a plurality of nucleic acid molecules from a food sample or from an environmental sample associated with said food sample, thereby forming a modified plurality of nucleic acid molecules, whereby said reagent: (i) modifies a structure of or interacts with a plurality of nucleic acid molecules derived from one or more dead microorganisms; and (ii) does not modify a structure of a nucleic acid molecule derived from one or more live microorganisms; thereby providing a modified plurality of nucleic acid molecules; and (b) sequencing by a sequencing reaction said modified plurality of nucleic acid molecules, thereby distinguishing one or more live organisms from said food sample or from said environmental sample associated with said food sample.

In some aspects the disclosure provides a method comprising performing a pore sequencing reaction on a plurality of nucleic acid molecules from a food sample or from an environmental sample associated with said food sample, whereby said pore sequencing reaction distinguishes one or more nucleic acid molecules derived from a dead microorganism from one or more nucleic acid molecules derived from a live microorganism based on a methylation pattern or another epigenetic pattern of said one or more nucleic acid molecules derived from said dead microorganism.

In some aspects the disclosure provides a method comprising: (a) obtaining a plurality of nucleic acid sequences of a food sample or of an environmental sample from a food processing facility; (b) performing a first assay in said plurality of nucleic acid sequences of said food sample, whereby said assay predicts a presence or predicts an absence of a microorganism in said food sample; and (c) determining, based on said predicted presence or said predicted absence of said microorganism of (b) whether to perform a second assay, whereby a sensitivity of said second assay is selected to determine a genus, a species, a serotype, a sub-serotype, or a strain of said microorganism.

In some aspects, the disclosure provides a method comprising: (a) detecting a presence or an absence of a non-pathogenic microorganism in a sample; (b) predicting, by a computer system, a presence or an absence of a pathogenic microorganism in said sample based on said presence or said absence of said non-pathogenic microorganism.

In some aspects, the disclosure provides a method comprising: (a) detecting a presence or an absence of a microorganism in a sample or in a facility associated with said sample; and (b) predicting, by a computer system, a risk presented by said facility based on said presence or said absence of said microorganism.

In some aspects, the disclosure provides a method comprising: (a) adding a first barcode to a first plurality of nucleic acid sequences from a sample, thereby providing a first plurality of barcoded nucleic acid sequences; and (b) performing a first sequencing reaction on said first plurality of barcoded nucleic acid sequences, wherein said sequencing reaction is performed on a sequencing apparatus comprising a flow cell; (c) adding a second barcode to a second plurality of nucleic acid sequences from a second sample, thereby providing a second plurality of barcoded nucleic acid sequences; and (d) performing a second sequencing reaction on said second plurality of barcoded nucleic acid sequences, wherein said second sequencing reaction is performed on said sequencing apparatus comprising said flow cell, thereby reusing said flow cell.

In some aspects, the disclosure provides a nucleic acid sequencing apparatus comprising: (a) a nucleic acid library preparation compartment comprising two or more chambers configured to prepare a plurality of nucleic acids from a sample for a sequencing reaction, wherein said compartment is operatively connected to a nucleic acid sequencing chamber; (b) a nucleic acid sequencing chamber, wherein said nucleic acid sequencing chamber comprises: (i) one or more flow cells comprising a plurality of pores or sequencing cartridges configured for the passage of a nucleic acid strand, wherein two or more of the one or more flow cells are juxtaposed to one another; and (c) an automated platform, wherein said automated platform is programmed to robotically move a sample from said nucleic acid library preparation compartment into said nucleic acid sequencing chamber.

In some aspects, the disclosure provides a method comprising: (a) adding a first molecular index to a first plurality of nucleic acid sequences from a sample, thereby providing a first plurality of indexed nucleic acid sequences; and (b) adding a second molecular index to said first plurality of nucleic acid sequences from said first sample, thereby providing a second plurality of indexed nucleic acid sequences; and (c) adding a third molecular index to said first plurality of nucleic acid sequences from said first sample, thereby providing a third plurality of indexed nucleic acid sequences; (d) performing a sequencing reaction on said third plurality of nucleic acid sequences; and (e) demultiplexing, by a computer system, said third plurality of nucleic acid sequences comprising said first molecular index, said second molecular index, and said third molecular index.

In some aspects, the present disclosure describes a device capable of detecting and distinguishing microorganisms, including food-borne pathogens. Food-borne pathogens may include any of the numerous organisms that spread via food consumption, including enterotoxic *E. Coli* and *Salmonella* bacteria. These microorganisms can often survive in a wide variety of environments, including food preparation surfaces and food processing equipment, as well as on food itself. Tracing the origins and movements of food-borne pathogen outbreaks often necessitates detecting one or more microorganisms from a variety of sample types, including swabs, food samples, and stool samples. Because outbreaks may be tied to a particular strain of a microorganism, e.g. *E. coli* O157:H7, and because its detection is critical to stopping its spread, detection must be rapid and accurate.

A food-borne pathogen detection system may be designed for numerous purposes, including deployable systems that can be moved to any environment, e.g. a farm field, or grounded devices for laboratory settings where collected samples are brought to the device. In most cases, it is highly desirable to have a device that is highly automated to reduce the number of steps that a user must be involved in to increase the ease of usage and reduce the risk of contamination or other sources of process failure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates a process for predictive risk assessment based on a detection of a non-pathogenic microorganism.

FIG. 5 is a heat map illustrating predictive pathogen detection through machine learning.

FIG. 16 illustrates the simultaneous targeting of multiple pathogens.

FIG. 20 illustrates the performance of the disclosed automated handling system on samples spiked with 10 different *Salmonella* serotypes (*Enteritidis, Thyphimurium, I 4_[5]_12:i:, Newport, Javiana, Infantis, Montevideo, Heidelberg, Muenchen*).

FIG. 23 illustrates periodic and nonperiodic barcode designs.

DETAILED DESCRIPTION

Figure 1:
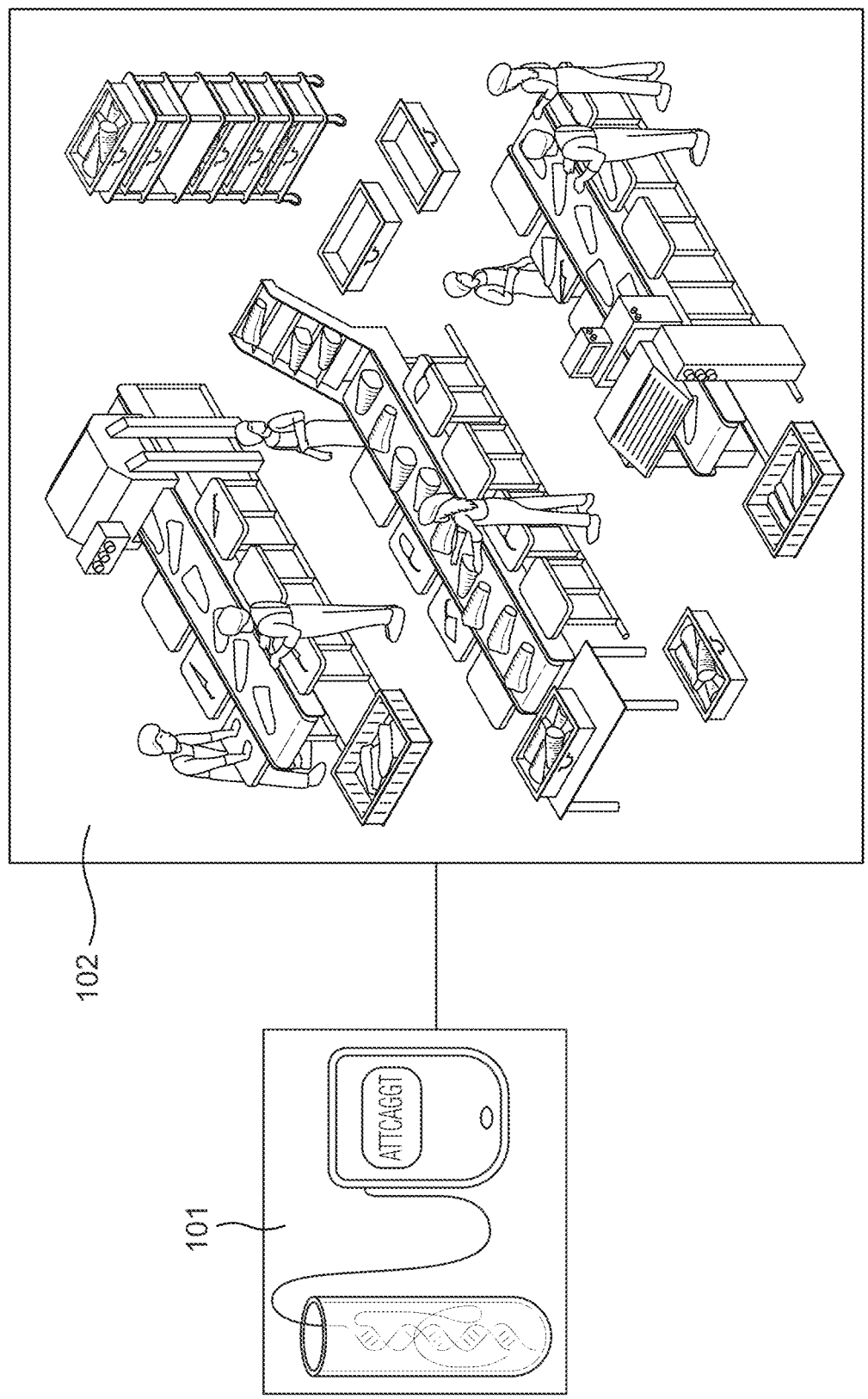
FIG. 1 illustrates the deploying of a sequencing assay 101 to one or more food processing facilities, food testing lab, or any other diagnostic lab 102 for performing a sequencing reaction of a food sample or of an environmental sample from said food processing facilities such as, for example, soil, water, air, animal product(s), feed, manure, crop production, or any sample associated with a manufacturing plant.

Food safety is a complex issue that has an impact on multiple segments of society. Usually a food is considered to be adulterated if it contains: (1) a poisonous or otherwise harmful substance that is not an inherent natural constituent of the food itself, in an amount that poses a reasonable possibility of injury to health, or (2) a substance that is an inherent natural constituent of the food itself; is not the result of environmental, agricultural, industrial, or other contamination; and is present in an amount that ordinarily renders the food injurious to health. The first includes, for example, a pathogenic bacterium, fungus, parasite or virus, if the amount present in the food may be injurious to health. An example of the second is the tetrodotoxin that occurs naturally in some organs of some types of pufferfish and that ordinarily will make the fish injurious to health. In either case, foods adulterated with these agents are generally deemed unfit for consumption.

Many different disease-causing microorganisms can contaminate foods, and there are many different foodborne infections. Although our scientific understanding of pathogenic microorganisms and their toxins is continually advancing, some of the most common microorganisms associated with foodborne illnesses include microorganisms of the *Salmonella, Campylobacter, Listeria*, and *Escherichia* genus.

*Salmonella* for example is widely dispersed in nature. It can colonize the intestinal tracts of vertebrates, including livestock, wildlife, domestic pets, and humans, and may also live in environments such as pond-water sediment. It is spread through the fecal-oral route and through contact with contaminated water. (Certain protozoa may act as a reservoir for the organism). It may, for example, contaminate poultry, red meats, farm-irrigation water (thereby contaminating produce in the field), soil and insects, factory equipment, hands, and kitchen surfaces and utensils.

*Campylobacter jejuni* is estimated to be the third leading bacterial cause of foodborne illness in the U.S. The symptoms this bacterium causes generally last from 2 to 10 days and, while the diarrhea (sometimes bloody), vomiting, and cramping are unpleasant, and they usually go away by themselves in people who are otherwise healthy. Raw poultry, unpasteurized ("raw") milk and cheeses made from it, and contaminated water (for example, unchlorinated water, such as in streams and ponds) are major sources, but *C. jejuni* also occurs in other kinds of meats and has been found in seafood and vegetables.

Although the number of people infected by foodborne *Listeria* is comparatively small, this bacterium is one of the leading causes of death from foodborne illness. It can cause two forms of disease. One can range from mild to intense symptoms of nausea, vomiting, aches, fever, and, sometimes, diarrhea, and usually goes away by itself. The other, more deadly, form occurs when the infection spreads through the bloodstream to the nervous system (including the brain), resulting in meningitis and other potentially fatal problems.

*Escherichia* microorganisms are also diverse in nature. For instance, at least four groups of pathogenic *Escherichia coli* have been identified: a) Enterotoxigenic *Escherichia coli* (ETEC), b) Enteropathogenic *Escherichia coli* (EPEC), c) Enterohemorrhagic *Escherichia coli* (EHEC), and Enteroinvasive *Escherichia coli* (EIEC). While ETEC is generally associated with traveler's diarrhea some members of the EHEC group, such as *E. coli* O157:H7, can cause bloody diarrhea, blood-clotting problems, kidney failure, and death. Thus, it is important to be able not only to identify individual microorganism, but also to distinguish them.

Provided herein are methods and apparatus for the identification of pathogenic and non-pathogenic microorganisms in food and environmental samples. The disclosure solves existing challenges encountered in identifying food borne pathogens, including pathogens of the *Salmonella, Campylobacter, Listeria*, and *Escherichia* genus in a timely and efficient manner. The disclosure also provides methods for differentiating a transient versus a resident pathogen, correlating presence of non-pathogenic with pathogenic microorganisms, and distinguishing live versus dead microorganisms by sequencing, amongst others.

As used herein, the term "food processing facility" includes facilities that manufacture, process, pack, or hold food in any location globally. A food processing facility can, for example, determine the location and source of an outbreak of food-borne illness or a potential bioterrorism incident.

As used herein, the term "food" includes any nutritious substance that people or animals eat or drink, or that plants absorb, in order to maintain life and growth. Non-limiting examples of foods include red meat, poultry, fruits, vegetables, fish, pork, seafood, dairy products, eggs, egg shells, raw agricultural commodities for use as food or components of food, canned foods, frozen foods, bakery goods, snack food, candy (including chewing gum), dietary supplements and dietary ingredients, infant formula, beverages (including alcoholic beverages and bottled water), animal feeds and pet food, and live food animals. The term "environmental sample," as used herein, includes all food contact substances or items from a food processing facility. The term environmental sample includes a surface swab of a food contact substance, a surface rinse of a food contact substance, a food storage container, a food handling equipment, a piece of clothing from a subject in contact with a food processing facility, or another suitable sample from a food processing facility. The term "sample" as used herein, generally refers to any sample that can be informative of an environment or a food, such as a sample that comprises soil, water, water quality, air, animal production, feed, manure, crop production, manufacturing plants, environmental samples or food samples directly. The term "sample" may also refer to other non-food sample, such as samples derived from a subject, such as comprise blood, plasma, urine, tissue, faces, bone marrow, saliva or cerebrospinal fluid. Such samples may be derived from a hospital or a clinic.

As used herein, the term "subject," can refer to a human or to another animal. An animal can be a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

As used herein, the term "disease," generally refers to conditions associated with the presence of a microorganism in a food, e.g., outbreaks or incidents of foodborne disease.

The term "nucleic acid" or "polynucleotide," as used herein, refers to a polymeric form of nucleotides of any length, either ribonucleotides or deoxyribonucleotides. Polynucleotides include sequences of deoxyribonucleic acid (DNA), ribonucleic acid (RNA), or DNA copies of ribonucleic acid (cDNA).

The term "polyribonucleotide," as used herein, generally refers to polynucleotide polymers that comprise ribonucleic acids. The term also refers to polynucleotide polymers that comprise chemically modified ribonucleotides. A polyribonucleotide can be formed of D-ribose sugars, which can be found in nature, and L-ribose sugars, which are not found in nature.

The term "polypeptides," as used herein, generally refers to polymer chains comprised of amino acid residue monomers which are joined together through amide bonds (peptide bonds). The amino acids may be the L-optical isomer or the D-optical isomer.

The term "barcode," as used herein, generally refers to a label, or identifier, that conveys or is capable of conveying information about one or more nucleic acid sequences from a food sample or from an environmental sample associated with said food sample. A barcode can be part of a nucleic acid sequence. A barcode can be independent of a nucleic acid sequence. A barcode can be a tag attached to a nucleic acid molecule. A barcode can have a variety of different formats. For example, barcodes can include: polynucleotide barcodes; random nucleic acid and/or amino acid sequences; and synthetic nucleic acid and/or amino acid sequences. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads. Examples of such barcodes and uses thereof, as may be used with methods, apparatus and systems of the present disclosure, are provided in U.S. Patent Pub. No. 2016/0239732, which is entirely incorporated herein by reference. In some instances, as described herein, a "molecular index" can either be a barcode itself or it can be a building block, i.e., a component or portion of a larger barcode.

The term "sequencing," as used herein, generally refers to methods and technologies for determining the sequence of nucleotide bases in one or more nucleic acid polymers, i.e., polynucleotides. Sequencing can be performed by various systems currently available, such as, without limitation, a sequencing system by Illumina®, Pacific Biosciences (PacBio®), Oxford Nanopore®, Genia (Roche) or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw data corresponding to the genetic information associated with a food sample or an environmental sample. In some examples, such systems provide nucleic acid sequences (also "reads" or "sequencing reads" herein). The term also refers to epigenetics which is the study of heritable changes in gene function that do not involve changes in the DNA sequence. A read may include a string of nucleic acid bases corresponding to a sequence of a nucleic acid molecule that has been sequenced.

Analyzing Sequences Requested by a Customer

Many food poisoning outbreaks have been associated with pathogenic microorganisms including pathogens of the *Salmonella, Campylobacter, Listeria*, and *Escherichia* genus. Examples of foods that have been associated with such outbreaks include milk, cheeses, vegetables, meats (notably beef and poultry), fish, seafood, and many others. Potential contamination sources for various pathogens include raw materials, food workers, incoming air, water, and food processing environments. Among those, post-processing contamination at food-contact surfaces in a food processing facility poses a great threat to product contamination.

There are many challenges in ensuring the safety of our food supply. Some of these challenges include changes in a food processing environment that lead to food contamination, such as the introduction of a new lot of contaminated raw products. Other challenges include changes in food production and supply, which include importing and exporting foods from different jurisdictions, which may have distinct standards to assess a risk associated with a food. In addition, new and emerging bacteria strains, toxins, and antibiotic resistance may not be detected by traditional serotyping or PCR methods of detection.

In some aspects, the disclosure provides a method for the identification of a microorganism associated with a food or with a food processing facility. In some aspects the method comprises deploying an assay to one or more food processing facilities; performing a sequencing reaction of a food sample or of an environmental sample from said one or more food processing facilities; transmitting an electronic communication comprising a data set associated with said sequencing reaction of said food sample or of said environmental sample from said one or more food processing facilities to a server; and scanning, by a computer, at least a fraction of said transmitted data set for one or more genes associated with a microorganism. In some embodiments, the method comprises deploying an assay to one or more food processing facilities; receiving via a server an electronic communication comprising a data set associated with a sequencing reaction, wherein the sequencing reaction characterizes a food sample or of an environmental sample from said one or more food processing facilities; and scanning, by a computer, at least a fraction of said transmitted data set for one or more genes associated with a microorganism.

In some aspects, the disclosure provides a method for the identification of a microorganism associated with a food or with a food processing facility. In some aspects the method comprises receiving an assay at one or more food processing facilities; performing a sequencing reaction of a food sample or of an environmental sample from said one or more food processing facilities; transmitting an electronic communication comprising a data set associated with said sequencing reaction of said food sample or of said environmental sample from said one or more food processing facilities to a server; and scanning, by a computer, at least a fraction of said transmitted data set for one or more genes associated with a microorganism. In some embodiments, the method comprises receiving an assay at one or more food processing facilities; receiving via a server an electronic communication comprising a data set associated with a sequencing reaction, wherein the sequencing reaction characterizes a food sample or of an environmental sample from said one or more food processing facilities; and scanning, by a computer, at least a fraction of said transmitted data set for one or more genes associated with a microorganism.

In some aspects, the disclosure provides a method for the identification of a microorganism associated with a food or with a food processing facility. In some aspects the method comprises deploying an assay to one or more food processing facilities; receiving an electronic communication comprising a data set associated with a sequencing reaction of a food sample or an environmental sample from said one or more food processing facilities to a server; and scanning, by a computer, at least a fraction of said transmitted data set for one or more genes associated with a microorganism. In some embodiments, the method comprises deploying an assay to one or more food processing facilities; receiving via a server an electronic communication comprising a data set associated with a sequencing reaction, wherein the sequencing reaction characterizes a food sample or of an environmental sample from said one or more food processing facilities; and scanning, by a computer, at least a fraction of said transmitted data set for one or more genes associated with a microorganism.

In some instances, the scanning scans fewer than 1%, fewer than 0.1%, fewer than 0.001% of said transmitted data set for one or more genes associated with said microorganism. Said scanning can be performed to identify a variety of polymorphic gene regions (comprising SNP's, RFLP's, STRs, VNTR's, hypervariable regions, minisatellites, dinucleotide repeats, trinucleotide repeats, tetranucleotide repeats, simple sequence repeats, indels, and insertion elements) associated with a wide diversity of microorganisms. The variety of polymorphic regions to be searched for can be determined by creating a large database of sequences from dozens, hundreds and thousands of food and environmental samples. For instance, a database of such polymorphic regions can be constructed by performing sequencing reactions on at least 5,000, at least 10,000, at least 15,000, at least 20,000, at least 25,000, at least 30,000, at least 35,000, at least 40,000, at least 45,000, at least 50,000 different food or environmental samples. The sequences obtained can be used to compile information in a database that includes: a) the composition of each sample; and b) the presence or absence of a variety of pathogenic and non-pathogenic organisms associated on each sample. In addition to containing information about various types of genus and species, such databases comprise data from polymorphic gene regions of a variety of strains that are variants of a single species. For example, a plurality of sequences in the database might correspond to one or more serovars, morphovars, biovars, or other strain specific information.

A variety of sequencing techniques, such as a pore sequencing reaction, a next generation sequencing reaction, a shotgun next generation sequencing, or Sanger sequencing can be used to create a collection of polymorphic regions. In some instances, said sequencing reaction is a pore sequencing reaction and said pore sequencing reaction distinguishes an epigenetic pattern on a nucleic acid from said food sample or from said environmental sample.

In some cases, said microorganism may be pre-selected by a customer. A customer can be an individual or an entity, such as one or more food processing facilities. For example, a customer can be a food packaging facility; a food distribution center; a food storage center; a facilities handling meat, poultry, egg, or another edible product; a farm; a retail food establishment; a fishing vessel; or another type of facility that also manufactures, processes, packs, or holds foods for any period of time.

A customer may pre-select a microorganism of interest to be identified with any of the methods disclosed herein. For example, raw or undercooked ground beef and beef products are vehicles often implicated in *E. coli* O157:H7 outbreaks. Produce, including bagged lettuce, spinach, and alfalfa sprouts, are also increasingly being implicated in *E. coli* O157:H7 outbreaks. A food processing facility producing raw meats or other produce associated with *E. coli* O157:H7 may be a customer that pre-selects *E. coli* as a microorganism for analysis. A customer may pre-select one or more types of microorganisms for analysis. A microorganism can be one or more of types of bacteria, fungus, parasites, protozoa, and viruses.

Non-limiting examples of bacteria that can be pre-selected by a customer and detected with the methods of the disclosure include: bacteria in the *Escherichia* genus, including enterotoxigenic *Escherichia coli* (ETEC), enteropathogenic *Escherichia coli* (EPEC), enterohemorrhagic *Escherichia coli* (EHEC), and enteroinvasive *Escherichia coli* (EIEC); bacteria of the *Salmonella* genus; bacteria of the *Campylobacter* genus; bacteria of the *Listeria* genus; bacteria of the *Yersinia* genus; bacteria of the *Shigella* genus; bacteria of the *Vibrio* genus; bacteria of the *Coxiella* genus; bacteria of the *Mycobacterium* genus; bacteria of the *Brucella* genus; bacteria of the *Vibrio* genus; bacteria of the *Cronobacter* genus; bacteria of the *Aeromonas* genus; bacteria of the *Plesiomonas* genus; bacteria of the *Clostridium* genus; bacteria of the *Staphylococcus* genus; bacteria of the *Bacillus* genus; bacteria of the *Streptococcus* genus; bacteria of the *Clostridium* genus; and bacteria of the *Enterococcus* genus.

A microorganism can be a virus. Non-limiting examples of viruses that can be pre-selected by a customer and detected with the methods of the disclosure include: noroviruses, Hepatitis A virus, Hepatitis E virus, rotavirus.

The performing of a sequencing reaction of a food sample or of an environmental sample from said one or more food processing facilities often generates a plurality of nucleic acids sequences that contain redundant information or information associated with genes that are not from a microorganism. In some aspects, the disclosed methods empower efficient data analysis by facilitating the targeted analysis of a smaller data set. The generated data could be in the range of Kb, Mb, Gb, Tb or more per analyzed sample. In some aspects, said scanning scans fewer than 1/10, fewer than 1/20, fewer than 1/30, fewer than 1/40, fewer than 1/50, fewer than 1/60, fewer than 1/70, fewer than 1/80, fewer than 1/90, fewer than 1/100, fewer than 1/200, fewer than 1/300, fewer than 1/400, fewer than 1/500, fewer than 1/600, fewer than 1/700, fewer than 1/800, fewer than 1/900, fewer than 1/1,000, fewer than 1/10,000, or fewer than 1/100,000 of a data set, such as a transmitted data set for one or more genes associated with a microorganism. In some aspects, said scanning scans at least a fraction of said transmitted data set for one or more genes associated with two or more, three or more, four or more, five or more, six or more, seven or more, eight or more, nine or more, ten or more microorganisms or another suitable number. In some instances, said scanning comprises scanning said transmitted data set for one or more polymorphic gene regions. In some instances, said one or more polymorphic regions comprise one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements. In some instances said one or more polymorphic regions comprise one or more single nucleotide polymorphisms (SNP's). A data set associated with a sequencing reaction of a food sample or of an environmental sample can be transmitted to a server and scanned by a computer.

In some cases, a method can detect a microorganism selected from the group consisting of: a microorganism of the *Salmonella* genus, a microorganism of the *Campylobacter* genus, a microorganism of the *Listeria* genus, and a microorganism of the *Escherichia* genus. The detected microorganisms may be of any serotype and a scanning, by a computer, of one or more genes associated with a microorganism may detect a microorganism independently of its serotype.

In some cases, a sequencing reaction of a food sample, an environmental sample, or another sample is a pore sequencing reaction, such as an Oxford Nanopore® sequencing reaction. In some instances, at least one barcode is added to one or more nucleic acid polymers derived from a food sample, from an environmental sample, or from another sample prior to performing said sequencing reaction. In some instances, a plurality of mutually exclusive barcodes are added to a plurality of food processing facilities, thereby creating a barcode identifier that can be associated with each food processing facility. For instance, a barcoded sequencing read comprising sequences from a pathogenic microorganism can be associated with a food or processing facility. In some aspects, a method disclosed herein further comprises creating, in a computer, a data file that associates said at least one barcode with a source of said food sample, of said environmental sample, or of another sample.

Figure 2:
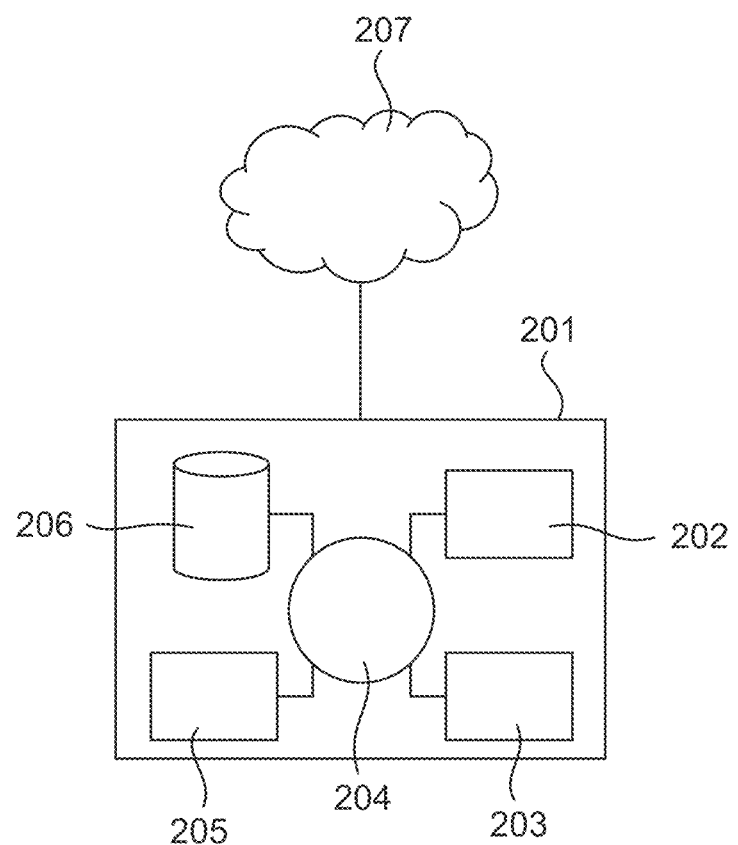
FIG. 2 illustrates a transmission of an electronic communication comprising a data set associated with a sequencing reaction from one or more food processing facilities to a server.

In some aspects, the disclosed methods comprise computer systems or devices utilizing computer systems that are programmed to implement methods of the disclosure. FIG. 1 illustrates the deploying of a sequencing assay 101 to one or more food processing facilities 102, food testing lab, or any other diagnostic lab and performing a sequencing reaction of a food sample or of an environmental sample from said one or more food processing facilities 102. The food processing facility, food testing lab, or any other diagnostic lab may have one or more computer systems that can be used to transmit the results of the sequencing reads to a server, either on premise or remotely deployed cloud environment. FIG. 2 illustrates a transmission of an electronic communication comprising a data set associated with a sequencing reaction from one or more food processing facilities, food testing labs, or any other diagnostic labs to a server.

The raw sequence data collected from the sequencing reaction includes a large set of data that includes all individual sequences as well as the quality at each base. From this large data set, the Clear Labs bioinformatics pipeline extracts a final report that is orders of magnitudes smaller. The final report (e.g. electronic communication) is essentially limited to the presence or absence of an organism of interest, for instance pathogens, and a further classification of the organism in terms of serotypes, strains, or other subclassifications. The collected data not used in the report comprises the following:

(a) Read quality: The raw sequences include information on the quality of the sequences per base. The quality scores can be used in a Bayesian model where classifications are statistically sensitive to these quality scores. Furthermore the quality scores can reveal more on possible relations that content of samples have with the accuracy of sequencing platform.

(b) Sequence time: The raw sequences also include information on the time when the sequence was read by the sequencer. The number of sequences form the same source as a function of time can reveal a lot more information than we currently have. In addition, these time data, can be useful in generating reports for all or some of the samples earlier than it is currently done.

(c) Trimmed portions of sequences: During demultiplexing of the sequences initial and terminal portions of those sequences are trimmed. Those portions include adapters, index barcodes, and primers. The main data extracted from the trimmed portions, identifies which sample the sequence belonged to. This decision however is influenced by sequencing errors, and special properties of the involved sequences. The information on accuracy of this decision, and other factors is lost with trimming. Moreover the quality of these portions can be used as an indicator for the quality of the entire sequence.

(d) Clustering: An important step in the pipeline involves clustering sequences that are close enough to each other and representing all the sequences within a cluster by a consensus sequence. This reduces the data significantly and make is easier to classify these sequences. However these differences, even if minute, carry information that gets lost with clustering. Clustering with more stringent criteria, or no clustering can lead into higher resolution and perhaps finer classification.

A computer system 201 can be programmed or otherwise configured to process and transmit a data set from a food processing facility, food testing labs, or any other diagnostic labs. The computer system 201 includes a central processing unit (CPU, also "processor" and "computer processor" herein) 204, which can be a single core or multi core processor, or a plurality of processors for parallel processing. The computer system 201 also includes memory or memory location 205 (e.g., random-access memory, read-only memory, flash memory), electronic storage unit 206 (e.g., hard disk), communication interface 202 (e.g., network adapter) for communicating with one or more other systems, such as for instance transmitting a data set associated with said sequencing reads, and peripheral devices 204, such as cache, other memory, data storage and/or electronic display adapters. The memory 205, storage unit 206, interface 202 and peripheral devices 203 are in communication with the CPU 204 through a communication bus (solid lines), such as a motherboard. The storage unit 206 can be a data storage unit (or data repository) for storing data. For instance, in some cases, the data storage unit 206 can store a plurality of sequencing reads and provide a library of sequences associated with one or more strains from one or more microorganisms associated with a food processing facility, food testing labs, or any other diagnostic labs.

The computer system 201 can be operatively coupled to a computer network ("network") 207 with the aid of the communication interface 202. The network 207 can be the Internet, an internet and/or extranet, or an intranet and/or extranet that is in communication with the Internet. The network 207 in some cases is a telecommunication and/or data network. The network 207 can include one or more computer servers, which can enable distributed computing, such as cloud computing. The network 207, in some cases with the aid of the computer system 201, can implement a peer-to-peer network, which may enable devices coupled to the computer system 201 to behave as a client or a server.

High Sensitivity Detection of Microorganisms

Some families of microorganisms comprise both harmless and highly pathogenic bugs. The *Escherichia* family of pathogens, for example, comprise lethal and harmless strains of *E. coli*. Thus it is not only relevant to be able to identify a pathogen in a sample, but it is also relevant to be able to characterize it with high sensitivity. In some aspects, the disclosure provides a method comprising obtaining a plurality of nucleic acid sequences from a food sample, from an environment associated with said food sample or from another sample, such as non-food derived samples from clinical sources, including blood, plasma, urine, tissue, faces, bone marrow, saliva or cerebrospinal fluid samples; scanning, by a computer, at least a fraction of said plurality of said nucleic acid sequences for a plurality of nucleic acid regions from one or more microorganisms selected from the group consisting of: a microorganism of the *Salmonella* genus, a microorganism of the *Campylobacter* genus, a microorganism of the *Listeria* genus, and a microorganism of the *Escherichia* genus, wherein said scanning characterizes said one or more microorganisms with greater than 98% sensitivity, greater than 98.5% sensitivity, greater than 99% sensitivity, greater than 99.5% sensitivity, or greater than 99.9% sensitivity. In some aspects, said scanning characterizes said one or more microorganisms with greater than 98% specificity, greater than 98.5% specificity, greater than 99% specificity, greater than 99.5% specificity, or greater than 99.9% specificity. Sensitivity can be a measure of a microorganism that is correctly identified (e.g. the percentage of a microorganism that can be correctly identified based on sequencing read analyses). Specificity (also called the true negative rate) measures the proportion of negatives that are correctly identified as such (e.g. the percentage of food samples or environmental samples that are correctly identified as not having the microorganism therein). In some instances, said method can distinguish a genetic variant or subtype of a microorganism (e.g., one or more bacterial strains).

In some instances said plurality of nucleic acid sequences comprise complementary DNA (cDNA) sequences, ribonucleic acid (RNA) sequences, genomic deoxyribonucleic acid (gDNA) sequences or a mixture of cDNA, RNA, and gDNA sequences. In some instances, the high sensitivity of the disclosed method, the high specificity of the disclosed method, or both, can be accomplished by scanning said plurality of said nucleic acid sequences for one or more polymorphic gene regions associated with said microorganisms. In some instances, said one or more polymorphic regions is selected from the group consisting of one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements. In some instances, said scanning compares a scanned polymorphism with a library of sequences comprising sequences from dozens, hundreds, or thousands of unique strains of a microorganism. The higher sensitivity is achieved by comparing the sequence information of the target region that can discriminate different microorganisms through the lens of SNPs, indels or other non-universal target specific markers that are only present within the genome of target micromicroorganisms.

Figure 3:
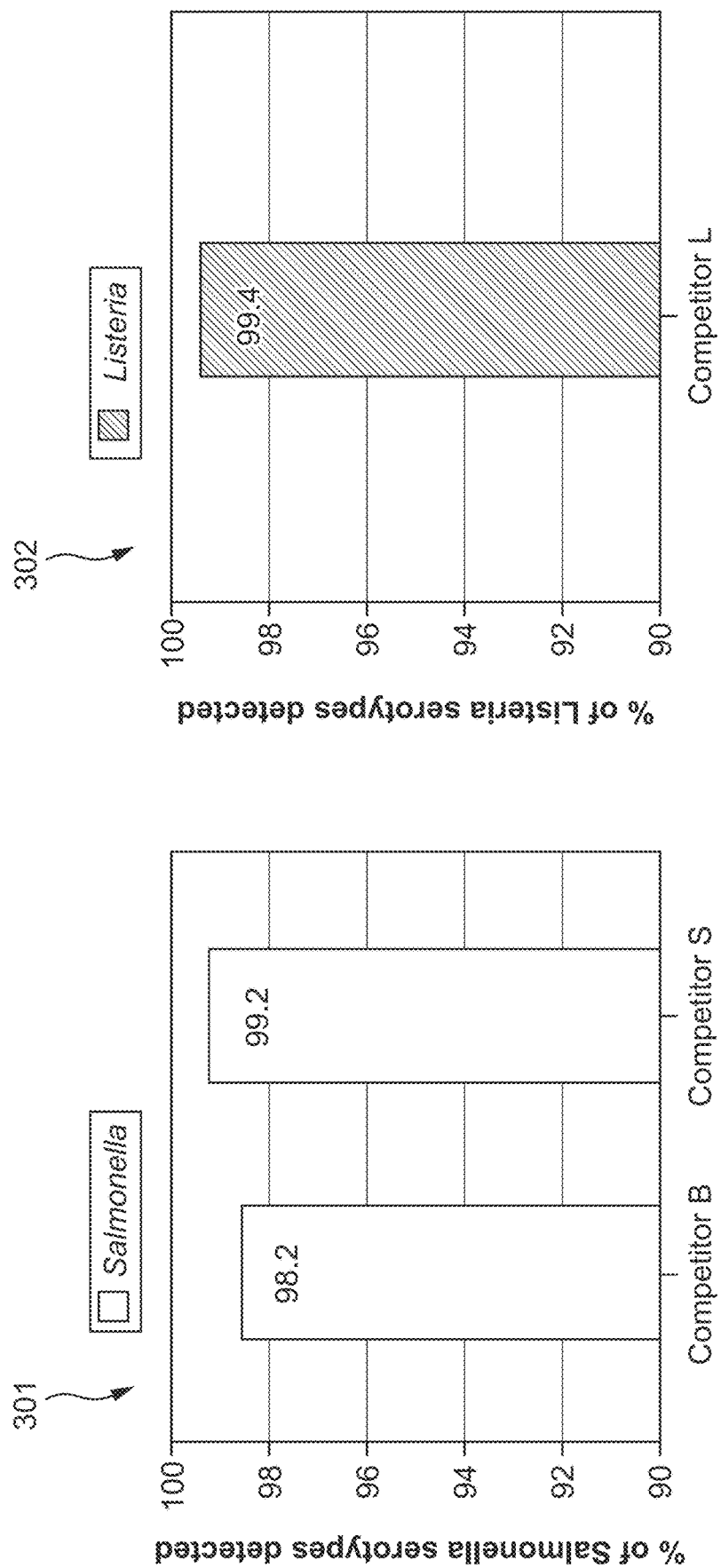
FIG. 3 is a chart illustrating that a redundancy in genetic markers decreases a false negative rate of a method of the disclosure.

In some aspects, an analysis of a redundancy in genetic markers increases a specificity and sensitivity of a method disclosed herein. FIG. 3 is a chart illustrating that a redundancy in genetic markers decreases a false negative rate of a method of the disclosure and increases its sensitivity as compared to PCR based methods. As shown in FIG. 3, three commercially available q/PCR based pathogen detection kits revealed that they would not detect all known *Salmonella* or *Listeria* genomes. 301 illustrates percentages of *Salmonella* detection by existing commercial kits. 302 illustrates percentages of *Listeria* detection by existing commercial kits.

A scanning of a plurality of nucleic acid regions within said plurality of nucleic acid sequences can characterize said one or more microorganisms with a desired specificity, sensitivity, or both. In some aspects, a scanning of no more than 0.001%, 0.01%, 0.1%, 1%, 5%, 10%, 25%, 50%, 90%, 99%, 100% or any number in between of nucleic acid regions within said plurality of nucleic acid sequences characterizes said one or more microorganisms with greater than 90%, 95%, 98%, 99%, 99.9%, 99.99% and 99.999% sensitivity. In some aspects, the method has fewer than 2%, fewer than 1.5%, fewer than 1.0%, fewer than 0.5%, or fewer than 0.1% of a false positive identification rate. In some aspects, a scanning of no more than 1% of a whole genome can characterize said microorganism.

In some instances, the high sensitivity and specificity of the disclosed methods are independent of a serotype of the microorganism. For instance, a scanning of a plurality of nucleic acid regions can identify a microorganism of the *Salmonella* genus that has a serotype selected from the group consisting of: Enteritidis, Typhimurium, Newport, Javiana, Infantis, Montevideo, Heidelberg, Muenchen, Saintpaul, Oranienburg, Braenderup, Paratyphi B var. L(+) Tartrate+, Agona, Thompson, and Kentucky; a microorganism of the *Escherichia* genus has a serotype selected from the group consisting of: O103, O111, O121, O145, O26, O45, and O157; a microorganism of the *Listeria* genus that has a serotype selected from the group consisting of: 2a, 1/2b, 1/2c, 3a, 3b, 3c, 4a, 4b, 4ab, 4c, 4d, and 4e; a microorganism of the *Campylobacter* genus with the *C. jejuni*, *C. lari*, or *C. coli* serotype and others.

A non-pathogenic strain of *Citrobacter*, namely *Citrobacter sedlakii*, expresses the *Escherichia coli* O157:H7 antigen. This is usually associated with a false positive detection of *E. coli* in a sample. Typically, when *Citrobacter* is erroneously classified as *E. coli*, a food lot may be unnecessarily disposed of and a food processing facility may be erroneously classified as a contaminated facility. In some aspects, the high sensitivity of the disclosed methods can be used to distinguish a microorganism from the *Escherichia* genus from a microorganism of the *Citrobacter* genus. In some instances, the disclosure provides a method comprising: scanning, by a computer, a plurality of sequencing reads from a food sample or from an environment associated with said food sample, whereby said scanning distinguishes a microorganism of a *Citrobacter* genus from a microorganism of an *Escherichia* genus by identifying one or more single nucleotide polymorphisms that are associated with either said *Citrobacter* genus or said *Escherichia* genus. Other examples include *E. coli* O157:H7 assay cross-reacting with *E. coli* O55 (which is not an STEC). Also some assays deliver false positives against *E. coli* O104 (which is not an STEC). *Citrobacter* is also a long-understood challenge for the some systems *E. coli* O157:H7.

In many cases, disease outbreaks require a rapid response, often including multijurisdictional coordination. In some aspects, the disclosure provides methods for the rapid identification of a microorganism from a food sample. In some instances, the disclosure provides a method for sequencing a plurality of nucleic acid sequences from a food sample, from an environmental sample associated with said food sample or from another sample (such as a clinically derived sample) for a period of time; and performing an assay on said food sample or said environment associated with said food sample if said sequencing for said period of time identifies a threshold level of nucleic acid sequences from a microorganism in said food sample. In some instances said period of time is less than 12 hours, less than 6 hours, less than 4 hours, less than 2 hours, less than 1 hour, less than 30 minutes, less than 20 minutes, less than 15 minutes or another suitable time. FIG. 4 is a schematic illustrating a sequencing of a plurality of nucleic acid sequences from a food sample for a period of time and the advantages of performing an assay on said food sample if said sequencing for said period of time identifies a threshold level of nucleic acid sequences from a microorganism in said food sample.

Pathogenic Microorganisms

In general, a microorganism that can injure its host, e.g., by competing with it for metabolic resources, destroying its cells or tissues, or secreting toxins can be considered a pathogenic microorganism. Examples of classes of pathogenic microorganisms include viruses, bacteria, mycobacteria, fungi, protozoa, and some helminths. In some aspects, the disclosure provides methods for detecting one or more microorganisms from a food sample or from an environment associated with said food sample—such as from a table, a floor, a boot cover, an equipment of a food processing facility—or from a food related sample that comprise soil, water, water quality, air, animal production, feed, manure, crop production, manufacturing plants, environmental samples, or non-food derived samples, such as samples from clinical sources that comprise blood, plasma, urine, tissue, faces, bone marrow, saliva or cerebrospinal fluid by analyzing a plurality of nucleic acid sequencing reads from such samples.

Many pathogenic microorganisms are further subdivided into serotypes, which can differentiate strains by their surface and antigenic properties. For instance *Salmonella* species are commonly referred to by their serotype names. For example, *Salmonella enterica* subspecies enterica is further divided into numerous serotypes, including *S. enteritidis* and *S. typhimurium*. In some aspects, the methods of the disclosure can distinguish between such subspecies of a variety of *Salmonella* by analyzing their nucleic acid sequences.

*Escherichia coli* (*E. coli*) bacteria normally live in the intestines of people and animals. Many *E. coli* are harmless and in some aspects are an important part of a healthy human intestinal tract. However, many *E. coli* can cause illnesses, including diarrhea or illness outside of the intestinal tract and should be distinguished from less pathogenic strains. In some aspects, the methods of the disclosure can distinguish between various subspecies of a variety of *Escherichia* bacteria by analyzing their nucleic acid sequences.

*Listeria* is a harmful bacterium that can be found in refrigerated, ready-to-eat foods (meat, poultry, seafood, and dairy—unpasteurized milk and milk products or foods made with unpasteurized milk), and produce harvested from soil contaminated with, for example, *L. monocytogenes*. Many animals can carry this bacterium without appearing ill, which increases the challenges in identifying the pathogen derived from a food source. In addition, some species of *Listeria* can grow at refrigerator temperatures where most other foodborne bacteria do not, another factor that increases the challenges of identifying *Listeria*. When eaten, *Listeria* may cause listeriosis, an illness to which pregnant women and their unborn children are very susceptible. In some aspects, the methods of the disclosure can distinguish between various subspecies of a variety of *Listeria* bacteria by analyzing their nucleic acid sequences.

*Campylobacter jejuni* is estimated to be the third leading bacterial cause of foodborne illness in the United States. Raw poultry, unpasteurized ("raw") milk and cheeses made from it, and contaminated water (for example, unchlorinated water, such as in streams and ponds) are major sources of *Campylobacter*, but it also occurs in other kinds of meats and has been found in seafood and vegetables. In some aspects, the methods of the disclosure can distinguish between various subspecies of a variety of *Campylobacter* bacteria by analyzing their nucleic acid sequences.

Non-limiting examples of pathogenic microorganisms that can be detected with the methods of the disclosure include: pathogenic *Escherichia coli* group, including Enterotoxigenic *Escherichia coli* (ETEC), Enteropathogenic *Escherichia coli* (EPEC), Enterohemorrhagic *Escherichia coli* (EHEC), Enteroinvasive *Escherichia coli* (EIEC), *Salmonella* spp., *Campylobacter jejuni, Listeria, Yersinia enterocolitica, Shigella* spp., *Vibrio parahaemolyticus, Coxiella burnetii, Mycobacterium bovis, Brucella* spp., *Vibrio cholera, Vibrio vulnificus, Cronobacter, Aeromonas hydrophila* and other spp., *Plesiomonas shigelloides, Clostridium perfringens, Clostridium botulinum, Staphylococcus aureus, Bacillus cereus* and other *Bacillus* spp., *Listeria monocytogenes, Streptococcus* spp., *Enterococcus*, and others.

Identifying a New Microorganism in an Environment

Disclosed herein are methods and apparatuses that allow the distinction of a microorganism that has been newly introduced into a food processing facility or any other environmental setting in which tracking hygiene is critical, such as a hospital or a clinic. In some instances, resident microorganisms reflect a persistent contamination within a location, e.g., a food processing facility or a hospital, that is very different than the transient pathogens that are being repeatedly introduced into the locations. Discriminating resident and transient pathogens provides more clarity for differentiation of source of contaminations and intervention strategies. This strategy can be used, for example, to manage contaminations with managing contaminations with *Listeria monocytogensis*. For example, *Campylobacter* is part of the natural gut microflora of most food-producing animals, such as chickens, turkeys, swine, cattle, and sheep. Typically, each contaminated poultry carcass can carry from about 100 to about 100,000 *Campylobacter* cells. On one hand, given the fact that less than 500 *Campylobacter* cells can cause infection, poultry products pose a significant risk for consumers who mishandle fresh or processed poultry during preparation or who undercook it. On another hand, one must be able to distinguish a normal level of a *Campylobacter* on a food carcass from a *Campylobacter* overgrowth in a sample or from the presence of a new strain of *Campylobacter* in a food processing facility, environment, or food sample. One must also be able to identify a new source of contamination in a facility from existing sources. FIG. 4 illustrates a process for predictive risk assessment based on a detection of a non-pathogenic microorganism. Briefly, a food sample, such as a steak sample illustrated as 401 is processed and an assay, such as a nucleic acid sequencing reaction is performed. An analysis of a plurality of nucleic acid sequencing reads from 401 may, in some instances, not detect a particular pathogen, such as the *E. coli* pathogen illustrated in this example. Nevertheless, an analysis 403 of the microbiome 402 of the food sample 401 may indicate high risk for a presence of a pathogen, such as *E. coli*. In such instances, the food sample may be re-sampled and re-processed to confirm the presence of a pathogenic microorganism therein.

In some instances, the methods disclosed herein further comprise performing an additional assay to confirm the presence of the pathogenic microorganism in the sample, such as a serotyping assay, a polymerase chain reaction (PCR) assay, an enzyme-linked immunosorbent (ELISA) assay, or an enzyme-linked fluorescent assay (ELFA) assay, restriction fragment length polymorphisms (RFLP) assay, pulse field gel electrophoresis (PFGE) assay, multi-locus sequence typing (MLST) assay, targeted DNA sequencing assay, whole genome sequencing (WGS) assay, or shotgun sequencing assay.

In some aspects, the disclosure provides a method comprising obtaining a first plurality of nucleic acid sequences from a first sample of a food processing facility; creating a data file in a computer that associates one or more of said first plurality of nucleic acid sequences with said food processing facility; obtaining a second plurality of nucleic acid sequences from a second food sample of said food processing facility; and scanning a plurality of sequences from said second plurality of nucleic acid sequences for one or more sequences associated with said food processing facility in the created data file.

One or more data files can be created that associate a microorganism with a food processing facility. In some instances, a data file can provide a collection of sequencing reads that can be associated with one or more strains of a microorganism present in the processing facility. In some cases, more than 10, 15, 20, 25, 30, 35, 40, 45, 50, 60, 70, 80, 90, 100, or 1000 bacterial strains can be associated with one or more food processing facilities.

Correlating a Presence of a Microorganism with the Risk Associated with a Food Sample The instance disclosure recognizes that a presence of some non-pathogenic microorganisms, i.e. indicator microorganisms, can be correlated with a presence of pathogenic bacteria in food, in environmental samples, or another sample. In some aspects the disclosure provides a method comprising detecting a presence or an absence of a non-pathogenic microorganism in a food sample, an environment associated with said food sample, or another sample described herein, by a computer system, and a presence or an absence of a pathogenic microorganism in said food sample, environment associated, or another sample based on said presence or said absence of said non-pathogenic microorganism. FIG. 5 is a heat map illustrating predictive pathogen detection through machine learning using associated non-pathogenic microorganisms. Data was collected from more than 20,000 food samples varying over the food categories identified by CODEX, with presentation proportional to their market share. Among those about 950 samples were identified to have pathogens present. The pathogens were detected via Clear Labs sequencing platform, as well as, with traditional culturing. Via sequencing multiple regions, the bacteria present in the samples were detected and quantified (relative to each other) at the species level.

The data was supplemented by alpha diversity measures including Shannon entropy, number of observed OTUs, and Faith's phylogenetic diversity measure. The quantification of the bacteria in the samples and these supplemented measures, provided coordinates for the data points used in the final classification. The distance between the data points was computed as a combination of unifrac distance and the euclidean distance restricted to the supplemented coordinates.

The data points were split into training and test subsets. We used stratified 10-fold cross validation to train support vector machine model on the training set. The performance of the model was measured on the previously separated test set. The scores with regard to detection of some of the pathogens is presented in FIG. 5.

The coefficients of the support vector machine classifier were used to determine bacteria that play significance in determining presence or absence of the pathogens and therefore to provide signatures that can be used independently of the model. This analysis determined a set of non-pathogenic microorganisms that had statistically significant correlation with the presence of pathogenic organisms, including members of the genus *Enterobacter*. *Enterobacter asburiae, Enterobacter bugandensis, Enterobacter cancerogenus, Enterobacter cloacae, Enterobacter endosymbiont, Enterobacter hormaechei, Enterobacter kobei, Enterobacter ludwigii*, and *Enterobacter soli* were among the top 9 examples of non-pathogenic bacteria associated with our set of pathogenic bacteria. For example, *Yersinia pseudotuberculosis* was associated with *Enterobacter asburiae*; *Vibrio vulnificus* was associated with *Enterobacter bugandensis, Enterobacter endosymbiont*, and *Enterobacter soli*; *Escherichia coli, Salmonella enterica*, and *Shigella boydii* were associated with *Enterobacter cancerogenus, Enterobacter cloacae*, and *Enterobacter hormaechei*; *Staphylococcus Aureus* was associated with *Enterobacter kobei*; and *Yersinia pseudotuberculosis* was associated with *Enterobacter asburiae* and *Enterobacter ludwigii*.

Without being limited by theory, a variety of other samples described herein can be analyzed as described. Briefly, a sample may be screened with any one of the methods described herein and a plurality of nucleic acid sequences may be obtained. Numerous sequences within said plurality of nucleic acid sequences may be correlated by a machine learning algorithm with a variety of microorganisms. A prediction can then be created and a visual output of such prediction, such as the illustrated a heat map can be created by detecting statistically significant correlations. For instance, a heat map created by a machine learning algorithm may illustrate a correlation between a presence of *E. coli, Salmonella enterica*, and *Shigella boydii* of one or more non-pathogenic microorganisms from the *Enterobacter* genus, such as *Enterobacter cancerogenus, Enterobacter cloacae*, and *Enterobacter hormaechei* or any other bacterial genera. In some aspects, a machine learning algorithm, including the machine learning algorithms described herein, can be used to create such predictions.

A statistical analysis can be performed to identify the top nonpathogenic species/food ingredients associated with the presence of *Vibrio/Staphylococcus/Yersinia/Shigella/Salmonella/Escherichia* (an illustrative cluster-based representation of such analysis is presented in FIG. 5). This analysis determined a set of non-pathogenic microorganisms that had statistically significant correlation with the presence of pathogenic organisms, including members of the genus *Enterobacter. Enterobacter asburiae, Enterobacter bugandensis, Enterobacter cancerogenus, Enterobacter cloacae, Enterobacter endosymbiont, Enterobacter hormaechei, Enterobacter kobei, Enterobacter ludwigii,* and *Enterobacter soli* were among the top 9 examples of non-pathogenic bacteria associated with our set of pathogenic bacteria. For example, *Yersinia pseudotuberculosis* was associated with *Enterobacter asburiae; Vibrio vulnificus* was associated with *Enterobacter bugandensis, Enterobacter endosymbiont,* and *Enterobacter soli; Escherichia coli, Salmonella enterica,* and *Shigella boydii* were associated with *Enterobacter cancerogenus, Enterobacter cloacae,* and *Enterobacter hormaechei; Staphylococcus Aureus* was associated with *Enterobacter kobei;* and *Yersinia pseudotuberculosis* was associated with *Enterobacter asburiae* and *Enterobacter ludwigii.*

Food is a chemically complex matrix. Predicting whether, or how fast, microorganisms will grow in a food, or how quickly a food may spoil, is difficult. For instance, most foods contain sufficient nutrients to support microbial growth. Furthermore, there are many additional factors that encourage, prevent, or limit growth of microorganisms in foods including pH, temperature, and relative humidity. In some aspects, the instant disclosure recognizes that a presence of some microorganism, whether or not pathogenic, can be correlated with a sell-by date, i.e., a spoilage date of a food. In some aspects the disclosure provides a method comprising: detecting a presence or an absence of a microorganism in a food sample or in an environmental sample from a food processing facility; and predicting, by a computer system, a risk presented by said food sample or by said food processing facility based on said presence or said absence of said microorganism.

Figure 6:
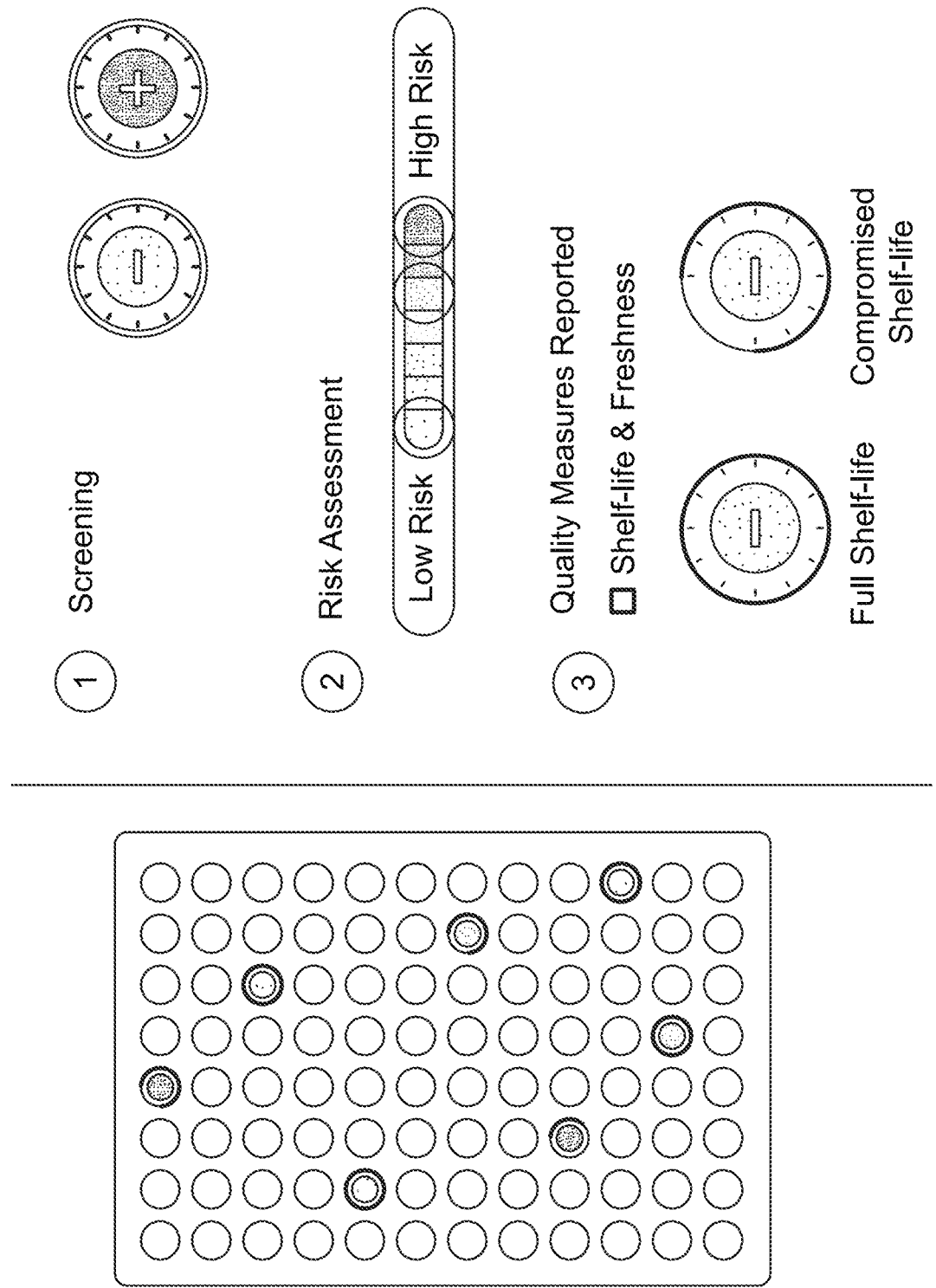
FIG. 6 illustrates a process for predicting a shelf-life of a food based on the detection of a microorganism.

FIG. 6 illustrates a process for predicting a shelf-life of a food based on machine learning. Briefly, FIG. 6 illustrates a screening of a sample, such as a screening of a plurality of nucleic acid sequencing reads. Subsequently, a machine learning algorithm is used to create a risk profile, whereby said risk profile associates a presence of some microorganism with a low or a high likelihood of food spoilage, thereby predicting the sell-by date of a food.

A machine learning algorithm can be used to associate any number of sequencing reads with a presence of microorganism in a food sample, a food related sample, or another sample. Similarly, a machine learning algorithm may be able to associate any number of sequencing reads with a presence of a pathogenic microorganism, even if the sequence reads themselves are not from the pathogenic microorganism. Computer-implemented methods for generating a machine learning-based classifier in a system may require a number of input datasets in order for the classifier to produce highly accurate predictions. Depending on the microorganism, matrix, and the microorganisms abundance in the real life samples of the matrix, the data can be in range of 100, 1000, 10000, 100000, 1000000, 10000000, 100000000 sequencing reads. A machine learning algorithm is selected from the group consisting of: a support vector machine (SVM), a Naïve Bayes classification, a random forest, Logistic regression and a neural network.

Tuning an Assay Resolution

Figure 7:
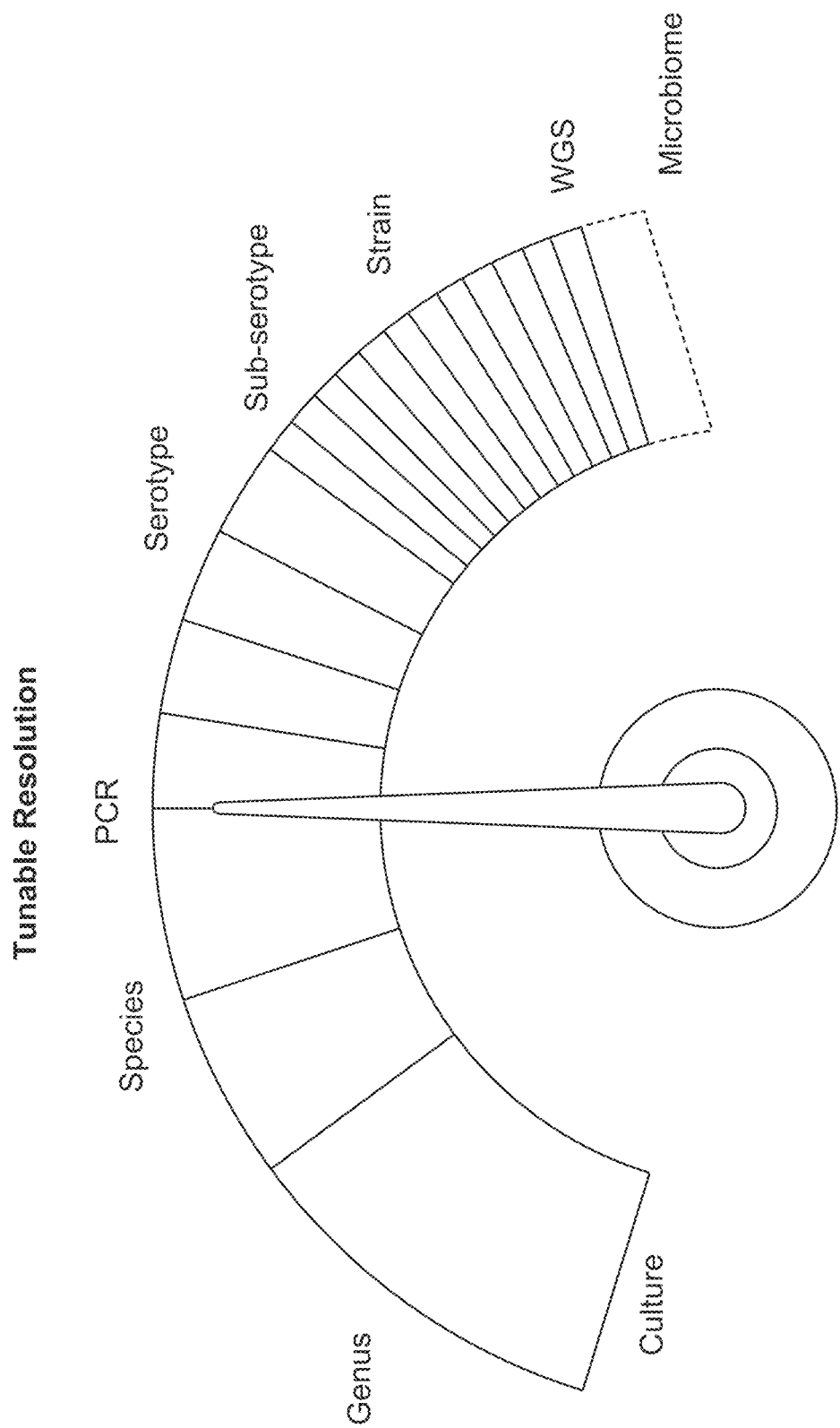
FIG. 7 is a diagram illustrating the tunable resolution of various assays.

One can tune the resolution for the detection of a microorganism based on the source of the sample, e.g., food versus surface swab; and the sensitivity of the assay itself, e.g., genus, species, serotype, versus strain (obtained via whole genome sequencing). FIG. 7 is a diagram illustrating the tunable resolution of various assays. Briefly, one or more assays can be used sequentially to obtain a desired level of sensitivity, such as to determine a genus, a species, a serotype, a sub-serotype, or a strain of said microorganism. The assays can be identical or they can be distinct. FIG. 7 illustrates that a sequencing assay can be used to identify a strain or a sub-serotype of a microorganism whereas a PCR reaction may be able to identify a species or, in some cases, a serotype of a particular microorganism.

In some aspects, the disclosure provides a method comprising: obtaining a plurality of nucleic acid sequences of a food sample, of an environmental sample or of another non-food derived sample from a food processing facility or another facility; performing a first assay in said plurality of nucleic acid sequences of said food sample, whereby said assay predicts a presence or predicts an absence of a microorganism in said food sample; and determining, based on said predicted presence or said predicted absence of said microorganism of the first assay whether to perform a second assay, whereby a sensitivity of said second assay is selected to determine a genus, a species, a serotype, a sub-serotype, or a strain of said microorganism.

There are various approaches for processing nucleic acids from food samples or from environmental samples, such as polymerase chain reaction (PCR) and sequencing. In some cases said assay is a sequencing assay that provides the ability to obtain sequencing-reads in real time, such as pore sequencing assay. Sequencing can be performed by various systems currently available, such as, without limitation, a sequencing system by Illumina®, Pacific Biosciences (PacBio®), Oxford Nanopore®, Genia (Roche) or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification.

Various strategies may be used for amplification. In some cases, the nucleic acid amplification, polymerase chain reaction (PCR) (e.g., digital PCR, quantitative PCR, or real time PCR), or isothermal amplification involves amplification with fully or partially degenerate primers. In some cases, the nucleic acid amplification, polymerase chain reaction (PCR) (e.g., digital PCR, quantitative PCR, or real time PCR), or isothermal amplification involves targeted amplification of particular gene or genomic regions. In some cases, targeted amplification of particular gene or genomic regions involves targeted amplification of regions containing and/or circumscribing SNPs, RFLPs, STRs, VNTRs, hypervariable regions, minisatellites, dinucleotide repeats, trinucleotide repeats, tetranucleotide repeats, simple sequence repeats, indels, and/or insertion elements associated with or variable between individual microorganisms or microorganism serotypes. The targeted amplification of the particular gene or genomic regions may involve the use of multiple sets of oligonucleotide primers that are partially or fully complementary to regions flanking the SNPs, RFLPs, STRs, VNTRs, hypervariable regions, minisatellites, dinucleotide repeats, trinucleotide repeats, tetranucleotide repeats, simple sequence repeats, indels, and/or insertion elements. In some embodiments, the targeted amplification uses at least one, 100, 200, 300, 400, 500, 600, 700, or 800 pairs of oligonucleotide primers to amplify particular gene or genomic regions from the nucleic acids.

Figure 8:
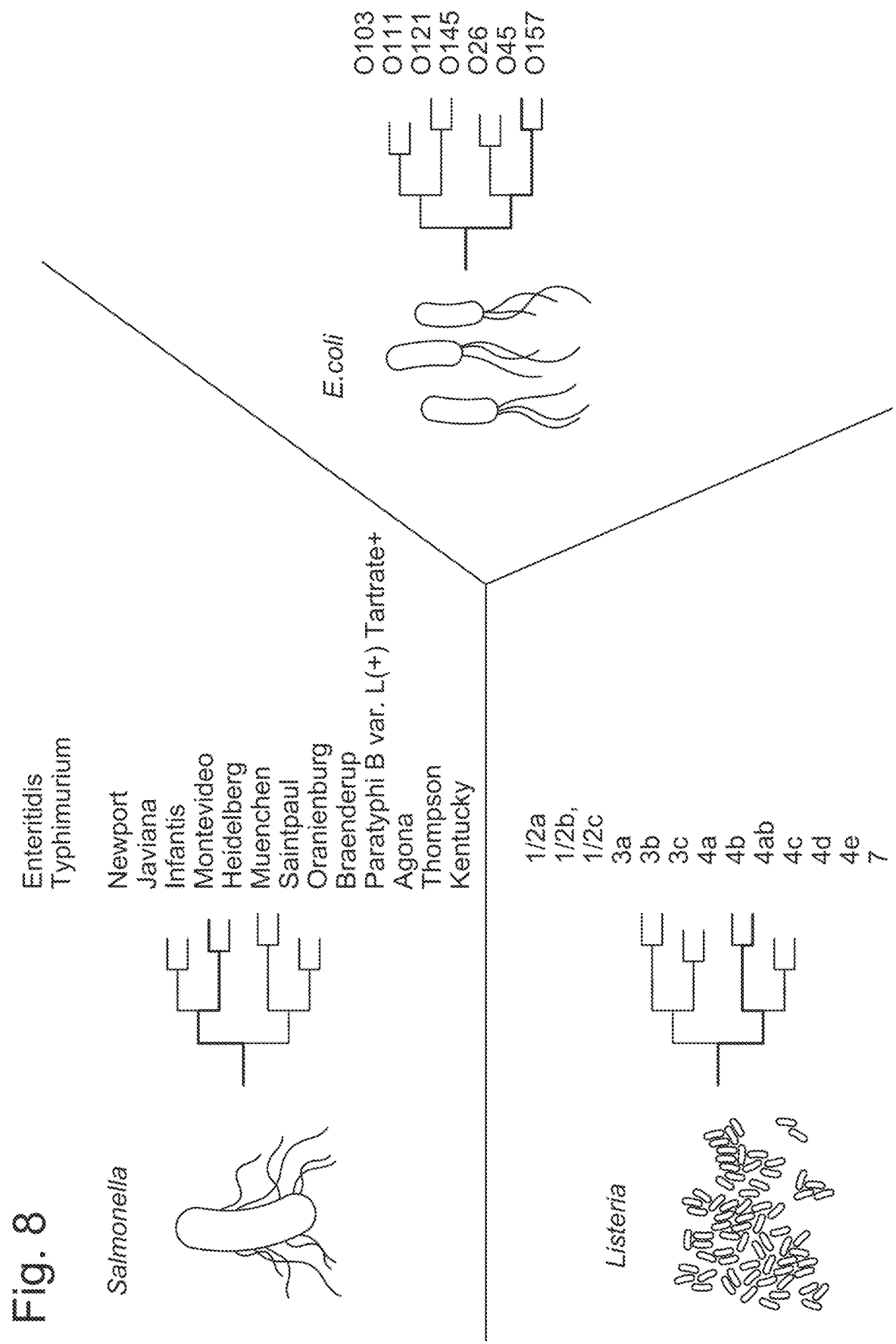
FIG. 8 is a schematic illustrating various serotypes of various microorganisms that can be detected by an analysis of a plurality of nucleic acid sequences as described herein and further validated with a serotyping assay.

In some cases, the assay is a serotyping assay. The serotyping assay may comprise an enzyme-linked immunosorbent (ELISA) assay or an enzyme-linked fluorescent assay (ELFA) assay. A serotype or serovar is a distinct variation within a species of bacteria or virus. These microorganisms can be classified together based on their cell surface antigens, allowing the epidemiologic classification of microorganisms to the sub-species level. A group of serovars with common antigens is called a serogroup or sometimes serocomplex. In some aspects, the disclosure provides methods for performing a sequencing assay on a plurality of nucleic acids derived from a sample and a then performing a serotyping assay on a derivative of said sample. FIG. 8 is a schematic illustrating various serotypes of various microorganisms that can be detected by an analysis of a plurality of nucleic acid sequences as described herein and further validated with a serotyping assay.

Differentiating Live versus Dead Microorganisms

Figure 9:
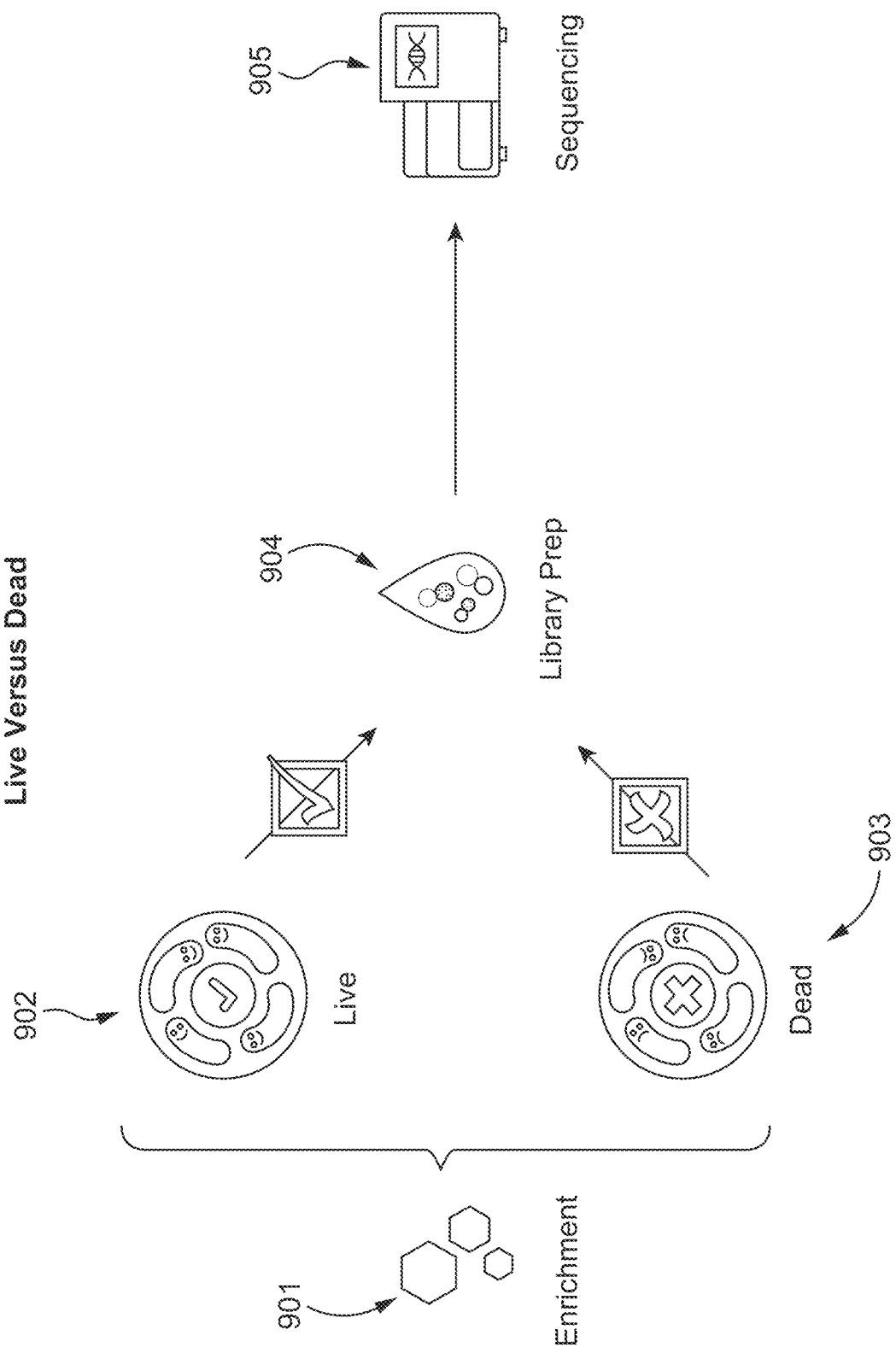
FIG. 9 is a schematic illustrating one process for distinguishing a live microorganism from a food or from an environmental sample.

Nucleic acid-based targeted analytical methods, such as PCR provide only limited information on the activities and physiological states of microorganisms in samples and cannot distinguish viable cells from dead cells. In some aspects, the disclosure provides methods for distinguishing a live microorganism in a food sample or in another sample, from a dead microorganism within the same sample. FIG. 9 is a schematic illustrating one process for distinguishing a live microorganism from a food or from an environmental sample. Briefly, FIG. 9 illustrates than an amount of a microorganism in a sample can be increased, i.e., enriched 901, by growing the microorganism in a rich medium for a period of time. A reagent, such as a photoreactive DNA-binding dye, a DNA intercalating reagent, or another suitable reagent may be added to enriched sample 901. Such reagents distinguish live 902 microorganisms from dead 903 microorganisms by interacting with the nucleic acid sequence of dead microorganisms only. In some cases, the disclosure contemplates using propidium monoazide or a derivative thereof as a dye. The modified sample can be prepared for a subsequent reaction 904, such as a sequencing reaction 905.

In some instances the disclosure provides a method comprising adding a reagent to a plurality of nucleic acid molecules from a food sample, or food related sample or another sample described herein thereby forming a modified plurality of nucleic acid molecules, whereby said reagent (i) interacts with and modifies a structure of a plurality of nucleic acid molecules derived from one or more dead microorganisms; and (ii) does not interact with or modify a structure of a nucleic acid molecule derived from one or more live microorganisms; thereby providing a modified plurality of nucleic acid molecules; and sequencing said modified plurality of nucleic acid molecules, thereby distinguishing one or more live organisms from said food sample or from another sample.

In other aspects the disclosure provides a method comprising performing a pore sequencing or other DNA sequencing or hybridization assay on a plurality of nucleic acid molecules from a food sample or from another sample whereby said pore sequencing reaction distinguishes one or more nucleic acid molecules derived from a dead microorganism from one or more nucleic acid molecules derived from a live microorganism based on a methylation or other epigenetic pattern of said one or more nucleic acid molecules derived from said dead microorganism.

In some embodiments, epigenetic patterns, such as methylation, can be detected in DNA derived from food or environmental samples by chemical or enzymatic selection methods prior to sequencing. Such methods include, but are not limited to, bisulfite sequencing (including targeted bisulfite sequencing, see e.g. Ziller et al. Epigenetics Chromatin. 2016 Dec. 3; 9:55 and Masser et al. J Vis Exp. 2015; (96): 52488) and methylation-sensitive restriction digestion (see e.g. Bitinaite et al. U.S. Pat. No. 9,034,597).

In some embodiments, epigenetic patterns can be detected in DNA derived from food or environmental samples by characteristic changes in ionic current during nanopore sequencing (see e.g. Wescoe et al. J Am Chem Soc. 2014 Nov. 26; 136(47):16582-7 and Laszlo et al. Proc Natl Acad Sci USA. 2013 Nov. 19; 110(47):18904-9).

Barcodes

Unique identifiers, such as barcodes, can be added to one or more nucleic acids isolated from a sample from a food processing facility, from a hospital or clinic, or from another sources. Barcodes can be used to associate a sample with a source; e.g., to associate an environmental sample with a specific food processing facility or with a particular location within said food processing facility. Barcodes can also be used to identify a processing of a sample, as described in U.S. Patent Pub. No. 2016/0239732, which is entirely incorporated herein by reference.

Figure 10:
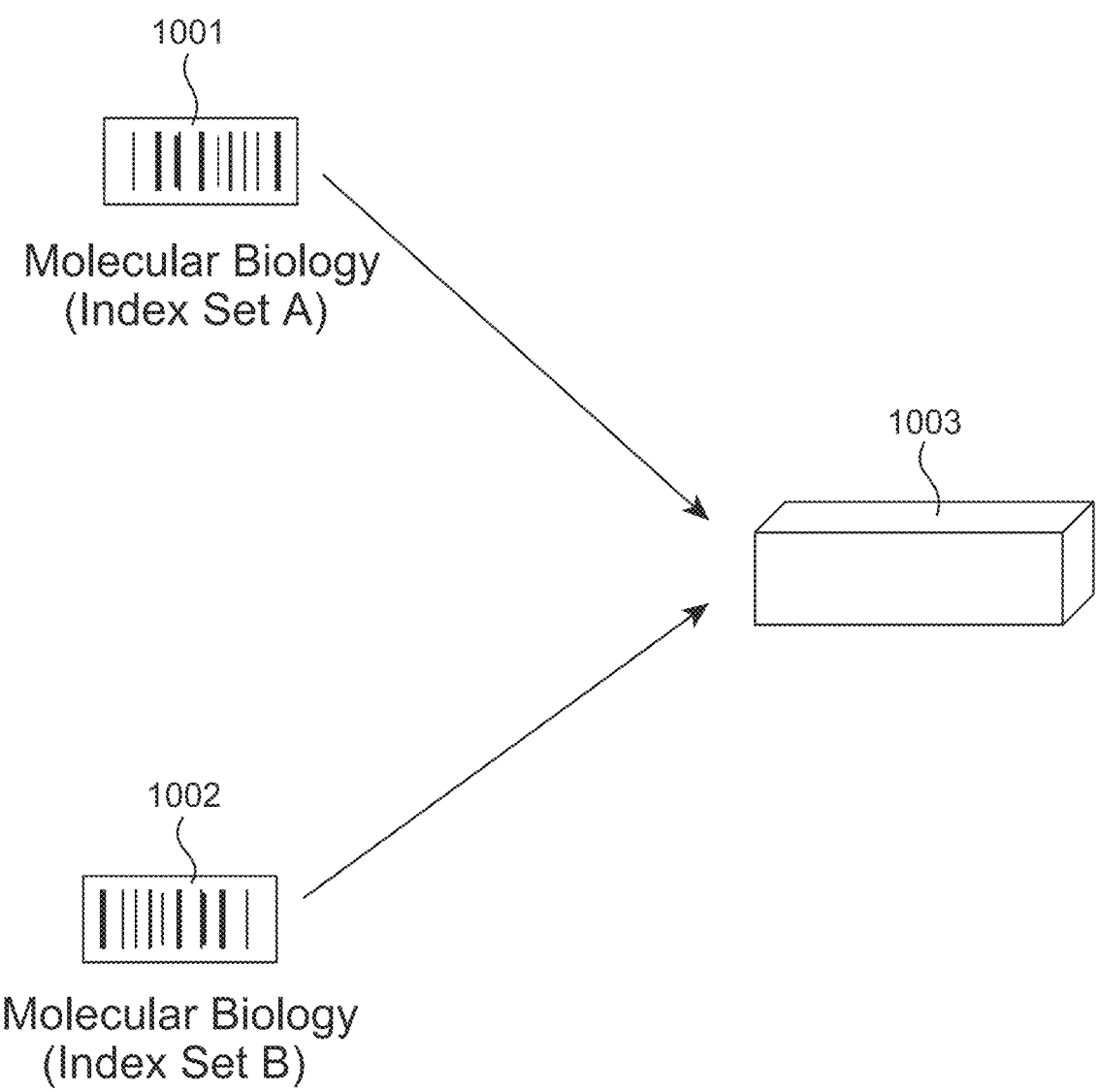
FIG. 10 illustrates a process for re-using flow cells with distinct indexes.
Figure 18:
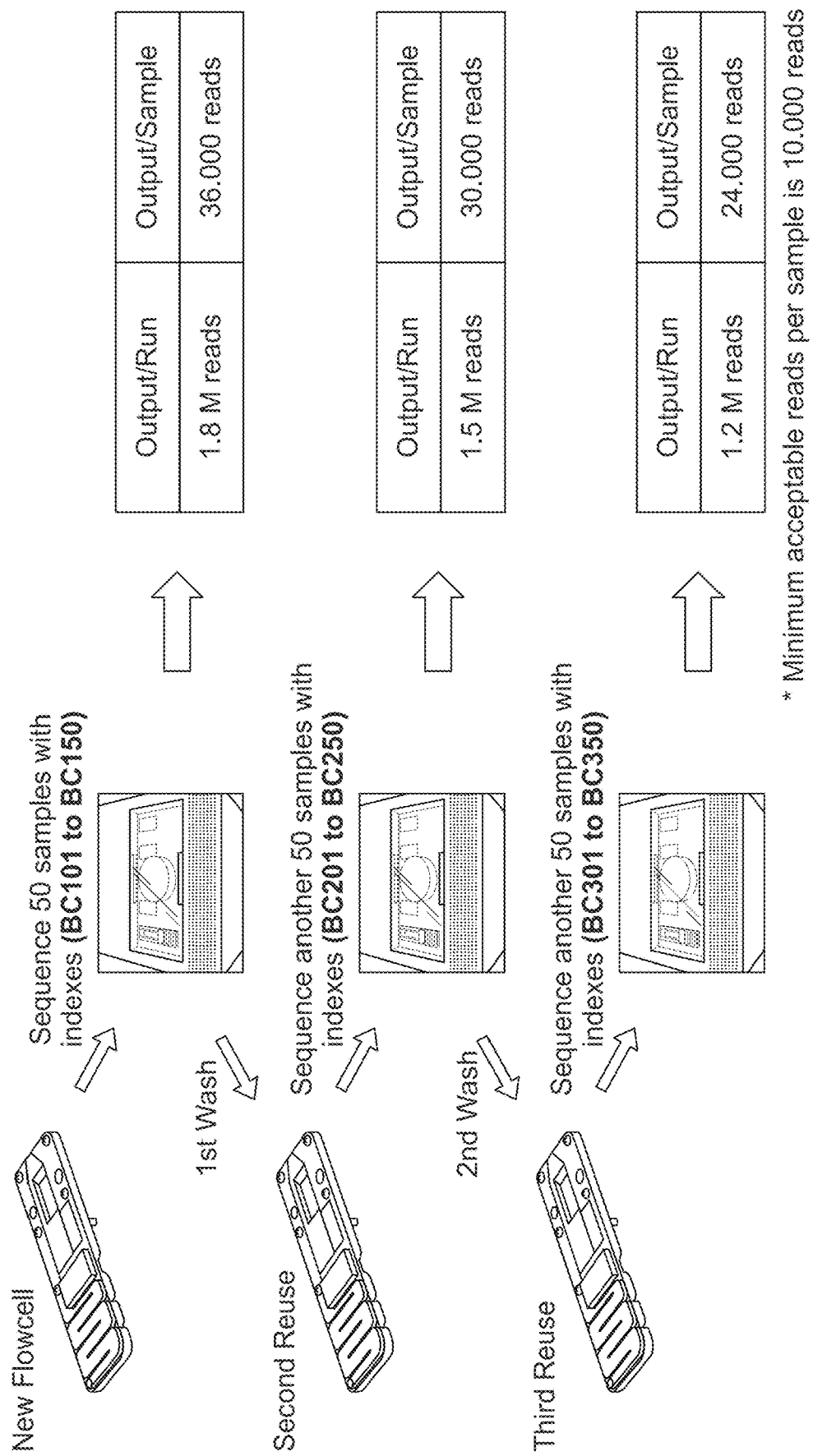
FIG. 18 illustrates the reuse of MinION/GridION flow cells.
Figure 19:
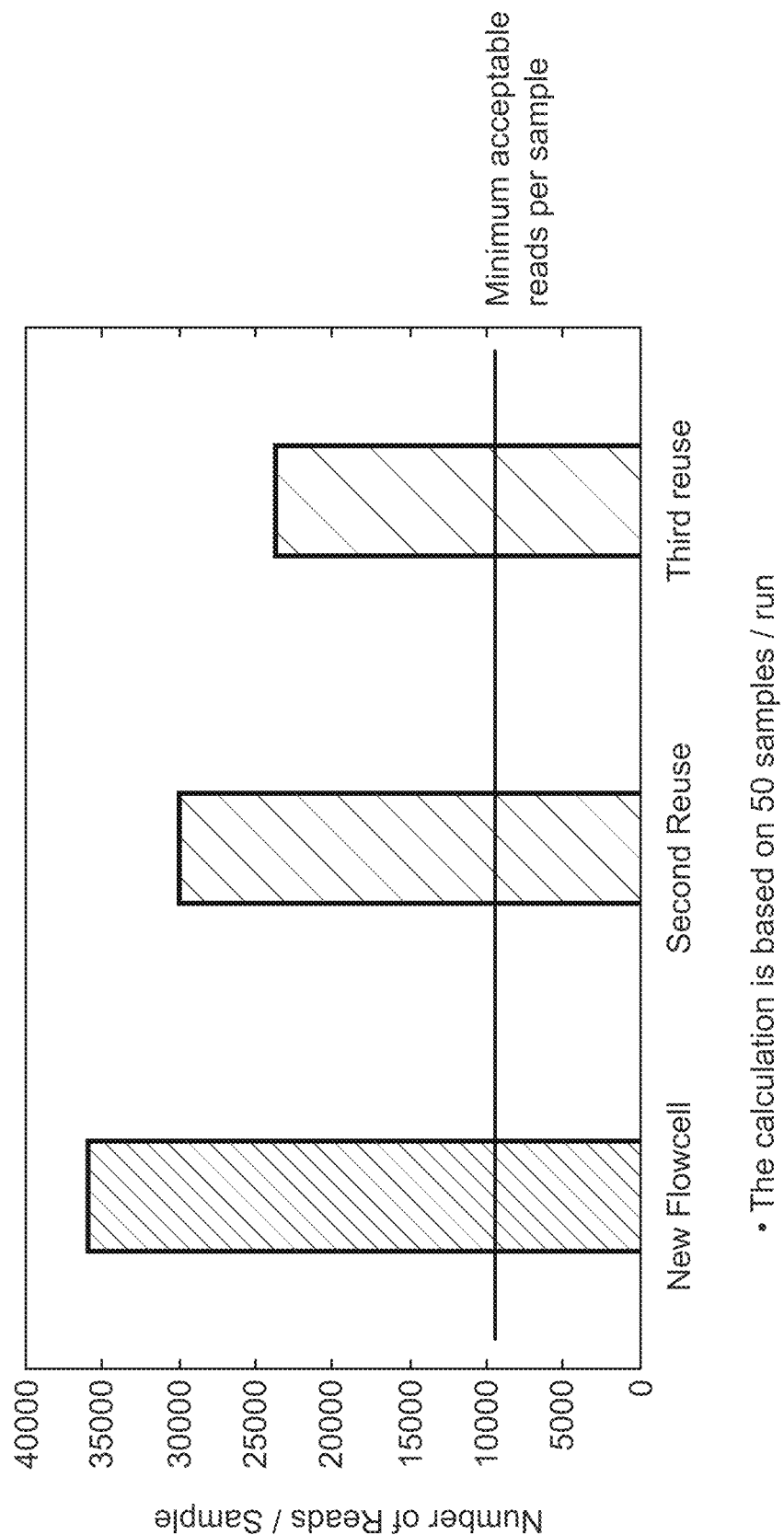
FIG. 19 illustrates the number of reads per sample during reuse of MinION/GridION flow cells.

In some aspects, the disclosure provides a method comprising adding a first barcode to a first plurality of nucleic acid sequences from a sample, thereby providing a first plurality of barcoded nucleic acid sequences; performing a first sequencing reaction on said first plurality of barcoded nucleic acid sequences, wherein said sequencing reaction is performed on a sequencing apparatus comprising a flow cell; adding a second barcode to a second plurality of nucleic acid sequences from a second sample, thereby providing a second plurality of barcoded nucleic acid sequences; and performing a second sequencing reaction on said second plurality of barcoded nucleic acid sequences, wherein said second sequencing reaction is performed on said sequencing apparatus comprising said flow cell, thereby reusing said flow cell. FIG. 10 illustrates a process for re-using flow cells with distinct indexes as described herein. As illustrated by FIG. 10 two distinct indexes, 1001 and 1002, such as two different barcodes, can be added to different samples prior to sequencing 1003. Since a first sample can be associated with a first index 1001 and a second sample can be associated with a second index 1002 this process effectively allows for the re-using of a flow cell. FIG. 18 and FIG. 19 demonstrate the re-use of MinION/GridION flow cells. Example 21 demonstrates how certain primer design schemes, such as a nonperiodic design, can reduce crosstalk in situations with high multiplexing or closely related sequences, as may happen with reuse of flow cells.

One or more barcodes or block of barcodes may be added to a nucleic acid sequence from a food sample or another sample from a food processing facility, such as a first, a second, a third, or any subsequent sample. In some cases, 1, 2, 3, 4, 5, 6, 7, 8, 9, 10, 11, 12, 13, 14, 15, 16, 17, 18, 19, or 20 identical barcodes are added to such samples. In other cases, distinct barcodes are added to such samples. In some cases, 1, 2, 3, 4, 5, 6, 7, 8, 9, 10, 11, 12, 13, 14, 15, 16, 17, 18, 19, or 20 distinct barcodes are added to such samples. The serial addition of two or more barcodes, either identical in sequence or distinct in sequence, can provide an indexing of a sample that is used in its analyses. The presence of additional barcode or barcode blocks make the system more robust against any barcode manufacturing error and can also significantly reduce the chance of cross contamination between barcodes. In some cases, a barcode is added to a nucleic acid sequence comprising complementary DNA (cDNA) sequences, ribonucleic acid (RNA) sequences, genomic deoxyribonucleic acid (gDNA) sequences, or a mixture of cDNA, RNA, and gDNA sequences.

Barcodes can have a variety of lengths. In some instances a barcode is from about 3 to about 25 nucleotides in length, from about 3 to about 24 nucleotides in length, from about 3 to about 23 nucleotides in length, from about 3 to about 22 nucleotides in length, from about 3 to about 21 nucleotides in length, from about 3 to about 20 nucleotides in length, from about 3 to about 19 nucleotides in length, from about 3 to about 18 nucleotides in length, from about 3 to about 17 nucleotides in length, from about 3 to about 16 nucleotides in length, from about 3 to about 15 nucleotides in length, from about 3 to about 14 nucleotides in length, from about 3 to about 13 nucleotides in length, from about 3 to about 12 nucleotides in length, from about 3 to about 11 nucleotides in length, from about 3 to about 10 nucleotides in length, from about 3 to about 9 nucleotides in length, from about 3 to about 8 nucleotides in length, or from about 3 to about 7 nucleotides in length.

In other instances, a barcode is from about 4 to about 25 nucleotides in length, from about 4 to about 24 nucleotides in length, from about 4 to about 23 nucleotides in length, from about 4 to about 22 nucleotides in length, from about 4 to about 21 nucleotides in length, from about 4 to about 20 nucleotides in length, from about 4 to about 19 nucleotides in length, from about 4 to about 18 nucleotides in length, from about 4 to about 17 nucleotides in length, from about 4 to about 16 nucleotides in length, from about 4 to about 15 nucleotides in length, from about 4 to about 14 nucleotides in length, from about 4 to about 13 nucleotides in length, from about 4 to about 12 nucleotides in length, from about 4 to about 11 nucleotides in length, from about 4 to about 10 nucleotides in length, from about 4 to about 9 nucleotides in length, from about 4 to about 8 nucleotides in length, or from about 4 to about 7 nucleotides in length.

a barcode is from about 5 to about 25 nucleotides in length, from about 5 to about 24 nucleotides in length, from about 5 to about 23 nucleotides in length, from about 5 to about 22 nucleotides in length, from about 5 to about 21 nucleotides in length, from about 5 to about 20 nucleotides in length, from about 5 to about 19 nucleotides in length, from about 5 to about 18 nucleotides in length, from about 5 to about 17 nucleotides in length, from about 5 to about 16 nucleotides in length, from about 5 to about 15 nucleotides in length, from about 5 to about 14 nucleotides in length, from about 5 to about 13 nucleotides in length, from about 5 to about 12 nucleotides in length, from about 5 to about 11 nucleotides in length, from about 5 to about 10 nucleotides in length, from about 5 to about 9 nucleotides in length, from about 5 to about 8 nucleotides in length, or from about 5 to about 7 nucleotides in length.

a barcode is from about 6 to about 25 nucleotides in length, from about 6 to about 24 nucleotides in length, from about 6 to about 23 nucleotides in length, from about 6 to about 22 nucleotides in length, from about 6 to about 21 nucleotides in length, from about 6 to about 20 nucleotides in length, from about 6 to about 19 nucleotides in length, from about 6 to about 18 nucleotides in length, from about 6 to about 17 nucleotides in length, from about 6 to about 16 nucleotides in length, from about 6 to about 15 nucleotides in length, from about 6 to about 14 nucleotides in length, from about 6 to about 13 nucleotides in length, from about 6 to about 12 nucleotides in length, from about 6 to about 11 nucleotides in length, from about 6 to about 10 nucleotides in length, from about 6 to about 9 nucleotides in length, from about 6 to about 8 nucleotides in length, or from about 3 to about 7 nucleotides in length.

Apparatus

Figure 11:
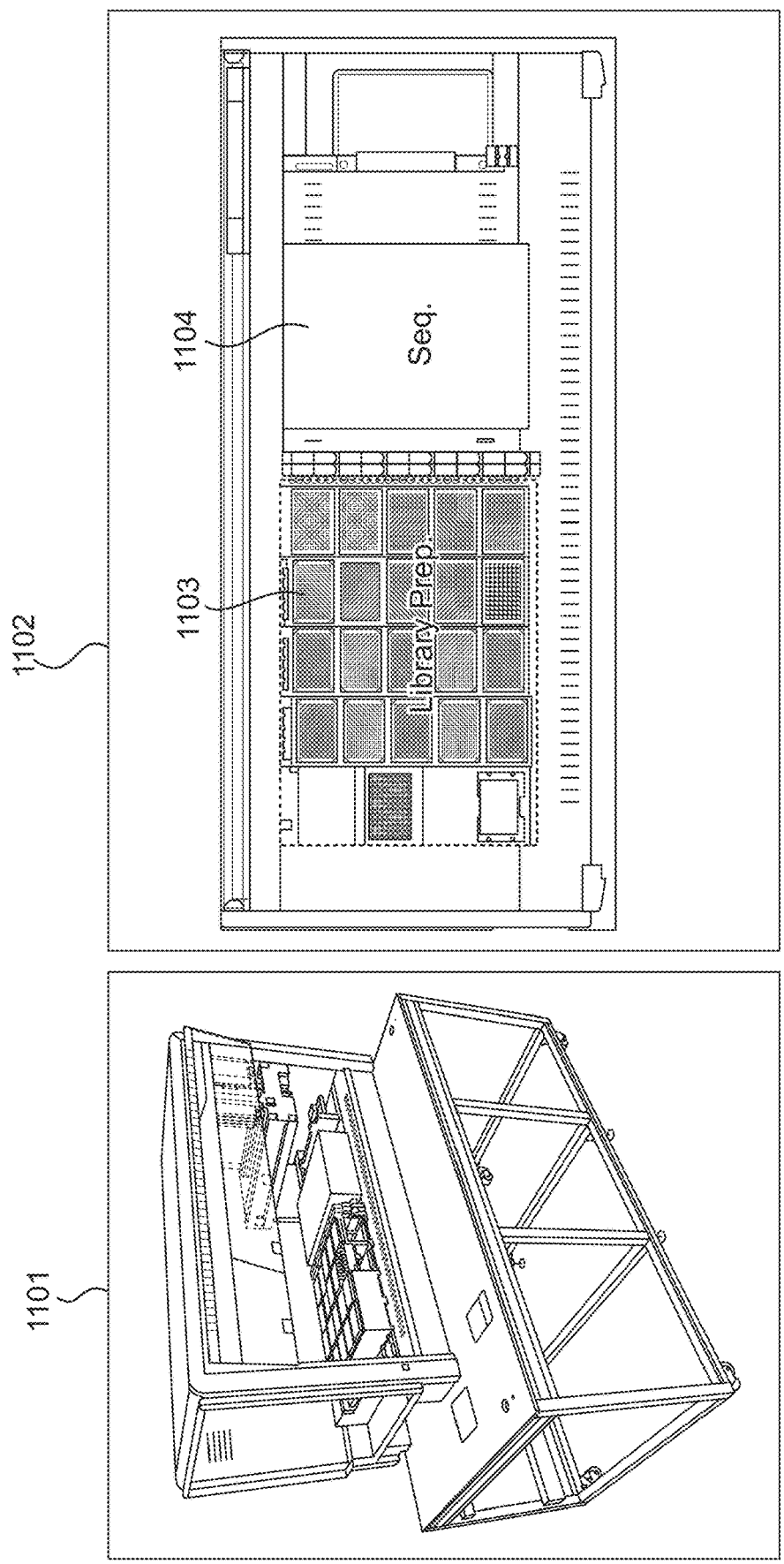
FIG. 11 illustrates an automated sequencing apparatus of the disclosure.
Figure 12:
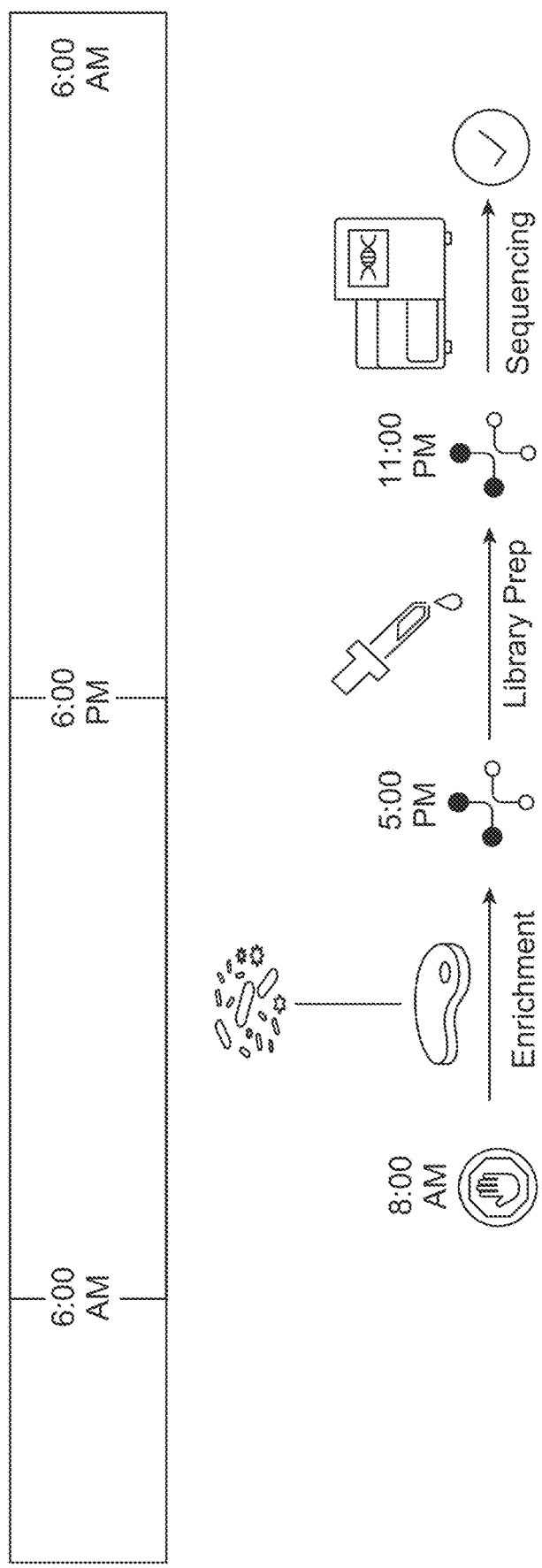
FIG. 12 illustrates a sequencing process with no human touch points after enrichment.

Automated nucleic acid sequencing apparatuses can provide a robust platform for the generation of nucleic acid sequencing reads. Unfortunately, many apparatuses have a high rate of failure, i.e., high rate of error of the sequencing reaction itself, which require manual intervention in such instances, such as re-loading of samples into flow cells. In some aspects, the disclosure provides an automated nucleic acid sequencing apparatus that requires no manual intervention in the event of a failure of a sequencing reaction. In some aspects, the disclosure provides a nucleic acid sequencing apparatus comprising: a nucleic acid library preparation compartment comprising two or more chambers configured to prepare a plurality of nucleic acids for a sequencing reaction, wherein said compartment is operatively connected to a nucleic acid sequencing chamber; a nucleic acid sequencing chamber, wherein said nucleic acid sequencing chamber comprises: (i) one or more flow cells comprising a plurality of pores configured for the passage of a nucleic acid strand, wherein said two or more flow cells are juxtaposed to one another; and an automated platform, wherein said automated platform is programmed to robotically move a sample from said nucleic acid library preparation compartment into said nucleic acid sequencing chamber. FIG. 11 illustrates an automated sequencing apparatus of the disclosure. 1101 is a diagram of the apparatus comprising the nucleic acid sequencing compartment 1102. Nucleic acid library preparation compartment 1103 shows a variety of chambers configured to prepare a plurality of nucleic acids for a sequencing reaction in close proximity to a sequencing chamber 1104, which comprises one or more flow cells. Briefly, an automated apparatus of the disclosure is programmed to move one or more samples from the library preparation chambers 1103 into a sequencing chamber 1104 upon detecting a failure in a sequencing reaction. This provides a sequencing process with no human touch points after a sample is added to the library preparation chamber, as illustrated in FIG. 12. FIG. 12 illustrates an embodiment where a sample from a food processing facility, from a hospital or clinical setting, or from another source can be manually processed between 6 am to 6 pm or any shorter or longer incubation window by incubating the sample in a presence of a growth medium (e.g., enrichment) and automatically processed after the sample is added to a nucleic acid preparation chamber 1103.

The disclosed apparatus is programmed in such a manner that said automated platform moves one or more samples from said nucleic acid library preparation compartment into said nucleic acid sequencing chamber. Upon detecting a failure of a sequencing reaction, the automated platform moves one or more samples from the failed sequencing flow cell or apparatus to the next sequencing flow cell or apparatus. In many cases, such samples comprise nucleic acid sequences that include one or more barcodes. In some cases, a plurality of mutually exclusive barcodes are added to a plurality of nucleic acids in said two or more chambers of the nucleic acid library preparation compartment 1103, thereby providing a plurality of mutually exclusive barcoded nucleic acids within the apparatus. In some instances, the automated platform robotically moves two or more of said mutually exclusive barcoded nucleic acids into said nucleic acid sequencing chamber, in some instances by moving said mutually exclusive barcoded nucleic acids into a same flow cell of said one or more flow cells.

The present disclosure describes an apparatus for the automated detection of food-borne pathogens via the sequencing of genomic libraries from samples introduced into the instrument. In some aspects, the apparatus may comprise four main components: library chambers for library preparation, fluid handling systems, sequencing flow cells, and automation systems. Within the scope of the present disclosure, there are numerous possible uses of the pathogen detection system.

Library Chambers

The present disclosure describes a device comprising one or more library chambers. Each library chamber may be capable of a broad range of functions including, but not limited to, sample preparation, sample enrichment, nucleic acid amplification, and purging. In some aspects, the library preparation may be performed entirely within a single library chamber. In other aspects, each library chamber may be reserved for a separate function in the library preparation process. Depending upon the processes necessary for library preparation, library chambers may be operatively connected to each other, and to one or more flow cells, or they may only have operative connections to a sequencing flow cell.

A library chamber may comprise one or more chambers and a securable hatch. The hatch allows access by a user or automated loading system for sample loading. The opening and closing mechanism of the hatch may be manual or electrically-actuated. In some aspects, a library chamber may comprise a main compartment and a secondary compartment for pre-loading a sample. Pre-loading may comprise a process of decontamination or other processes to prevent outside contaminants such as dust and pollen from entering the apparatus. Following decontamination, the specimen may be transferred into the main compartment. In other aspects, samples may be loaded into a single library chamber and the entire library chamber will be decontaminated.

The library chambers may be configured to accommodate a broad range of samples. When tracing the outbreak and spread of a food-borne pathogen, many possible sample types may be tested, including, but not limited to, soil samples, crop samples, tissue samples, cloth swabs, stool samples, and fluid samples. In some aspects, the present disclosure may provide a dynamic platform that is capable of enriching a detectable amount of nucleic acids from a sample. In some aspects, the library chamber may comprise a fixed unit of the apparatus described in the present enclosure and is capable of repeated reuse. In some aspects, a device of the disclosure comprises at least 5, at least 10, at least 15, at least 20, or another suitable number of library chambers 1103. In other aspects, the library chamber may comprise a cartridge for sample collection in the field. In such an embodiment, the library chamber would be loaded into the sequencing apparatus manually before the commencement of an automated library preparation and sequencing assay.

For the present disclosure, a library chamber may be configured in multiple ways depending upon how it will be utilized. A library chamber may comprise one or more inlet ports for the addition of reagents, gases, or any other necessary materials for library preparation. The inlet ports may be physically positioned at any portion of the library chamber depending upon the function of the inlet port. In some aspects, a library chamber may comprise one or more inlet ports. In some aspects, a library chamber may comprise 1 to 10 inlet ports, 2 to 10 inlet ports, 3 to 10 inlet ports, 4 to 10 inlet ports, 5 to 10 inlet ports, 6 to 10 inlet ports, 7 to 10 inlet ports, 8 to 10 inlet ports, or 9 to 10 inlet ports. In some aspects, an inlet port may be configured for the introduction of gases, liquids, or solids. In some aspects, an inlet port may be positioned near the top of the library chamber for uses such as the addition of liquid media. In other aspects, an inlet port may be positioned near the bottom of the library chamber for uses such as gas bubbling or sparging. A library chamber may also comprise one or more exit ports. In some aspects, a library chamber may comprise one or more exit ports. In some aspects, a library chamber may comprise 1 to 10 exit ports, 2 to 10 exit ports, 3 to 10 exit ports, 4 to 10 exit ports, 5 to 10 exit ports, 6 to 10 exit ports, 7 to 10 exit ports, 8 to 10 exit ports, or 9 to 10 exit ports. In some aspects, an exit port may be configured for the removal of gases, liquids, or solids.

The preparation of nucleic acid libraries may require the enrichment of a sample by culturing such samples in nutritious media that supports the enrichment of a sufficient amount of nucleic acids to perform a sequencing assay. In some aspects, the library chamber may serve to enrich a sample by serving as a cell-culturing chamber. In such a configuration, the library chamber may be filled with a cell-growth medium and any other reagents necessary to promote cell growth. In some aspects, the library chamber may be connected to modules of thermal regulation, including both heating and cooling, to promote optimal cell growth. The library chamber may be capable of aerobic or anaerobic operation. In some aspects, aerobic operation may comprise bubbling or sparging with oxygen or air. In other aspects, anaerobic operation may comprise bubbling or sparging the library chamber with a non-oxygenated gas including, but not limited to, nitrogen, helium, carbon dioxide or hydrogen. Mechanical agitation of cell culture may be necessary to prevent sedimentation of cells. In some aspects, agitation may be provided by sufficient bubbling of gases through the library chamber. In other aspects, a micro-impeller may provide mechanical mixing to the library chamber. In some aspects, a micro-impeller may comprise an impeller blade connected to a motor through a sealed bearing in a surface of the library chamber. In other aspects, a micro-impeller may comprise an impeller blade and shaft entirely contained within the library chamber. In such an embodiment, the impeller blade and shaft may comprise a magnetically-susceptible material such that the operation of an electromagnet in close proximity to the library surface may induce the spinning of the blade. In some aspects, a library chamber may be used to lyse cells as a method of freeing the nucleic acids contained within the cells. In some aspects, cell lysing and nucleic acid capture may be performed within one library chamber. In other aspects, cell lysing and nucleic acid capture may be performed in successive library chambers via a series of assays and material transfer between library chambers.

In some aspects, a library chamber in the present disclosure may comprise a DNA amplification and manipulation device. The library chamber may be a platform for any DNA amplification technique, including, but not limited to emulsion PCR. As a PCR platform, the library chamber may include a themocycler. The library chamber may also comprise a device for a variety of other DNA manipulation techniques including, but not limited to, restriction assays and ligation assays. In some aspects, the present disclosure may comprise a means to amplify a nucleic acid library. The library chamber may be used to fragment larger pieces of genomic DNA and add identifying sequences such as barcodes to nucleic acid fragments. All DNA manipulations may be performed in a single library chamber or multiple assays may be performed in one or more successive library chambers.

A library chamber may be comprised of a variety of materials depending upon the assays to be performed in it. The library may be comprised of materials such as metal, glass, ceramic or plastic. Library chambers may comprise metals that are non-magnetic, paramagnetic or ferromagnetic. In the present disclosure, library chambers may comprise metals such as aluminum, tungsten, tungsten oxide, austenitic stainless steel, or ferritic stainless steel. A library chamber may comprise a thermoplastic or a machinable plastic. The library chamber may comprise a plastic such as polyethylene, polypropylene, polyester, or polycarbonate. The chamber material may be chosen for a variety of properties including, but not limited to, biocompatibility, corrosion resistance, chemical reactivity, surface energy, electrical capacitance, electrical resistivity, electrical conductivity, magnetic properties, ductility, durability, elasticity, flexibility, hardness, malleability, mass density, tensile strength, surface roughness, machinability, light absorbance, light transmittance, index of refraction, light emissivity, thermal expansion, specific heat, and thermal conductivity. In some aspects, a library chamber may be composed of a single material that is acceptable for all intended uses. In other aspects, a library chamber may be composed of multiple materials, e.g. a glass chamber with metal inserts for connections to inlet and outlet ports. In some aspects, library chamber surfaces may comprise a chosen material with an applied coating. Such coatings may be used for a variety of purposes including, but not limited to, anti-corrosion, anti-friction, hydrophobicity, hydrophilicity, anti-agglomeration, anti-adsorption, pro-adsorption, anti-fouling, anti-static, chemical reactivity and chemical inertness. In the present disclosure, the library preparation portion of the apparatus may comprise multiple library chambers arranged in parallel or series configurations for a variety of purposes. In either case, each library chamber in the apparatus may comprise a different material design specifically chosen for the intended application of the library chamber.

Library chambers may be designed to include inline detection. The purpose of detection systems may include measuring system properties or detecting failed assays. Detection systems may be used to measure a variety of system properties, including, but not limited to, cell density, nucleic acid concentration, nucleic acid purity, pH, temperature, pressure, oxygen concentration, fluid density, fluid viscosity, dielectric constant, absorption spectrum, and heat capacity. In some aspects, a library chamber may include an optical port comprised of an optically-opaque material such as quartz glass. In some aspects, the transmittance, absorption, reflection or refraction of visible, infrared, microwave, or ultraviolet light sources may be measured using embedded optical ports. In some aspects, the library chambers may include mechanical ports for inserting measurement devices including, but not limited to pH probes, thermocouples, pressure gauges and dielectric probes. In some aspects, library chambers may be designed to allow fluid to be drawn out of fluid inlet or outlet ports for measurement at downstream instrumentation.

Fluid Handling Systems

In the present disclosure, fluid transfer may occur between one or more library chambers and one or more sequencing flow cells. The apparatus may comprise systems for ensuring the accurate transfer of fluids. Fluid transfer may also be involved in many other aspects of device operation, including, but not limited to cell culturing, cell lysis, nucleic acid purification, nucleic acid amplification, nucleic acid ligation, nucleic acid fragmentation, nucleic acid sequencing, sequence flow cell priming, chamber mixing, chamber cleaning, and chamber purging. The sequencing flow cell, as designed, must maintain a gas-free operational state for its entire life. In many embodiments of the present disclosure, the fluid handling system will be designed to ensure that no gas may be transferred from the library preparation system to the sequencing flow cell system.

Numerous fluids may be involved in the operation of the food-borne pathogen detection described in the present disclosure. Liquids used may include buffers, acids, bases, surfactants, emulsions, suspensions, chelating agents, and solutions. Liquids used may include, but are not limited to, deionized water, HCl, $H_2SO_4$, $HNO_3$, NaOH, KOH, NaCl, KCl, $CaCl_2$, $MgCl_2$, EDTA, ethanol, and methanol. Gases used may include inert gases, oxidizing gases and reducing gases. Gases used may include, but are not limited to $N_2$, air, $O_2$, He, Ar, $H_2$, and $CO_2$. Commonly used liquids may be stored in the device. In some aspects, liquids may be stored in onboard chambers. In other aspects, liquids may be stored in cartridges that can be added or removed manually or via an automated system. In some aspects, gases may be delivered via external tanks or plumbed lines via inlet ports in the apparatus.

Fluids may be moved through a food-borne pathogen detection apparatus by a variety of mechanisms. Fluid movement devices may include pumps, compressors, regulators, blowers, and fans. The apparatus in the present disclosure may comprise one or more pumps for liquid transfer. These pumps may be responsible for moving fluids into library chambers, emptying library chambers, transferring fluids from library chambers to sequencing flow cells, moving fluids through flow cells, preventing sedimentation of solids, clearing filters and draining waste fluids from the apparatus. Depending upon the specific applications, pumps included in the described apparatus may comprise positive-displacement pumps, peristaltic pumps, gear pumps, rotary pumps, screw pumps, piston pumps, or diaphragm pumps. Pumps and compressors may also be used for gas transfer. Regulators and compressors may be used to adjust gas pressures in the apparatus. Vacuum pumps may be used to void library chambers during purging operations. Fluid transfer may also be achieved via passive mechanisms such as gravity feeding and capillary action. A pathogen or a non-pathogenic microorganism detection device may comprise one or more valves for fluid control. Valves may be located in any flow line, including at inlet and exit ports for library chambers, at inlets and exits to the sequencing flow cells, and at inlet and drainage ports for the apparatus. Valves may be capable of manual control or automated control. Fluid transfer may be controlled by devices such as mass flow controllers and rotameters. Fluid transfer regulation may be achieved via manual controls on the apparatus, analog or digital electronic control systems on the apparatus, or via computer systems interfaced with a remote sequencing apparatus.

For the present disclosure, connectivity between device inlets, library chambers, sequencing flow cells, and drainage ports may be pursued. Connectivity may be achieved via direct coupling of components at otherwise sealed junctions or junctions that have movable openings. Connectivity between components may be achieved by any suitable method, including, but not limited to, mated flanges, compression fittings, friction fittings, hose barbs, and magnetic couplings. In some aspects, a seal may be needed between two connected components. Depending upon the design, a seal may need to be air-tight, leak-free, detachable, or permanent. A seal may comprise a gasket, O-ring, metal compression fitting or plastic compression fitting. Seals may be chosen from a variety of materials including, but not limited to polypropylene, polycarbonate, rubber, copper, or graphite. Connectivity may also comprise piping or tubing between system components. Piping or tubing may comprise any material suitable to the chosen application. Materials may be chosen to for properties including anti-fouling, anti-friction, hydrophobicity, hydrophilicity, durability, flexibility, strength, cost, and biocompatibility. Piping or tubing materials may include, but are not limited to, stainless steel tubing, copper tubing, aluminum tubing, brass tubing, rigid plastic tubing, or flexible plastic tubing. In some aspects, piping or tubing may be fitted permanently in the device. In other aspects, piping or tubing lines may be disposable.

Other devices may necessarily be part of the flow system for the device described in the present disclosure. In some aspects, various flow lines may be equipped with one or more filters. Filter may be for liquids or gases. Filters may be for various purposes including capturing cells or cellular components, maintaining sterility from outside fluid sources, capturing any particle contaminants, or any other debris that may need to be excluded from the library chambers or sequencing flow cells. In some aspects, one or more bubblers may be included at the junction between a library chamber and an external gas line. Bubblers may comprise a fritted metal, fritted glass or any other porous material that distributes flowing gas. In some aspects, a separation device may comprise a connection between units in the described apparatus. Separation devices may be used to perform ultrafiltration, adsorption, reverse osmosis, extraction, chromatography, sedimentation, sieving or vapor-liquid separation. In some aspects, a device may be placed between a library chamber and a sequencing flow cell to ensure the removal of all gas bubbles.

In some aspects, the sterility of the sequencing apparatus may be maintained to promote a higher efficiency operation or a sequencing that may be exposed to fewer contaminants. The internal and automated portions of the device may be enclosed within a sealed housing to prevent the intrusion of any airborne particles and debris such as dust, mold, mildew, pollen, bacteria, viruses and lint. The sealed housing may be purged of ambient air by use of a vacuum pump or may be held under positive pressure via an attached source of compressed gas. Certain external portions of the device may require frequent exposure to the outside environment, presenting potential sources of contamination, e.g. library chambers during sample insertion. Any external port, inlet or chamber may be held under positive pressure to minimize the chances of unwanted debris or biological entities depositing into the system during operation. Any and all chambers, cells and fluid transfer systems may undergo one or more washing, cleaning or purging processes to remove contaminants or residual matter from normal operations. Washing, cleaning or purging may comprise the use of detergents, surfactants, acids, bases, alcohols, deionized water, DNAses, RNAses, proteases, lipases, or any other cleansing method. Washing, cleaning or purging may involve heat treatments or vacuum evacuation. Any and all fluid transfer systems may comprise materials with anti-fouling or biocidal coatings or surface functionalization to minimize the deposition of contaminants, especially in regions with fluid stagnation. Fluid flow may be laminar to increase residence time in a portion of the apparatus, e.g. a prolonged cleansing step, or may be turbulent to decrease residence time or decrease mixing, e.g. rapid cell movement to reduce sedimentation.

Automation Systems

The food-borne pathogen detection apparatus described in the present disclosure is intended for autonomous or semi-autonomous operation. In some aspects, the apparatus may only require manual intervention for the input of samples and reagents, and all further operations may be handled via an automated software/hardware system. In other aspects, the apparatus may require manual input of information, instructions or physical materials, such as reagents, at particular times in the instrument's operations. The device may operate using customized algorithms for each operation or may utilize standard algorithms. Algorithms may be manually input via onboard control systems or sent from a remote computer system. The device may be hardwired to an external computer system or communicate wirelessly. The sequencing apparatus may be capable of exporting data in packets or transmitting data in real-time as sequencing is performed. In some aspects, the apparatus will automatically detect failed operations including, but not limited to, failed bacterial enrichment, failed DNA amplification or purification, and failed sequencing. In some aspects, the system may include diagnostic or analytical devices at inlet or exit ports, in library chambers, or in any flow line to provide data on the status of ongoing operations.

The apparatus in the present disclosure may operate via electrical supply from an external power supply, e.g. a wall outlet, or run via a self-contained battery system. Field portable versions of the device may be intended to run in conjunction with portable power systems such as solar panels or portable generators. In some aspects, the apparatus will comprise all necessary electrical components to accept either DC or AC power, as the power supply source dictates.

The sequencing device may utilize robotics for automated operation. In some aspects, robotics may be responsible for any and all internal operations, including, but not limited to moving fluids, opening and closing valves, adding reagents, performing cleaning operations, performing and monitoring bacterial growth operations, performing and monitoring DNA amplification and purification operations, performing sequencing assays, priming or reconditioning flow cells, and discharging waste from the apparatus. In some aspects, all components of a sequencing device may be fixed in their positions, with robotics used primarily to control the movement of liquids, gases and other materials through the system. In other aspects, robotics may be used to move library chambers to a point of direct connectivity with another portion of the system, e.g. a sequencing flow cell.

In some aspects, fluid transfer operations may be mediated by one or more automated pipette systems. In some aspects, a pipette system may comprise a single pipette. In other aspects, a pipette system may comprise an array of pipettes arranged in multiplexed fashion. One or more pipettes may be capable of dispensing fluids via positive pressure-driven flow or removing fluids via a negative pressure differential (vacuum). In some aspects, one or more pipettes may be configured to dispense or withdraw fluids individually. In other aspects, one or more pipettes may be configured to dispense or withdraw fluids simultaneously. Fluids may be dispensed or withdrawn in a continuous or metered fashion. In some aspects, a metered pipette may dispense or withdraw fluid volumes of about 0.1 µl to about 1000 µl. In some aspects a metered pipette may dispense or withdraw fluid volumes of about 0.1 µl to 10 µl, 0.1 µl to 20 µl, 0.1 µl to 30 µl, 0.1 µl to 40 µl, 0.1 µl to 50 µl, 0.1 µl to 60 µl, 0.1 µl to 70 µl, 0.1 µl to 80 µl, 0.1 µl to 90 µl, 0.1 µl to 100 µl, 1 µl to 10 µl, 1 µl to 20 µl, 1 µl to 30 µl, 1 µl to 40 µl, 1 µl, to 50 µl, 1 µl to 60 µl, 1 µl to 70 µl, 1 µl to 80 µl, 1 µl to 90 µl, 1 µl to 100 µl, 10 µl to 20 µl, 10 µl to 30 µl, 10 µl to 40 µl, 10 µl to 50 µl, 10 µl to 60 µl, 10 µl to 70 µl, 10 µl to 80 µl, 10 µl to 90 µl, 10 µl to 100 µl, 10 µl to 200 µl, 10 µl to 300 µl, 10 µl to 400 µl, 10 µl to 500 µl, 10 µl to 1000 µl, 100 µl to 200 µl, 100 µl to 300 µl, 100 µl to 400 µl, 100 µl to 500 µl, 100 µl to 1000 µl, 250 µl to 500 µl, or about 250 µl to 1000 µl. In some aspects, each pipette may comprise a separate pressure actuator. In other aspects, two or more pipettes may be controlled by the same pressure actuator. Pipette tips may be permanent or disposable. In some aspects, disposable pipette tips may comprise a hollow plastic piece that mates to a permanent surface. Disposable pipette tips may be secured to the permanent surface via downward pressure on the permanent surface onto the plastic. An automated fluid transfer system may comprise an automated method for removing disposable pipette tips.

An array of pipettes with pressure actuators or connectivity to pressure actuators may be mounted on an automated translation stage capable of movement in one or more dimensions. In some aspects, an automated translation stage may be capable of 3-dimensional movement. In some aspects, an automated translation stage may be capable of rotational movement. In some aspects, an automated translation system may be coupled to one or more motors, pneumatic devices, or any other method of producing linear motion. Translation may be produced in continuous or incremented, step-wise fashion. Translational movements may be produced on the order of about 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 5 mm, 10 mm, 20 mm, 30 mm, 40 mm, 50 mm, 100 mm, 200 mm, 300 mm, 400 mm, 500 mm, 600 mm, 700 mm, 800 mm, 900 mm, or 1000 mm.

Automated Priming and Library Loading Device

Figure 25:
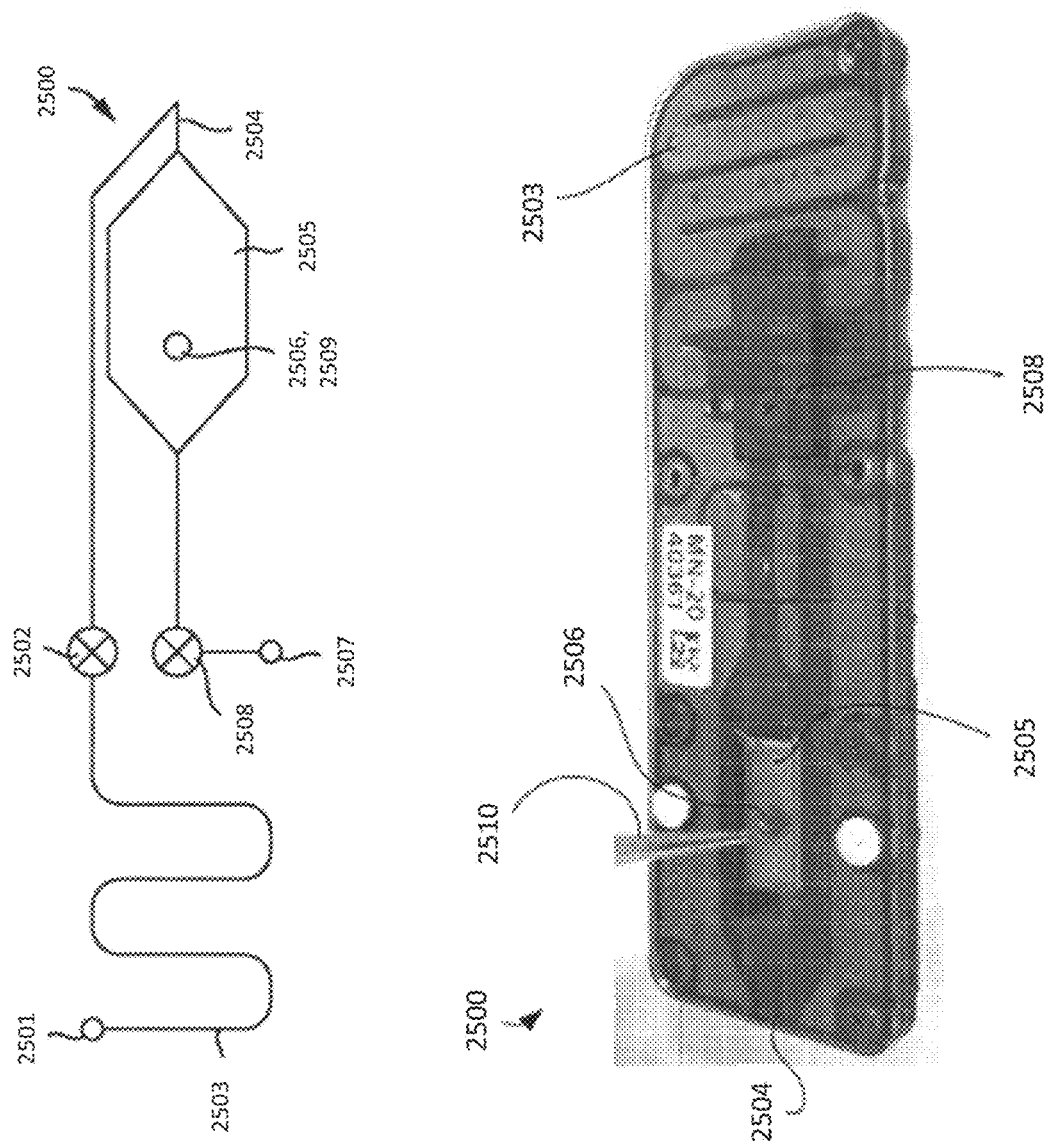
FIG. 25 illustrates an exemplary automatable nanopore flow cell suitable for use with the methods according to this disclosure.

Oxford Nanopore flow cells have a flow path as shown in FIG. 25, (which depicts a schematic cross-section along the flow path, top, and the corresponding features on a picture of a flow cell, bottom) and are pre-filled with a conditioning liquid to protect the nanopore membrane during storage. Further description of such flow cells can be found e.g., in WO2018007819A1. However, the commercial form of the oxford nanopore flow cell (e.g. GridIONx5™ cell) is not provided in a form where all the preparation steps for sequencing can be performed by an automated process. Particularly, all steps of storage buffer replacement and priming of liquid flow through the flow cell are difficult to automate because of a flat plastic removable seal that covers the sample input port (the presence and absence of which is demonstrated in FIG. 14 and FIG. 15 which cannot be conveniently removed by automated processes.

The nanopore flow cell device comprises a sensor provided in a sensing chamber (2505); a flow path comprising a sensing chamber inlet (2509) and a sensing chamber outlet (2504) connecting to the sensing chamber for respectively passing liquid into and out of the sensing chamber, and a sample input port (2506) in fluid communication with the inlet; and a liquid collection channel (2503) downstream of the outlet. The device additionally has a flow path interruption (2502, e.g. a valve activated by an actuatable lever accessible from the top surface of the device) between the sensing chamber outlet (2501) and the liquid collection channel (2503), preventing liquid from flowing into the liquid collection channel (2503) from upstream, and the device may be activated by completing the flow path between the sample input port (2506) and the liquid collection channel (2503), such as by opening a valve when a valve is in place of the flow path interruption (2502). When provided by the manufacturer as a new flow cell, conditioning liquid fills from the sample input port (2506) to the flow path interruption (2502) such that the sensor (within 2505) is covered by liquid and is unexposed to a gas or gas/liquid interface. The device additionally has a buffer input port (2507) in fluid communication with the sensing chamber inlet (2509), a flow path interruption (2502, e.g. a valve activated by an actuatable lever accessible from the top surface of the device, which is the same as the valve controlling the flow between the sensing chamber outlet and the liquid collection channel), and a flat plastic removable plug covering the sample input port (2506).

Before use, the conditioning liquid filling the flow cell must be replaced by priming buffer suitable for operation of the device, but buffer must be introduced in such a way that it does not allow the sensor in the sensing chamber (2505) to come in contact with bubbles or gas/liquid interface, which damage the sensor. Thus, the normal method for buffer replacement involves the removal of the flow path obstruction(s) (2506), also known as activation (which allows liquid to flow through the device), followed by buffer introduction into the buffer input port (2507), which displaces the conditioning liquid within the device. The flat plastic plug is then removed from the input port (2506), and priming buffer is applied via the input port so there is a continuous fluid channel from the input port (2506) through the sensing chamber outlet (2501) that is ready to receive sample. Because there is a continuous fluid channel from the input port (2506) through the sensing chamber outlet (2501), application of one or more volumes of test liquid to the wet surface of the input port provides a net driving for sufficient to introduce the one or more volumes of test liquid into the device and displace buffer liquid into the liquid collection channel (2503), allowing normal operation of the device (e.g. flow of nucleic acids within the test liquid through the sensor chamber).

Because the flow path interruptions (2506) are provided as a valve with a horizontally-actuatable lever on the surface of the device, opening of the valve during the priming process can be automated e.g. via a robotic arm. The removal of the flat sample input port plug is difficult to automate.

Figure 26:
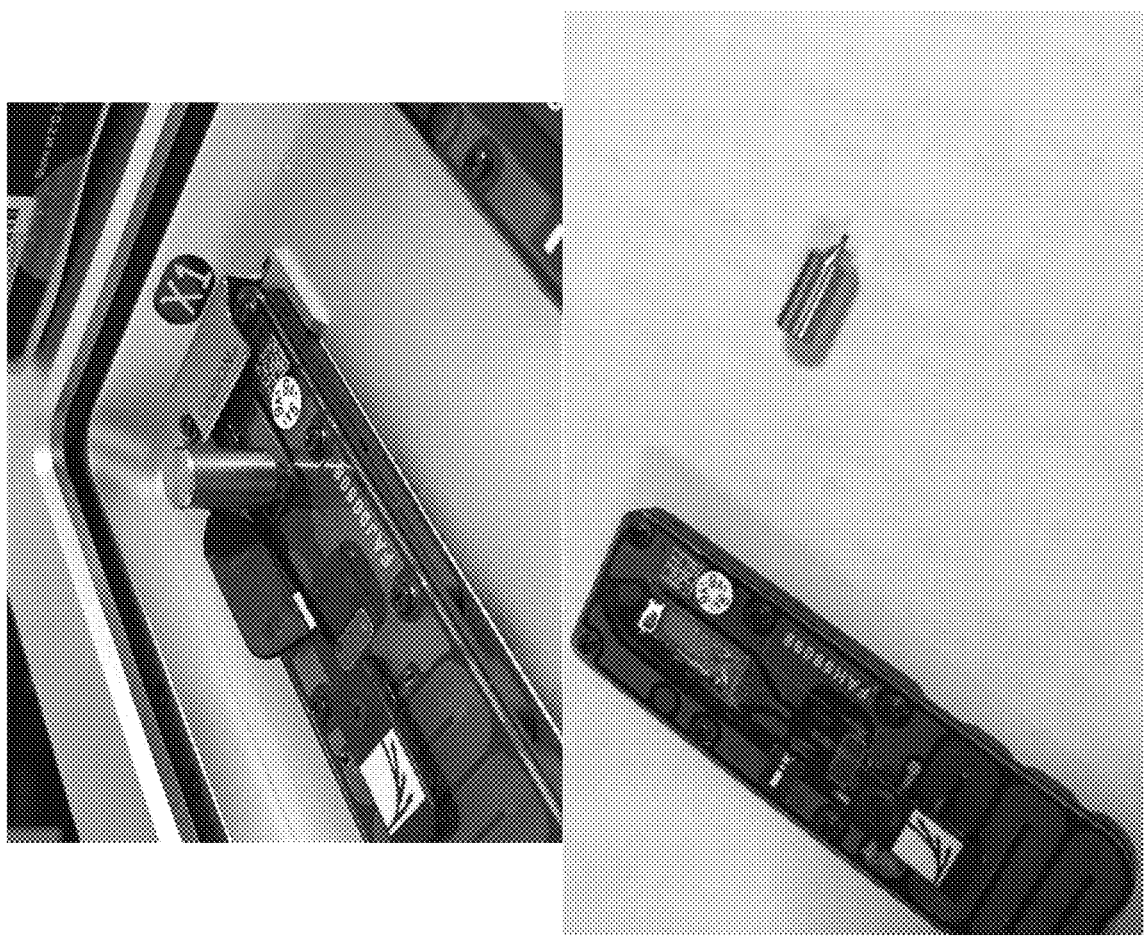
FIG. 26 illustrates an exemplary automatable nanopore flow cell with an alternative sample input port plug as described herein.

Replacement of the flat sample input port plug with an alternative plug that is amenable to robotic removal, however, allows the opening of the sample input port to be opened during an automated process. In an example, the alternative plug is cylindrical, consisting of a first flat end and a second conical tapered end, wherein the conical tapered end tapers to a size sufficient to completely fill and obstruct the sample input port. Such a cylindrical plug will project a sufficient distance (e.g. 1-3 cm, or 1.0, 1.5, 2.0, 2.5, or 3 cm) above the surface of the flow cell when used to plug the sample input port via its tapered end so that it can be conveniently removed by a robotic arm without touching the surface of the flow cell. Such an exemplary alternative plug is depicted in FIG. 26. In some instances, the alternative plug is a shape that is not cylindrical (e.g. rectangular, square, triangular), but which projects at least a sufficient distance (e.g. 1-3 cm, or 1.0, 1.5, 2.0, 2.5, or 3 cm) above the surface of the flow cell when used to plug the sample input port that it can be removed without disturbing the surface of the flow cell and at least tapers to a size sufficient to plug the sample input port. In some embodiments, the alternative plug is constructed of a ferromagnetic material such as ferritic stainless steel, so that handling (placement and/or removal) of the plug can be accomplished with an electromagnet. In some embodiments, the alternative plug comprises a metallic material. In some embodiments, the alternative plug comprises tungsten, aluminum, austenic stainless steel, ferritic stainless steel, or another material that is resistant to dilute nitric acid ($HNO_3$), 1M NaOH, or dilute NaOCl for removal of RNA/DNA/RNAse contamination. In some embodiments, the alternative plug comprises polypropylene or polycarbonate.

The automated removal of the alternative plug can be incorporated into the process of Example 13 to accomplish fully automated nanopore pore cell priming and sample loading of one or multiple flow cells simultaneously. An exemplary automated process involving the use of such an alternative plug described above involves first replacing the flat plastic sample input plug port (the "SpotON" plug depicted in FIG. 14) with an embodiment of the alternative plug described above (e.g. manually). The flow path interruptions/valves (2506) of the flow cell are opened, and the device is placed inside an automated sequencing apparatus as described above, in Example 13, or in FIG. 13. In some embodiments, the flow path interruptions/valves (2506) of the flow cell are opened via an automated process after the flow cell has been manually placed in the automated sequencing apparatus. The automated sequencing apparatus then provides priming buffer to the buffer input port (2506), such as the buffers described in Example 13, and after conditioning buffer in the flow cell has been displaced, the alternative plug is removed (e.g. by a robotic arm) and sample is provided to the sample input port via the automated sequencing apparatus. The sequencing process then proceeds as otherwise described in Example 13 with automated handling and fluid addition. In some embodiments, the alternative plug is replaced after the sequencing run is completed so that the flow cell can be flushed and re-primed for at least an additional run. In this way, the nanopore flow cells can be repeatedly re-primed and reused e.g. for running additional samples on the same flow cell, or for running repeats of samples where the flow sequencing has failed, data recording has failed, or the PCR amplification of nucleic acids derived from the food or environmental sample have failed. In some embodiments, the flow cells in the automated sequencing apparatus are re-primed and reused at least several times (e.g. at least 2, 3, 4, 5, 6, 7, 8, 9 or 10 times). Importantly, the alternative plug provides a way of re-priming the cell on-demand without manual intervention. This is particularly important in the case of sequencing/amplification/data transmission failure, as it enables automated repeating of sample runs after hours or at other times/locations where the automated sequencing apparatus is unattended.

Configurations and Methods of Operation

Described herein are methods for operating an automated sequencing apparatus for food-borne pathogen detection. Such a system may be comprised in numerous fashions. In some aspects, the apparatus may comprise a fixed device with minimal moving parts. In other aspects, the device may comprise a dynamic, robotic system with numerous moving parts.

Regardless of configuration, a sequencing operation may comprise the steps of sample loading, library generation, library transfer, sequencing and data communication. Each step may comprise numerous embodiments. The methods described herein are exemplary and do not constrain the possible mode of operation for any embodiment of the food-borne pathogen detection system.

Sample loading may comprise any process for the emplacement of a specimen in a library chamber. In some aspects, a specimen may be manually placed into the library chamber. In other aspects a sample may be loaded by an automated system. In some aspects, samples may be captured in cartridges that can be loaded into the library chamber by an automated sample handling system. Sample loading may comprise processes for decontaminating library chambers of environmental contaminants from the loading process.

Library generation may comprise a sequence of assays and methods depending upon the methodology of library generation. Assays may include cell culture, cell lysis, DNA amplification, DNA purification, washings, extractions, purifications, dilutions, concentrations, buffer exchanges, restriction assays, barcoding, and any other biochemical method necessary to generate a DNA library. In some aspects, a single library chamber may be utilized for all processing steps. In other aspects, a sample may be relayed between multiple chambers for each processing step with emptied library chambers undergoing wash procedures to remove excess reagents.

Sequencing of the DNA library may occur in one or more flow cells. A DNA library may be distributed into multiple libraries to speed the processing of a sample. Sequencing may comprise the real-time transmission of data or staged transmission of packets of data. Data processing may occur in one or more onboard processors in the sequencing apparatus, or may occur at a remote terminal.

Although many details of the operation may be found in all embodiments of the food-borne pathogen detection system, there may be numerous methods of configuring the system to achieve the desired level of performance and accuracy within an allowable footprint. The configuration may be motivated in response to the application of the system. In some aspects, the sequencing apparatus may be field-portable for rapid deployment in difficult environments such as farm fields or restaurant kitchens. Such a device may have a limited footprint with room for few library chambers or sequencing flow cells. In other aspects, the device may comprise a lab-scale fixture with an effectively unconstrained footprint. Such an instrument may comprise hundreds to thousands of library chambers and sequencing flow cells with a robotic system for sample management. Described below are several exemplary embodiments of apparatus configurations. Other embodiments are possible within the scope this disclosure.

Static Operation

A food-borne pathogen detection apparatus may comprise a fixed or static device. In such a configuration, the library chambers may be positioned permanently relative to the sequencing flow cells. Connectivity between library chambers may comprise a system of tubing, pumps and valves. The fluid flow system would be capable of performing all necessary fluid transfer operations during operation without manual intervention. In some aspects, one or more library chambers may comprise a sequencing apparatus. The library chambers may be arranged in a serial or parallel fashion.

A sequencing apparatus may comprise a single library chamber and one or more sequencing flow cells. In some aspects, the connection between the library chamber and sequencing cell may comprise a flow line and one or more valves. Such an embodiment may comprise the simplest device with the most compact footprint.

Two or more library chambers arranged in parallel fashion may comprise a sequencing apparatus. In some aspects, a plurality of library chambers may have connectivity with a single flow cell. In other aspects, each library may be connected to a single flow cell. In some aspects, parallel operation of library chambers may comprise performing all aspects of sample preparation and library generation within a single library chamber. Following library generation, nucleic acid from a library chamber may be transferred to one or more sequencing flow cells. Multiple flow cells may be used for a single DNA library to speed the sequencing process.

Two or more chambers may also be arranged in a serial fashion. A serial operation may comprise a staged operation with each library chamber specialized to perform a specific operation within the device methodology. A serial arrangement of library chambers may comprise a larger footprint than a system comprising a single library chamber or parallel library chambers. A serial arrangement of chambers may comprise a more complicated flow system with additional valves and pumps needed to actuate all necessary fluid transfer steps. A serial configuration may offer more efficient operation because each library chamber is designed specifically for its function.

Conveyer Operation

In some aspects, a food-borne pathogen detection apparatus may comprise a series of two or more library chambers on a conveyer system. The conveyer may comprise a linear or circular system. A sequencing apparatus may comprise one or more conveyer systems. Each conveyer unit may couple to one or more sequencing flow cells. The purpose of the conveyer system is to move a library chamber into connectivity with a sequencing cell when the nucleic acid library has been prepared. Each library chamber on the conveyer system may have connectivity with the necessary components to carry out library preparation procedures. When library preparation is completed, the library chamber may be moved into position by the conveyer and coupled to the sequencing flow cell. Upon completion of fluid transfer from the library chamber to the sequencing cell, the conveyer may move the completed library chamber and out and replace the flow cell plug or place a new library chamber in connectivity with the flow cell. In some aspects, the conveyer system comprises a circular conveyer with four library chambers and two flow cells mounted along an axis. In this configuration, two library chambers have connectivity to flow cells while two library chambers conduct library preparation procedures. When new libraries are ready for sequencing, the conveyer may rotate 90° to connect the new library chambers, while the previously-sequenced chambers being new library preparations.

Compartment Operation

A compartment-style sequencing apparatus may comprise a system of hundreds or thousands of library chambers in a large-footprint device. In some aspects, a library chamber may comprise a cartridge that is loaded with a specimen external to the sequencing apparatus. The cartridge may be transferred into the apparatus and then moved to a docking station comprising one or more connective ports by a plurality of robotic conveyances. The docking ports may provide all necessary fluid transfer operations to complete library preparation within the library chamber. When library preparation is complete, the cartridge may be transferred to an available sequencing flow cell by a plurality of robotic conveyances. In some aspects, a cartridge-style library chamber may be simultaneously connected to fluid transfer ports and a sequencing flow cell to create a semi-robotic system with a reduced footprint.

FIG. 11 illustrates a compartmentalized automated sequencing apparatus of the disclosure with a desktop footprint. 1101 is a diagram of the apparatus comprising the nucleic acid sequencing compartment 1102. Nucleic acid library preparation compartment 1103 shows a variety of chambers configured to prepare a plurality of nucleic acids for a sequencing reaction in close proximity to a sequencing chamber 1104, which comprises one or more flow cells. Briefly, an automated apparatus of the disclosure is programmed to move one or more samples from the library preparation chambers 1103 into a sequencing chamber 1104 upon detecting a failure in a sequencing reaction. This provides a sequencing process with no human touch points after a sample is added to the library preparation chamber, as illustrated in FIG. 12. FIG. 12 illustrates an embodiment where a sample from a food processing facility, from a hospital or clinical setting, or from another source can be manually processed between 6 am to 6 pm or any shorter or longer incubation window by incubating the sample in a presence of a growth medium (e.g., enrichment) and automatically processed after the sample is added to a nucleic acid preparation chamber 1103.

The disclosed apparatus is programmed in such a manner that said automated platform moves one or more samples from said nucleic acid library preparation compartment into said nucleic acid sequencing chamber. Upon detecting a failure of a sequencing reaction, the automated platform moves one or more samples from the failed sequencing flow cell or apparatus to the next sequencing flow cell or apparatus. In many cases, such samples comprise nucleic acid sequences that include one or more barcodes. In some cases, a plurality of mutually exclusive barcodes are added to a plurality of nucleic acids in said two or more chambers of the nucleic acid library preparation compartment 1103, thereby providing a plurality of mutually exclusive barcoded nucleic acids within the apparatus. In some instances, the automated platform robotically moves two or more of said mutually exclusive barcoded nucleic acids into said nucleic acid sequencing chamber, in some instances by moving said mutually exclusive barcoded nucleic acids into a same flow cell of said one or more flow cells.

Classification

Microbiome data (data representing the presence or absence of particular species or serotypes of microbes as determined by sequencing) of the invention can be used to classify a sample. For example, a sample can be classified as, or predicted to be: a) containing a particular pathogenic microbe, b) containing a particular serotype of a pathogenic microbe, and/or c) contaminated with at least one species/serotype of pathogenic microbe. Many statistical classification techniques are known to those of skill in the art. In supervised learning approaches, a group of samples from two or more groups (e.g. contaminated with a pathogen and not) are analyzed with a statistical classification method. Microbe presence/absence data can be used as a classifier that differentiates between the two or more groups. A new sample can then be analyzed so that the classifier can associate the new sample with one of the two or more groups. Commonly used supervised classifiers include without limitation the neural network (multi-layer perceptron), support vector machines, k-nearest neighbours, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with the invention include quadratic classifiers, k-nearest neighbor, boosting, decision trees, random forests, neural networks, pattern recognition, Bayesian networks and Hidden Markov models. One of skill will appreciate that these or other classifiers, including improvements of any of these, are contemplated within the scope of the invention.

Classification using supervised methods is generally performed by the following methodology:

In order to solve a given problem of supervised learning (e.g. learning to recognize handwriting) one has to consider various steps:

1. Gather a training set. These can include, for example, samples that are from a food or environment contaminated or not contaminated with a particular microbe, samples that are contaminated with different serotypes of the same microbe, samples that are or are not contaminated with a combination of different species and serotypes of microbes, etc. The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output. The features might include a set of bacterial species or serotypes present in a food or environmental sample derived as described herein.

3. Determine the structure of the learned function and corresponding learning algorithm. A learning algorithm is chosen, e.g., artificial neural networks, decision trees, Bayes classifiers or support vector machines. The learning algorithm is used to build the classifier.

4. Build the classifier (e.g. classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the classifier (e.g. classification model) is determined as described above, it can be used to classify a sample, e.g., that of food sample or environment that is being analyzed by the methods of the invention.

Unsupervised learning approaches can also be used with the invention. Clustering is an unsupervised learning approach wherein a clustering algorithm correlates a series of samples without the use the labels. The most similar samples are sorted into "clusters." A new sample could be sorted into a cluster and thereby classified with other members that it most closely associates.

Digital Processing Device

In some aspects, the disclosed provides quality control methods or methods to assess a risk associated with a food, with a hospital, with a clinic, or any other location where the presence of a bacterium poses a certain risk to one or more subjects. In many instances, systems, platforms, software, networks, and methods described herein include a digital processing device, or use of the same. In further embodiments, the digital processing device includes one or more hardware central processing units (CPUs), i.e., processors that carry out the device's functions, such as the automated sequencing apparatus disclosed herein or a computer system used in the analyses of a plurality of nucleic acid sequencing reads from samples derived from a food processing facility or from any other facility, such as a hospital a clinical or another. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In other embodiments, the digital processing device could be deployed on premise or remotely deployed in the cloud.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. In many aspects, the disclosure contemplates any suitable digital processing device that can either be deployed to a food processing facility, or is used within said food processing facility to process and analyze a variety of nucleic acids from a variety of samples.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280× about 720 pixels or at least about 1920× about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In many aspects, the systems, platforms, software, networks, and methods disclosed herein include one or more non-transitory computer readable storage media encoded with a program including instructions executable by the operating system of an optionally networked digital processing device. For instance, in some aspects, the methods comprise creating data files associated with a plurality of sequencing reads from a plurality of samples associated with a food processing facility. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EMBODIMENTS

Embodiment 1

An embodiment comprising: (a) deploying an assay to one or more food processing facilities; (b) performing a sequencing reaction of a food sample or of an environmental sample from said one or more food processing facilities; (c) transmitting an electronic communication comprising a data set associated with said sequencing reaction of said food sample or of said environmental sample from said one or more food processing facilities to a server; and (d) scanning, by a computer, at least a fraction of said transmitted data set for one or more genes associated with a microorganism.

Embodiment 2

The method of embodiment 1, wherein said scanning scans fewer than 0.001%, 0.01%, 0.1%, 1% of said transmitted data set for one or more genes associated with said microorganism.

Embodiment 3

The method of embodiment 1, wherein said sequencing reaction is a pore sequencing reaction, a next generation sequencing reaction, a shotgun next generation sequencing, or Sanger sequencing.

Embodiment 4

The method of embodiment 3, wherein said sequencing reaction is a pore sequencing reaction.

Embodiment 5

The method of embodiment 4, wherein said pore sequencing reaction distinguishes an epigenetic pattern on a nucleic acid from said food sample or from said environmental sample.

Embodiment 6

The method of embodiment 5, wherein said epigenetic pattern is a methylation pattern.

Embodiment 7

The method of embodiment 1, wherein said microorganism is pre-selected by a customer.

Embodiment 8

The method of embodiment 1, further comprising scanning, by a computer, at least a fraction of said transmitted data set for one or more genes associated with two or more microorganisms.

Embodiment 9

The method of embodiment 1, wherein said microorganism is selected from the group consisting of: a microorganism of the *Salmonella* genus, a microorganism of the *Campylobacter* genus, a microorganism of the *Listeria* genus, and a microorganism of the *Escherichia* genus.

Embodiment 10

The method of embodiment 1, wherein said food sample is a perishable.

Embodiment 11

The method of embodiment 10, wherein said perishable is a meat.

Embodiment 12

The method of embodiment 11, wherein said meat is a poultry, a red meat, a fish, or a swine.

Embodiment 13

The method of embodiment 8, wherein said perishable is a fruit, an egg, a vegetable, a produce or a legume.

Embodiment 14

The method of embodiment 1, wherein said environmental sample is a surface swab or a surface rinse of said one or more food processing facilities.

Embodiment 15

The method of embodiment 1, wherein said environmental sample is a food storage container, a food handling equipment from said one or more food processing facilities, or a piece of clothing from a worker of said one or more food processing facilities.

Embodiment 16

The method of embodiment 1, further comprising amplifying or enriching one or more nucleic acids of said food sample or of said environmental sample prior to performing said sequencing reaction.

Embodiment 17

The method of embodiment 1, further comprising adding at least one barcode to one or more nucleic acids of said food sample or of said environmental sample prior to performing said sequencing reaction.

Embodiment 18

The method of embodiment 17, further comprising creating, in a computer, a data file that associates said at least one barcode with a source of said food sample or of said environmental sample.

Embodiment 19

The method of embodiment 17, further comprising adding a plurality of mutually exclusive barcodes to a plurality of food processing facilities.

Embodiment 20

The method of embodiment 1, wherein said scanning comprises scanning said transmitted data set for one or more polymorphic gene regions.

Embodiment 21

The method of embodiment 20, wherein said one or more polymorphic regions comprise one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements.

Embodiment 22

The method of embodiment 20, wherein said one or more polymorphic regions comprise one or more single nucleotide polymorphisms (SNP's).

Embodiment 23

The method of embodiment 1, wherein said sequencing reaction differentiates a live microorganism from a dead microorganism.

Embodiment 24

The method of embodiment 1, wherein said sequencing reaction differentiates a resident microorganism as compared to a transient microorganism.

Embodiment 25

The method of embodiment 1, wherein said method distinguishes a microorganism from an *Escherichia* genus from a microorganism of a *Citrobacter* genus or a Shiga-Toxin producing *E. coli* (STEC) from a non-STEC *E. coli*.

Embodiment 26

An embodiment comprising: (a) deploying an assay to one or more food processing facilities; (b) performing a sequencing reaction of a food sample or of an environmental sample from said one or more food processing facilities; (c) transmitting an electronic communication comprising a data set associated with said sequencing reaction of said food sample or of said environmental sample from said one or more food processing facilities to a server; and (d) scanning, by a computer, at least a fraction of said transmitted data set for one or more genes associated with a microorganism. Copy language of issued claim

Embodiment 27

An embodiment comprising: (a) deploying an assay to one or more food processing facilities; (b) performing a sequencing reaction of a food sample or of an environmental sample from said one or more food processing facilities, wherein said sample comprises a target nucleic acid comprising a periodic or a non-periodic barcode; (c) transmitting an electronic communication comprising a data set associated with said sequencing reaction of said food sample or of said environmental sample from said one or more food processing facilities to a server; and (d) scanning, by a computer, at least a fraction of said transmitted data set for one or more genes associated with a microorganism, wherein said fraction is in comparison to a data set of a substantially complete sequencing reaction, wherein said fraction of said transmitted data set comprises a number of sequencing reads or a number of sequenced nucleotide bases.

Embodiment 28

An embodiment comprising: (a) obtaining a plurality of nucleic acid sequences from a sample; (b) scanning, by a computer, at least a fraction of said plurality of said nucleic acid sequences for a plurality of nucleic acid regions from one or more microorganisms selected from the group consisting of: a microorganism of the *Salmonella* genus, a microorganism of the *Campylobacter* genus, a microorganism of the *Listeria* genus, and a microorganism of the *Escherichia* genus, wherein said scanning characterizes said one or more microorganisms with greater than 99.5% sensitivity.

Embodiment 29

The method of embodiment 28, wherein said sample is a food sample or an environmental sample associated with said food sample.

Embodiment 30

The method of embodiment 28, wherein said sample is a non-food sample.

Embodiment 31

The method of embodiment 28, wherein said sample comprises blood, plasma, urine, tissue, faces, bone marrow, saliva or cerebrospinal fluid.

Embodiment 32

The method of embodiment 28, wherein said scanning characterizes said one or more microorganisms with greater than 99% sensitivity.

Embodiment 33

The method of embodiment 32, wherein said scanning characterizes said one or more microorganisms with greater than 99.9%, 99.99%, or 99.999% sensitivity.

Embodiment 34

The method of embodiment 33, wherein said scanning characterizes said one or more microorganisms with greater than 99.5% specificity.

Embodiment 35

The method of embodiment 34, wherein said scanning characterizes said one or more microorganisms with greater than 99% specificity.

Embodiment 36

The method of embodiment 35, wherein said scanning characterizes said one or more microorganisms with greater than 99.9%, 99.99%, or 99.999% specificity.

Embodiment 37

The method of embodiment 28, wherein said scanning characterizes said one or more microorganisms with greater than 99.5% sensitivity and greater than 99% specificity.

Embodiment 38

The method of embodiment 28, wherein a scanning of no more than 0.001%, 0.01%, 0.1%, or 1% of nucleic acid regions within said plurality of nucleic acid sequences characterizes said one or more microorganisms with greater than 99.5% sensitivity.

Embodiment 39

The method of embodiment 38, wherein a scanning of no more than 0.001%, 0.01%, 0.1%, or 1% of nucleic acid regions within said plurality of nucleic acid sequences characterizes said one or more microorganisms with greater than 99.9% sensitivity.

Embodiment 40

The method of embodiment 28, wherein a scanning of no more than 0.001%, 0.01%, 0.1%, or 1% of nucleic acid regions within said plurality of nucleic acid sequences characterizes said one or more microorganisms with greater than 99.5% specificity.

Embodiment 41

The method of embodiment 40, wherein a scanning of no more than 0.001%, 0.01%, 0.1%, or 1% of nucleic acid regions within said plurality of nucleic acid sequences characterizes said one or more microorganisms with greater than 99.9% specificity.

Embodiment 42

The method of embodiment 41, wherein said method has fewer than 0.1% of a false positive identification rate.

Embodiment 43

The method of embodiment 28, wherein said plurality of nucleic acid sequences comprise complementary DNA (cDNA) sequences.

Embodiment 44

The method of embodiment 28, wherein said plurality of nucleic acid sequences comprise ribonucleic acid (RNA) sequences.

Embodiment 45

The method of embodiment 28, wherein said plurality of nucleic acid sequences comprise genomic deoxyribonucleic acid (gDNA) sequences.

Embodiment 46

The method of embodiment 28, wherein said plurality of nucleic acid sequences comprise a mixture of cDNA, RNA, and gDNA sequences.

Embodiment 47

The method of embodiment 28, wherein said scanning comprises scanning said plurality of said nucleic acid sequences for one or more polymorphic gene regions associated with said microorganisms.

Embodiment 48

The method of embodiment 47, wherein said one or more polymorphic regions comprise a gene coding region associated with said microorganisms.

Embodiment 49

The method of embodiment 47, wherein said one or more polymorphic regions comprise a regulatory region associated with said microorganisms.

Embodiment 50

The method of embodiment 47, wherein said one or more polymorphic regions is selected from the group consisting of one or more single nucleotide polymorphisms (SNPs), one or more restriction fragment length polymorphisms (RFLPs), one or more short tandem repeats (STRs), one or more variable number of tandem repeats (VNTRs), one or more hypervariable regions, one or more minisatellites, one or more dinucleotide repeats, one or more trinucleotide repeats, one or more tetranucleotide repeats, one or more simple sequence repeats, one or more insertion elements, or one or more epigenetic modifications.

Embodiment 51

The method of embodiment 28, wherein said obtaining of said plurality of nucleic acid sequences comprises sequencing or hybridizing said plurality of nucleic acid sequences.

Embodiment 52

The method of embodiment 51, wherein said sequencing reaction is a pore sequencing reaction, a next generation sequencing reaction, a shotgun next generation sequencing, or Sanger sequencing.

Embodiment 53

The method of embodiment 52, wherein said sequencing reaction is a pore sequencing reaction.

Embodiment 54

The method of embodiment 53, wherein said pore sequencing reaction distinguishes an epigenetic pattern on a nucleic acid from said food sample or from said environmental sample.

Embodiment 55

The method of embodiment 54, wherein said epigenetic pattern is a methylation pattern.

Embodiment 56

The method of embodiment 28, wherein said microorganism of the *Salmonella* genus has a serotype selected from the group consisting of: Enteritidis, Typhimurium, Newport, Javiana, Infantis, Montevideo, Heidelberg, Muenchen, Saintpaul, Oranienburg, Braenderup, Paratyphi B var. L(+) Tartrate+, Agona, Thompson, and Kentucky.

Embodiment 57

The method of embodiment 56, wherein said microorganism of the *Salmonella* genus is of the serotype Enteritidis.

Embodiment 58

The method of embodiment 56, wherein said microorganism of the *Salmonella* genus is of the serotype Typhimurium.

Embodiment 59

The method of embodiment 56, wherein said microorganism of the *Salmonella* genus is of the serotype Newport.

Embodiment 60

The method of embodiment 56, wherein said microorganism of the *Salmonella* genus is of the serotype Javiana.

Embodiment 61

The method of embodiment 56, wherein said microorganism of the *Escherichia* genus has a serotype selected from the group consisting of: O103, O111, O121, O145, O26, O45, and O157.

Embodiment 62

The method of embodiment 61, wherein said microorganism of the *Escherichia* genus is *E. coli* O157:H7.

Embodiment 63

The method of embodiment 28, wherein said scanning distinguishes said microorganism of the *Escherichia* genus from a microorganism of the *Citrobacter* genus.

Embodiment 64

The method of embodiment 28, wherein said microorganism of the *Listeria* genus has a serotype selected from the group consisting of: 2a, 1/2b, 1/2c, 3a, 3b, 3c, 4a, 4b, 4ab, 4c, 4d, and 4e.

Embodiment 65

The method of embodiment 28, wherein said microorganism of the *Campylobacter* genus is *C. jejuni. C. lari*, and *C. coli*.

Embodiment 66

An embodiment comprising: (a) sequencing a plurality of nucleic acid sequences from a food sample or from an environmental sample associated with said food sample for a period of time; and (b) performing an assay on said food sample or said environment associated with said food sample if said sequencing for said period of time identifies a threshold level of nucleic acid sequences from a microorganism in said food sample.

Embodiment 67

The method of embodiment 66, wherein said period of time is less than 30 minutes.

Embodiment 68

The method of embodiment 66, wherein said period of time is less than 20 minutes.

Embodiment 69

The method of embodiment 66, wherein said threshold is no more than 0.001%, 0.01%, 0.1%, or 1%, of nucleic acid sequences from said microorganism.

Embodiment 70

The method of embodiment 66, further comprising performing an amplification reaction on said plurality of nucleic acid sequences prior to sequencing.

Embodiment 71

The method of embodiment 66, wherein said sequencing is a pore sequencing reaction.

Embodiment 72

The method of embodiment 66, wherein said assay is a serotyping assay, a culturing assay, a Pulse Field Gel Electrophoresis (PFGE) assay, a RiboPrinter® assay, a q-PCR assay, a Sanger sequencing assay, an ELISA assay, a Whole Genome Sequencing (WGS) assay, a targeted sequencing assay, or a shotgun metagenomics assay.

Embodiment 73

The method of embodiment 66, wherein said microorganism is selected from the group consisting of: a microorganism of the *Salmonella* genus, a microorganism of the *Campylobacter* genus, a microorganism of the *Listeria* genus, and a microorganism of the *Escherichia* genus.

Embodiment 74

The method of embodiment 73, wherein said microorganism of the *Salmonella* genus has a serotype selected from the group consisting of: Enteritidis, Typhimurium, Newport, Javiana, Infantis, Montevideo, Heidelberg, Muenchen, Saintpaul, Oranienburg, Braenderup, Paratyphi B var. L(+) Tartrate+, Agona, Thompson, and Kentucky.

Embodiment 75

The method of embodiment 73, wherein said microorganism of the *Escherichia* genus has a serotype selected from the group consisting of: O103, O111, O121, O145, O26, O45, and O157.

Embodiment 76

The method of embodiment 73, wherein said microorganism of the *Escherichia* genus is *E. coli* O157:H7.

Embodiment 77

The method of embodiment 73, wherein said microorganism of the *Listeria* genus has a serotype selected from the group consisting of: 2a, 1/2b, 1/2c, 3a, 3b, 3c, 4a, 4b, 4ab, 4c, 4d, and 4e.

Embodiment 78

The method of embodiment 73, wherein said microorganism of the *Campylobacter* genus is *C. jejunis, C. lari*, or *C. coli*.

Embodiment 79

The method of embodiment 66, wherein said plurality of nucleic acid sequences comprise complementary DNA (cDNA) sequences.

Embodiment 80

The method of embodiment 66, wherein said plurality of nucleic acid sequences comprise ribonucleic acid (RNA) sequences.

Embodiment 81

The method of embodiment 66, wherein said plurality of nucleic acid sequences comprise genomic deoxyribonucleic acid (gDNA) sequences.

Embodiment 82

The method of embodiment 66, wherein said plurality of nucleic acid sequences comprise a mixture of cDNA, RNA, and gDNA sequences.

Embodiment 83

The method of embodiment 66, wherein said food sample is a perishable.

Embodiment 84

The method of embodiment 83, wherein said perishable is a meat.

Embodiment 85

The method of embodiment 84, wherein said meat is a poultry, a red meat, a fish, or a swine.

Embodiment 86

The method of embodiment 83, wherein said perishable is a fruit, an egg, a vegetable, a produce or a legume.

Embodiment 87

The method of embodiment 66, wherein said environmental sample is a surface swab or a surface rinse of said environment.

Embodiment 88

The method of embodiment 66, wherein said environmental sample is a food storage container, a food handling equipment, or a piece of clothing from a worker of said environment associated with said food sample.

Embodiment 89

An embodiment comprising: (a) obtaining a first plurality of nucleic acid sequences from a first sample of a food processing facility; (b) creating a data file in a computer that associates one or more of said first plurality of nucleic acid sequences with said food processing facility; (c) obtaining a second plurality of nucleic acid sequences from a second sample of said food processing facility; and (d) scanning a plurality of sequences from said second plurality of nucleic acid sequences for one or more sequences associated with said food processing facility in (b).

Embodiment 90

The method of embodiment 89, wherein said data file associates a strain of said microorganism with said food processing facility.

Embodiment 91

The method of embodiment 89, wherein said first sample, said second sample, or both comprises a plurality of sequences from a plurality of microorganisms.

Embodiment 92

The method of embodiment 89, wherein at least one of said plurality of microorganisms is a non-pathogenic microorganism.

Embodiment 93

The method of embodiment 89, wherein at least one of said plurality of microorganisms is a pathogenic microorganism.

Embodiment 94

The method of embodiment 93, wherein said pathogenic microorganism is selected from the group consisting of a gram-negative bacteria, a gram-positive bacteria, a protozoa, a viruses, and a fungi.

Embodiment 95

The method of embodiment 94, wherein said gram-negative bacteria is a *Salmonella* bacterium.

Embodiment 96

The method of embodiment 94, wherein said gram-negative bacteria is an *Escherichia* bacterium.

Embodiment 97

The method of embodiment 94, wherein said gram-positive bacteria is a *Listeria* bacterium.

Embodiment 98

The method of embodiment 94, wherein said gram-negative bacteria is a *Campylobacter* bacterium.

Embodiment 99

The method of embodiment 89, further comprising obtaining a third plurality of nucleic acid sequences from an additional sample of said food processing facility.

Embodiment 100

The method of embodiment 89, wherein said first sample, said second sample, or both is a perishable.

Embodiment 101

The method of embodiment 100, wherein said perishable is a meat.

Embodiment 102

The method of embodiment 100, wherein said meat is a poultry, a red meat, a fish, or a swine.

Embodiment 103

The method of embodiment 101, wherein said perishable item is a fruit, an egg, a vegetable, a produce or a legume.

Embodiment 104

The method of embodiment 89, wherein said first sample, said second sample, or both is a surface swab or a surface rinse of said environment.

Embodiment 105

The method of embodiment 89, wherein said first sample, said second sample, or both is a food storage container, a food handling equipment, or a piece of clothing from a worker of said environment associated with said food sample.

Embodiment 106

The method of embodiment 89, wherein at least one barcode is added to said first plurality of nucleic acid sequences, said second plurality of nucleic acid sequences or both.

Embodiment 107

The method of embodiment 106, wherein said at least one barcode is associated with said data file of (b), thereby associating said at least one barcode with said food processing facility.

Embodiment 108

The method of embodiment 89, wherein obtaining said first plurality of nucleic acid sequences, said second plurality of nucleic acid sequences, or both comprises performing a sequencing reaction or a hybridization assay.

Embodiment 109

The method of embodiment 105, wherein said sequencing reaction is a pore sequencing reaction, a next generation sequencing reaction, a shotgun next generation sequencing, or Sanger sequencing.

Embodiment 110

The method of embodiment 109, wherein said sequencing reaction is a pore sequencing reaction.

Embodiment 111

The method of embodiment 110, wherein said pore sequencing reaction distinguishes an epigenetic pattern on a nucleic acid from said food sample or from said environmental sample.

Embodiment 112

The method of embodiment 110, wherein said epigenetic pattern is a methylation pattern.

Embodiment 113

An embodiment comprising: (a) obtaining a first sample of a food processing facility; (b) sequencing said first sample of said food processing facility, thereby generating a first set of sequencing data from said food processing facility; (c) obtaining a second sample of said food processing facility; (d) sequencing said second sample of said food processing facility, thereby generating a second set of sequencing data from said food processing facility; and (e) comparing said second set of sequencing data to said first set of sequencing data; and (d) decontaminating said food processing facility if said comparing identifies a pathogenic microorganism in said food processing facility.

Embodiment 114

An embodiment comprising (a) obtaining a first plurality of nucleic acid sequences from a first sample of a food processing facility; (b) obtaining a second plurality of nucleic acid sequences from a second food sample of said food processing facility; and (c) performing sequence alignments in a computer between said first plurality of nucleic acid sequences and said second plurality of nucleic acid sequences thereby determining a similarity between said first sample and said second sample from said food processing facility.

Embodiment 115

An embodiment comprising: (a) adding a reagent to a plurality of nucleic acid molecules from a food sample or from an environmental sample associated with said food sample, thereby forming a modified plurality of nucleic acid molecules, whereby said reagent (i) modifies a structure of or interacts with a plurality of nucleic acid molecules derived from one or more dead microorganisms; and (ii) does not modify a structure of a nucleic acid molecule derived from one or more live microorganisms; thereby providing a modified plurality of nucleic acid molecules; and (b) sequencing by a sequencing reaction said modified plurality of nucleic acid molecules, thereby distinguishing one or more live organisms from said food sample or from said environmental sample associated with said food sample.

Embodiment 116

The method of embodiment 113, wherein said sequencing reaction comprises pore sequencing.

Embodiment 117

The method of embodiment 113, wherein said food sample is stressed, shocked or processed prior to adding said reagent to said plurality of nucleic acid molecules.

Embodiment 118

The method of embodiment 113, further comprising incubating said food sample in a growth medium prior to performing said sequencing reaction.

Embodiment 119

The method of embodiment 113, wherein said reagent is a photoreactive DNA-binding dye.

Embodiment 120

The method of embodiment 119, wherein said photoreactive DNA-binding dye is propidium monoazide or a derivative thereof.

Embodiment 121

The method of embodiment 113, wherein said reagent is a DNA intercalating reagent.

Embodiment 122

The method of embodiment 113, further comprising performing an amplification reaction prior to sequencing said modified plurality of nucleic acid molecules.

Embodiment 123

The method of embodiment 113, wherein said food sample is a perishable.

Embodiment 124

The method of embodiment 123, wherein said perishable is a meat.

Embodiment 125

The method of embodiment 124, wherein said meat is a poultry, a red meat, a fish, or a swine.

Embodiment 126

The method of embodiment 123, wherein said perishable is a fruit, an egg, a vegetable, or a legume.

Embodiment 127

The method of embodiment 115, wherein said environmental sample is a surface swab or a surface rinse of said environment.

Embodiment 128

The method of embodiment 115, wherein said environmental sample is a food storage container, a food handling equipment, or a piece of clothing from a worker of said environment associated with said food sample.

Embodiment 129

An embodiment comprising performing a pore sequencing reaction on a plurality of nucleic acid molecules from a food sample or from an environmental sample associated with said food sample, whereby said pore sequencing reaction distinguishes one or more nucleic acid molecules derived from a dead microorganism from one or more nucleic acid molecules derived from a live microorganism based on a methylation pattern or another epigenetic pattern of said one or more nucleic acid molecules derived from said dead microorganism.

Embodiment 130

The method of embodiment 129, wherein said pore sequencing reaction is a nanopore sequencing reaction.

Embodiment 131

A method comprising: (a) obtaining a plurality of nucleic acid sequences of a food sample or of an environmental sample from a food processing facility; (b) performing a first assay in said plurality of nucleic acid sequences of said food sample, whereby said assay predicts a presence or predicts an absence of a microorganism in said food sample; and (c) determining, based on said predicted presence or said predicted absence of said microorganism of (b) whether to perform a second assay, whereby a sensitivity of said second assay is selected to determine a genus, a species, a serotype, a sub-serotype, or a strain of said microorganism.

Embodiment 132

The method of embodiment 131, wherein said first assay and said second assay are identical.

Embodiment 133

The method of embodiment 131, wherein said first assay and said second assay have distinct sensitivities.

Embodiment 134

The method of embodiment 131, wherein said first assay, said second assay or both comprise a sequencing assay.

Embodiment 135

The method of embodiment 134, wherein said sequencing assay comprises a pore sequencing reaction, a next generation sequencing reaction, a shotgun next generation sequencing, or Sanger sequencing.

Embodiment 136

The method of embodiment 134, wherein said sequencing reaction is a pore sequencing reaction.

Embodiment 137

The method of embodiment 134, wherein said pore sequencing reaction distinguishes an epigenetic pattern on a nucleic acid from said food sample or from said environmental sample.

Embodiment 138

The method of embodiment 137, wherein said epigenetic pattern is a methylation pattern.

Embodiment 139

The method of embodiment 131, wherein said first assay, said second assay, or both comprise a polymerase chain reaction (PCR) assay.

Embodiment 140

The method of embodiment 131, wherein said first assay, said second assay, or both comprise an enzyme-linked immunosorbent (ELISA) assay.

Embodiment 141

The method of embodiment 131, wherein said first assay, said second assay, or both comprise an enzyme-linked fluorescent assay (ELFA) assay.

Embodiment 142

The method of embodiment 131, wherein said first assay, said second assay, or both comprise a serotyping assay.

Embodiment 143

The method of embodiment 131, wherein said microorganism is selected from the group consisting of: a microorganism of the *Salmonella* genus, a microorganism of the *Campylobacter* genus, a microorganism of the *Listeria* genus, a microorganism of the *Escherichia* genus, a virus, a parasite, and a fungi.

Embodiment 144

The method of embodiment 131, wherein said food sample is a perishable.

Embodiment 145

The method of embodiment 144, wherein said perishable is a meat.

Embodiment 146

The method of embodiment 145, wherein said meat is a poultry, a red meat, a fish, or a swine.

Embodiment 147

The method of embodiment 144, wherein said perishable is a fruit, an egg, a vegetable, a produce or a legume.

Embodiment 148

The method of embodiment 144, wherein said environmental sample is a surface swab or a surface rinse of said environment.

Embodiment 149

The method of embodiment 144, wherein said environmental sample is a food storage container, a food handling equipment, or a piece of clothing from a worker of said environment associated with said food processing facility.

Embodiment 150

The method of embodiment 131, wherein said performing of said first assay and said performing of said second assay predicts said presence or predicts said absence of said microorganism with greater than 90%, 95%, 98%, 99%, 99.9%, 99.99% or greater than 99.999% sensitivity.

Embodiment 151

An embodiment comprising: (a) detecting a presence or an absence of a non-pathogenic microorganism in a sample; (b) predicting, by a computer system, a presence or an absence of a pathogenic microorganism in said sample based on said presence or said absence of said non-pathogenic microorganism.

Embodiment 152

The method of embodiment 151, wherein said predicting is performed by a machine learning algorithm in a computer.

Embodiment 153

The method of embodiment 152, wherein said machine learning algorithm is selected from the group consisting of: a support vector machine (SVM), a Naïve Bayes classification, a random forest, Logistic Regression, and a neural network.

Embodiment 154

The method of embodiment 152, wherein said sample is a food sample or an environmental sample associated with said food sample.

Embodiment 155

The method of embodiment 154, wherein said food sample is a perishable.

Embodiment 156

The method of embodiment 155, wherein said perishable is a meat.

Embodiment 157

The method of embodiment 156, wherein said meat is a poultry, a red meat, a fish, or a swine.

Embodiment 158

The method of embodiment 155, wherein said perishable is a fruit, an egg, a vegetable, a produce, or a legume.

Embodiment 159

The method of embodiment 154, wherein said environmental sample is a surface swab or a surface rinse of said environment.

Embodiment 160

The method of embodiment 154, wherein said environmental sample is a food storage container, a food handling equipment, or a piece of clothing from a worker of said environment associated with said food processing facility.

Embodiment 161

The method of embodiment 151, wherein said sample is a non-food sample.

Embodiment 162

The method of embodiment 151, wherein said sample comprises blood, plasma, urine, tissue, faces, bone marrow, saliva or cerebrospinal fluid.

Embodiment 163

The method of embodiment 151, wherein said non-pathogenic microorganism.

Embodiment 164

The method of embodiment 151, wherein said non-pathogenic microorganism is selected from the group consisting of: *Enterobacter asburiae, Enterobacter bugandensis, Enterobacter cancerogenus, Enterobacter cloacae, Enterobacter endosymbiont, Enterobacter hormaechei, Enterobacter kobei, Enterobacter ludwigii, Enterobacter mori*, and *Enterobacter soli*.

Embodiment 165

The method of embodiment 151, wherein said pathogenic microorganism is selected from the group consisting of: a microorganism of the *Salmonella* genus, a microorganism of the *Campylobacter* genus, a microorganism of the *Listeria* genus, and a microorganism of the *Escherichia* genus.

Embodiment 166

The method of embodiment 151, wherein said pathogenic microorganism is selected from the group consisting of *Vibrio parahaemolyticus, Vibrio cholera, Vibrio vulnificus, Escherichia coli, Salmonella enterica, Shigella boydii, Campylobacter jejuni, Staphylococcus aureus, Listeria monocytogenes, Clostridium botulinum, Yersinia pseudotuberculosis, Clostridium perfringens, Yersinia enterocolitica, Coxiella burnetii, Yersinia pseudotuberculosis, Vibrio parahaemolyticus, Bacillus cereus, Mycobacterium tuberculosis, Shigella flexneri, Shigella boydii, Shigella dysenteriae*, and *Shigella sonnei*.

Embodiment 167

The method of embodiment 151, wherein said detecting comprises a nucleic acid characterization assay selected from the group consisting of a pore sequencing reaction, a next generation sequencing reaction, a shotgun next generation sequencing, Sanger sequencing, or hybridization assay.

Embodiment 168

The method of embodiment 167, wherein said nucleic acid characterization assay is a pore sequencing reaction.

Embodiment 169

The method of embodiment 168, wherein said pore sequencing reaction distinguishes an epigenetic pattern on a nucleic acid from said food sample or from said environmental sample.

Embodiment 170

The method of embodiment 151, further comprising performing an assay to confirm the prediction of (b).

Embodiment 171

The method of embodiment 170, wherein said assay is a serotyping reaction.

Embodiment 172

The method of embodiment 170, wherein said assay is a polymerase chain reaction (PCR) assay.

Embodiment 173

The method of embodiment 172, wherein said assay is an enzyme-linked immunosorbent (ELISA) assay.

Embodiment 174

The method of embodiment 172, wherein said assay is an enzyme-linked fluorescent assay (ELFA) assay.

Embodiment 175

An embodiment comprising: (a) detecting a presence or an absence of a microorganism in a sample or in a facility associated with said sample; and (b) predicting, by a computer system, a risk presented by said facility based on said presence or said absence of said microorganism.

Embodiment 176

The method of embodiment 175, wherein said sample is a food sample or an environmental sample associated with said food sample.

Embodiment 177

The method of embodiment 176, wherein said food sample is a perishable.

Embodiment 178

The method of embodiment 177, wherein said perishable is a meat.

Embodiment 179

The method of embodiment 178, wherein said meat is a poultry, a red meat, a fish, or a swine.

Embodiment 180

The method of embodiment 177, wherein said perishable is a fruit, an egg, a vegetable, a produce, or a legume.

Embodiment 181

The method of embodiment 176, wherein said environmental sample is a surface swab or a surface rinse of said environment.

Embodiment 182

The method of embodiment 176, wherein said environmental sample is a food storage container, a food handling equipment, or a piece of clothing from a worker of said environment associated with said food processing facility.

Embodiment 183

The method of embodiment 175, wherein said sample is a non-food sample.

Embodiment 184

The method of embodiment 175, wherein said sample comprises blood, plasma, urine, tissue, faces, bone marrow, saliva or cerebrospinal fluid.

Embodiment 185

The method of embodiment 175, wherein said facility is a food processing facility.

Embodiment 186

The method of embodiment 175, wherein said facility is a hospital or a clinic.

Embodiment 187

The method of embodiment 175, wherein said method predicts said presence or said absence of said microorganism with greater than 90%, 95%, 98%, 99%, 99.9%, 99.99% or 99.999% sensitivity.

Embodiment 188

The method of embodiment 175, wherein said method predicts said presence or said absence of said microorganism with greater than 90%, 95%, 98%, 99%, 99.9%, 99.99% or 99.999% specificity.

Embodiment 189

The method of embodiment 175, wherein said risk informs an insurance for said facility.

Embodiment 190

The method of embodiment 175, wherein said microorganism is a pathogenic or a non-pathogenic microorganism.

Embodiment 191

The method of embodiment 175, wherein said detecting comprises a sequencing reaction or a hybridization assay.

Embodiment 192

The method of embodiment 191, wherein said sequencing reaction is selected from the group consisting of a pore sequencing reaction, a next generation sequencing reaction, a shotgun next generation sequencing, Sanger sequencing.

Embodiment 193

The method of embodiment 192, wherein said sequencing reaction is a pore sequencing reaction.

Embodiment 194

The method of embodiment 193, wherein said pore sequencing reaction distinguishes an epigenetic pattern on a nucleic acid from said food sample or from said environmental sample.

Embodiment 195

The method of embodiment 175, further comprising performing an assay to confirm the prediction of (b).

Embodiment 196

The method of embodiment 195, wherein said assay is a serotyping reaction.

Embodiment 197

The method of embodiment 195, wherein said assay is a polymerase chain reaction (PCR) assay.

Embodiment 198

The method of embodiment 195, wherein said assay is an enzyme-linked immunosorbent (ELISA) assay.

Embodiment 199

The method of embodiment 195, wherein said assay is an enzyme-linked fluorescent assay (ELFA) assay.

Embodiment 200

An embodiment comprising: (a) adding a first barcode to a first plurality of nucleic acid sequences from a sample, thereby providing a first plurality of barcoded nucleic acid sequences; and (b) performing a first sequencing reaction on said first plurality of barcoded nucleic acid sequences, wherein said sequencing reaction is performed on a sequencing apparatus comprising a flow cell; (c) adding a second barcode to a second plurality of nucleic acid sequences from a second sample, thereby providing a second plurality of barcoded nucleic acid sequences; and (d) performing a second sequencing reaction on said second plurality of barcoded nucleic acid sequences, wherein said second sequencing reaction is performed on said sequencing apparatus comprising said flow cell, thereby reusing said flow cell.

Embodiment 201

The method of embodiment 200, wherein said first barcode and said second barcode are between 1 nucleotide and 18 nucleotides in length.

Embodiment 202

The method of embodiment 200, wherein said first barcode and said second barcode are about 9 nucleotides in length.

Embodiment 203

The method of embodiment 200, wherein said first barcode and said second barcode have identical sequences.

Embodiment 204

The method of embodiment 200, wherein said first barcode and said second barcode have distinct sequences.

Embodiment 205

The method of embodiment 200, further comprising adding a third barcode to a third plurality of nucleic acid sequences from a third food sample or from a third environmental sample associated with said third food sample, thereby providing a third plurality of barcoded nucleic acid sequences.

Embodiment 206

The method of embodiment 205, further comprising performing a third sequencing reaction on said third plurality of barcoded nucleic acid sequences, wherein said third sequencing reaction is performed on said sequencing apparatus comprising said flow cell, thereby reusing said flow cell for a third time.

Embodiment 207

The method of embodiment 200, wherein said first barcode, said second barcode, and said third barcode have identical sequences.

Embodiment 208

The method of embodiment 200, wherein said first barcode, said second barcode, and said third barcode have distinct sequences.

Embodiment 209

The method of embodiment 200, further comprising performing an amplification reaction or nucleic acid enrichment on said plurality of nucleic acid sequences prior to sequencing of (b), (d), or both.

Embodiment 210

The method of embodiment 200, wherein said sequencing is selected from the group consisting of a pore sequencing reaction, a next generation sequencing reaction, a shotgun next generation sequencing, or Sanger sequencing.

Embodiment 211

The method of embodiment 200, wherein said sequencing reaction is a pore sequencing reaction.

Embodiment 212

The method of embodiment 211, wherein said pore sequencing reaction distinguishes an epigenetic pattern on a nucleic acid from said food sample or from said environmental sample.

Embodiment 213

The method of embodiment 211, wherein said epigenetic pattern is a methylation pattern.

Embodiment 214

The method of embodiment 200, wherein said plurality of nucleic acid sequences comprise complementary DNA (cDNA) sequences.

Embodiment 215

The method of embodiment 200, wherein said plurality of nucleic acid sequences comprise ribonucleic acid (RNA) sequences.

Embodiment 216

The method of embodiment 200, wherein said plurality of nucleic acid sequences comprise genomic deoxyribonucleic acid (gDNA) sequences.

Embodiment 217

The method of embodiment 200, wherein said plurality of nucleic acid sequences comprise a mixture of cDNA, RNA, and gDNA sequences.

Embodiment 218

The method of embodiment 200, wherein said first sample is a first food sample or a first environmental sample associated with said first food sample.

Embodiment 219

The method of embodiment 200, wherein said second sample is a second food sample or a second environmental sample associated with said first food sample.

Embodiment 220

The method of embodiments 218 or 219, wherein said first food sample, said second food sample, or both are a perishable.

Embodiment 221

The method of embodiment 220, wherein said perishable is a meat.

Embodiment 222

The method of embodiment 221, wherein said meat is a poultry, a red meat, a fish, or a swine.

Embodiment 223

The method of embodiment 221, wherein said perishable is a fruit, an egg, a vegetable, a produce or a legume.

Embodiment 224

The method of embodiments 218 or 219, wherein said first environmental sample, said second environmental sample, or both is a surface swab or a surface rinse of said environment.

Embodiment 225

The method of embodiments 218 or 219, wherein said first environmental sample, said second environmental sample, or both is a food storage container, a food handling equipment, or a piece of clothing from a worker of said environment associated with said food processing facility.

Embodiment 226

The method of embodiment 200, wherein said sample is a non-food sample.

Embodiment 227

The method of embodiment 226, wherein said sample comprises blood, plasma, urine, tissue, feces, bone marrow, saliva or cerebrospinal fluid.

Embodiment 228

A nucleic acid sequencing apparatus comprising: (a) a nucleic acid library preparation compartment comprising two or more chambers configured to prepare a plurality of nucleic acids from a sample for a sequencing reaction, wherein said compartment is operatively connected to a nucleic acid sequencing chamber; (b) a nucleic acid sequencing chamber, wherein said nucleic acid sequencing chamber comprises: (i) one or more flow cells comprising a plurality of pores or sequencing cartridges configured for the passage of a nucleic acid strand, wherein two or more of the one or more flow cells are juxtaposed to one another; and (c) an automated platform, wherein said automated platform is programmed to robotically move a sample from said nucleic acid library preparation compartment into said nucleic acid sequencing chamber.

Embodiment 229

The nucleic acid sequencing apparatus of embodiment 228, wherein said automated platform moves a second sample from said nucleic acid library preparation compartment or from previously failed sequencing chamber into said nucleic acid sequencing chamber upon detecting a failure of a sequencing reaction.

Embodiment 230

The nucleic acid sequencing apparatus of embodiment 228, wherein said automated platform moves a second sample from said nucleic acid library preparation compartment into said nucleic acid sequencing chamber upon detecting a completion of a sequencing reaction.

Embodiment 231

The nucleic acid sequencing apparatus of embodiment 228, further comprising adding a barcode to a plurality of nucleic acids in said two or more chambers of (a), thereby providing a plurality of barcoded nucleic acids for said sequencing reaction.

Embodiment 232

The nucleic acid sequencing apparatus of embodiment 228, further comprising adding a plurality of mutually exclusive barcodes to a plurality of nucleic acids in said two or more chambers of (a), thereby providing a plurality of mutually exclusive barcoded nucleic acids.

Embodiment 233

The nucleic acid sequencing apparatus of embodiment 232, wherein said automated platform robotically moves two or more of said mutually exclusive barcoded nucleic acids into said nucleic acid sequencing chamber.

Embodiment 234

The nucleic acid sequencing apparatus of embodiment 232, wherein said automated platform robotically moves two or more of said mutually exclusive barcoded nucleic acids into a same flow cell of said one or more flow cells.

Embodiment 235

The nucleic acid sequencing apparatus of embodiment 232, wherein said sample is a food or an environmental sample.

Embodiment 236

The nucleic acid sequencing apparatus of embodiment 232, wherein said sample is a non-food sample.

Embodiment 237

The nucleic acid sequencing apparatus of embodiment 236, wherein said sample comprise blood, plasma, urine, tissue, faces, bone marrow, saliva or cerebrospinal fluid.

Embodiment 238

An embodiment comprising: (a) adding a first molecular index to a first plurality of nucleic acid sequences from a sample, thereby providing a first plurality of indexed nucleic acid sequences; and (b) adding a second molecular index to said first plurality of nucleic acid sequences from said first sample, thereby providing a second plurality of indexed nucleic acid sequences; and (c) adding a third molecular index to said first plurality of nucleic acid sequences from said first sample, thereby providing a third plurality of indexed nucleic acid sequences; (d) performing a sequencing reaction on said third plurality of nucleic acid sequences; and (e) demultiplexing, by a computer system, said third plurality of nucleic acid sequences comprising said first molecular index, said second molecular index, and said third molecular index.

Embodiment 239

The method of embodiment 238, wherein said first molecular index, said second molecular index, and said third molecular index are between 1 nucleotide and 18 nucleotides in length.

Embodiment 240

The method of embodiment 238, herein said first molecular index, said second molecular index, and said third molecular index are about 9 nucleotides in length.

Embodiment 241

The method of embodiment 238, wherein said first molecular index, said second molecular index, and said third molecular index have identical sequences.

Embodiment 242

The method of embodiment 238, wherein said first molecular index, said second molecular index, and said third molecular index have distinct sequences.

Embodiment 243

The method of embodiment 238, wherein said first plurality of indexed nucleic acid sequences, said second plurality of indexed nucleic acid sequences, and said third plurality of indexed nucleic acid sequences form a barcode comprising a periodic block design.

Embodiment 244

The method of embodiment 243, wherein said periodic block design has a defined Levenshtein distance between each of said first plurality of indexed nucleic acid sequences, said second plurality of indexed nucleic acid sequences, and said third plurality of indexed nucleic acid sequences.

Embodiment 245

The method of embodiment 238, wherein said first plurality of indexed nucleic acid sequences, said second plurality of indexed nucleic acid sequences, and said third plurality of indexed nucleic acid sequences form a barcode comprising a nonperiodic block design.

Embodiment 246

The method of embodiment 245, wherein said nonperiodic block design has a defined Levenshtein distance between each of said first plurality of indexed nucleic acid sequences, said second plurality of indexed nucleic acid sequences, and said third plurality of indexed nucleic acid sequences.

Embodiment 247

The method of embodiment 246, wherein said Levenshtein distance between each of said first plurality of indexed nucleic acid sequences, said second plurality of indexed nucleic acid sequences, and said third plurality of indexed nucleic acid sequences is the maximum possible Levenshtein distance.

Embodiment 248

An automatable microfluidic device for analysing a test liquid comprising: a sensor provided in a sensing chamber; a flow path comprising a sensing chamber inlet and a sensing chamber outlet connecting to the sensing chamber for respectively passing liquid into and out of the sensing chamber, and a sample input port in fluid communication with the inlet; a liquid collection channel downstream of the outlet; a flow path interruption between the sensing chamber outlet and the liquid collection channel, preventing liquid from flowing into the liquid collection channel from upstream, whereby the device may be activated by completing the flow path between the sample input port and the liquid collection channel; a conditioning liquid filling from the sample input port to the flow path interruption such that the sensor is covered by liquid and unexposed to a gas or gas/liquid interface; wherein the device is configured such that following activation of the device, the sensor remains unexposed to a gas or gas/liquid interface and the application of respectively one or more volumes of test liquid to a wet surface of the input port provides a net driving force sufficient to introduce the one or more volumes of test liquid into the device and displace buffer liquid into the liquid collection channel, wherein the device further comprises a removable seal for the sample input port, wherein the removable seal has a body that projects at least 1 cm above the surface of the microfluidic device when seated in the sample input port.

Embodiment 249

The device of embodiment 248, wherein the removable seal projects at least 1, 2.0, 2.5, 3, or 3.5 cm above the surface of the device.

Embodiment 250

The device of embodiment 248, wherein the removable seal is cylindrical, with a first flat end and a second tapered end that tapers to a size sufficient to plug the sample input port on the device.

Embodiment 251

The device of embodiment 248, wherein the removable seal comprises a metallic material.

Embodiment 252

The device of embodiment 249, wherein the removable seal comprises tungsten, aluminum, austenic stainless steel, or ferritic stainless steel.

Embodiment 253

The device of embodiment 249, wherein the removable seal is resistant to decontamination in dilute nitric acid, 1M NaOH, or dilute sodium hypochlorite.

Embodiment 254

The device of embodiment 249, wherein the removable seal comprises polypropylene or polycarbonate.

Embodiment 255

The nucleic acid sequencing apparatus of embodiment 228, wherein the one or more flow cells comprising a plurality of pores or sequencing cartridges is the automatable microfluidic device of any one of claims 248-255.

EXAMPLES

Example 1: Preparation of Food and Environmental Samples

Food and environmental samples may be processed for various purposes, such as the enrichment of one or more microorganism from the sample, or the isolation of one or more microorganism from the sample. The following protocol was used in the preparation of various food and environmental samples including: carcass rinses, stainless steel, primary production boot covers, dry pet food and shell eggs.

TABLE 1

Food and Environmental Sample Preparation

| Matrix | Sample Size | Enrichment Amount determined by volume or weight | Incubation |
| --- | --- | --- | --- |
| Carcass Rinse | 30 ± 0.6 mL sample rinse fluid | 20 ± 0.5 mL of Clear *Salmonella* media (CSM) | 42 ± 1° C. for 9-24 h |

TABLE 1-continued

Food and Environmental Sample Preparation

| Matrix | Sample Size | Enrichment Amount determined by volume or weight | Incubation |
|---|---|---|---|
| Stainless Steel | 1 sponge pre moistened with 1 0 mL tris-buffered saline | 10 ± 0.5 mL Clear *Salmonella* media (CSM) | 42 ± 1° C. for 9-24 h |
| Environmental Boot Cover | 1 environmental sampling bootie pre-moistened with 10 mL skim milk | 50 ± 1 mL Clear *Salmonella* media (CSM) | 42 ± 1° C. for 9-24 h |
| Pet Food | 25 ± 0.5 g | 100 ± 1 mL Clear *Salmonella* media (CSM) | 42 ± 1° C. for 9-24 h |
| Shell Eggs | 100 ± 2 g | 200 ± 2 mL Clear *Salmonella* media (CSM) | 42 ± 1° C. for 9-24 h |

Example 2: Obtaining a Carcass Food Sample

In this example, carcass food samples are generated by aseptically draining excess fluid from a carcass and transferring the carcass to a large sterile sampling bag. 100 mL of an enriched broth, in this case, Clear *Salmonella* media (CSM) was poured into the cavity of the carcass in the sampling bag. The carcass was rinsed inside and out with a rocking motion for about one minute, while assuring that all surfaces (interior and exterior of the carcass) were rinsed. About 20±0.5 mL of the CSM was added to the sample bag and homogenized by massaging sample bag for approximately 1.5-2 min. The sample was incubated at 42±1° C. for 9-24 h, providing an enriched sample.

Example 3: Obtaining an Environmental Sample From a Stainless Steel Surface

In this example, a stainless steel surface environmental sample was generated by moistening a sterile sampling sponge in 10 mL of Dey-Engley Broth prior to sampling, or using a sponge pre-moistened in the same. The sponge was used to touch, scrub, or otherwise contact the stainless steel surface and it was subsequently placed into a sampling bag. About 10±0.5 mL of CSM was added to the sampling sponge. Subsequently, the sponge was pressed to expel the collection broth into the CSM solution. The sample was incubated at 42±1° C. for 9-24 h, providing an enriched sample.

Example 4: Obtaining an Environmental Sample from a Boot Cover

In this example, an environmental sample from a boot cover was first pre-moistened in skim milk. About 50±1 mL of CSM was then added to the sampling bag containing boot cover environmental sample. The contents were mixed thoroughly for approximately 1.5-2 min, and incubated at 42±1° C. for 9-24 h, thereby providing an enriched sample. The enriched sample was removed from incubator and briefly mixed.

Example 5: Obtaining a Pet Food Sample

In this example, about 25±0.5 g of a pet food sample were added into a filtered sampling bag. About 100±1 mL CSM was then added to the sampling bag containing said pet food. The contents were mixed thoroughly for approximately 1.5-2 min, and incubated at 42±1° C. for 9-24 h, thereby providing an enriched sample. The enriched sample was removed from incubator and briefly mixed.

Example 6: Obtaining a Shell Egg Food Sample

In this example, about 100±2 g of a homogenized egg sample was added to a filtered sampling bag. About 200±2 mL CSM was then added to the sampling bag containing said homogenized egg sample. The contents were mixed thoroughly for approximately 1.5-2 min, and incubated at 42±1° C. for 9-24 h, thereby providing an enriched sample. The enriched sample was removed from incubator and briefly mixed.

Example 7: Photoreactive DNA-Binding Dye Treatment

In this example, a photoreactive DNA-binding dye, namely propidium monoazide (PMA) was added to various food and environmental samples, including the samples described in Examples 1-6. In general, 5 μL of a PMAxx solution was added to a well in a 200 μL 96-well PCR plate. Approximately 45 μL of each enriched sample from the sampling bags described in Examples 1-6 was added to individual wells in PCR plate containing PMAxx. The samples were mixed thoroughly by gentle pipetting and placed in the dark for 10 min at room temperature. Subsequently, the plates were incubated under a blue LED light for 20 min. 10 μL of each sample were then diluted with 90 μL of Lysis Buffer in a new 200 μL 96-well PCR plate. The plate was then incubated in a thermocycler as shown below. Alternatively the sample could have been incubated in a water bath.

| Step | Temperature | Time |
|---|---|---|
| 1 | 37° C. | 20 min |
| 2 | 95° C. | 10 min |

Example 8: PMAxx-Induced Removal of Free-Floating DNA

Figure 13:
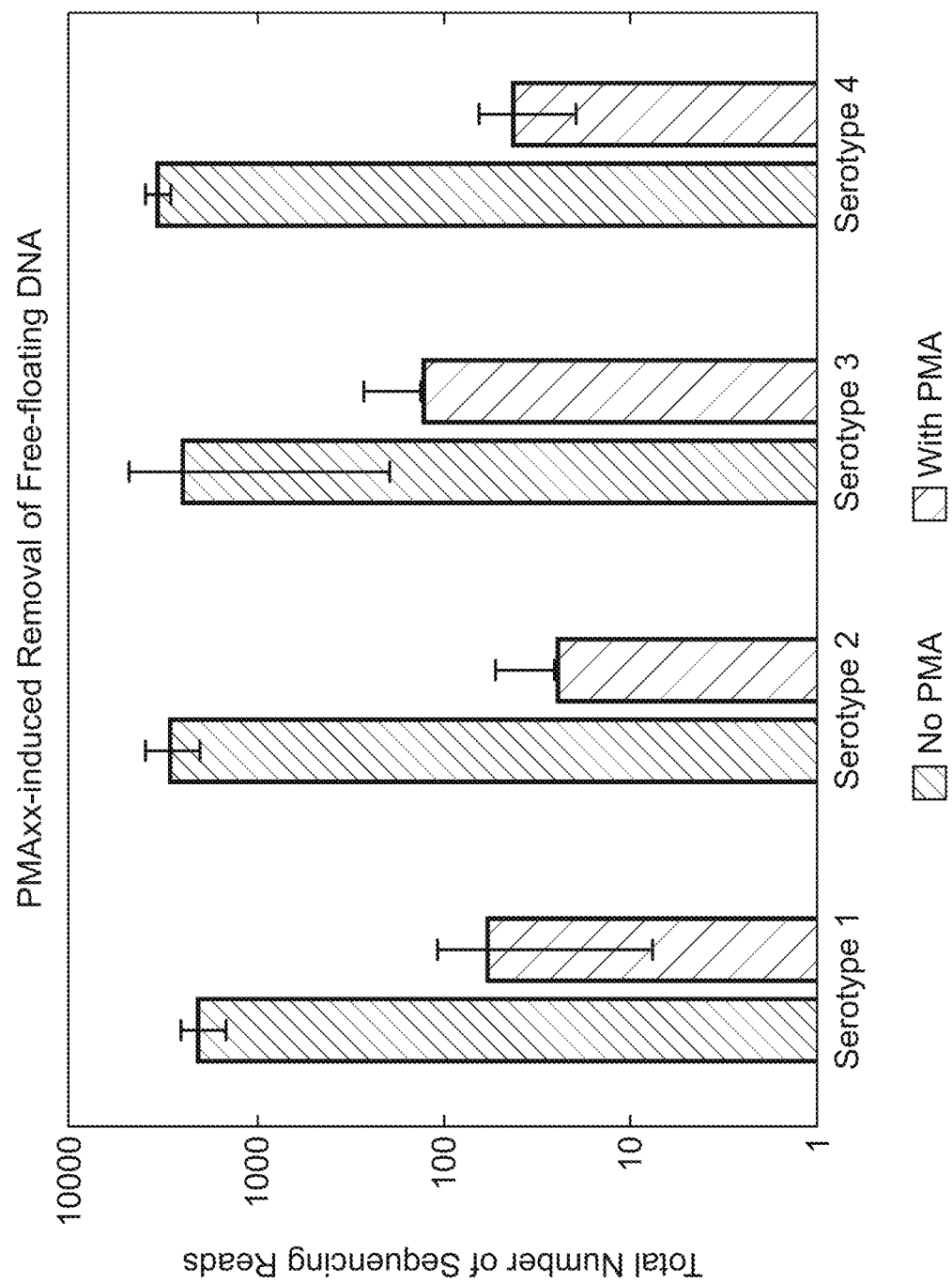
FIG. 13 illustrates the PMAxx-induced removal of free-floating DNA.

This example demonstrates that addition of a solution of the photoreactive DNA-binding dye PMAxx to a sample solution reduced the number of free-floating and contaminating DNA in said sample. Specifically, 45 μL of each enriched sample from the sampling bags as described in Examples 1-7 was added to individual wells of the 96-well PCR plate containing 25 μL of PMAxx solution. The sample solutions were mixed thoroughly by gentle pipetting and placed in the dark for 10 min at room temperature. Subsequently, the plates were incubated under a blue LED light for 20 min. 10 μL of each sample were then diluted with 90 μL of Lysis Buffer in a new 200 μL 96-well PCR plate. The plate was then incubated in a thermocycler as shown below. Analysis of the sample readouts showed that the addition of PMAxx solution (25 μL) to the sample solution was sufficient to reduce the number of free-floating DNA by at least 2 orders of magnitude, as shown in FIG. 13.

Example 9: Amplification Reaction

In this example, the samples described in Examples 1-8 were subjected to an amplification reaction. Briefly 15 μL of primer cocktail and polymerase master mix was added to individual wells of an empty 200 μL 96-well PCR plate. About 5 μl of each sample treated with a photoreactive DNA-binding dye treatment was added to the respective wells containing the polymerase master mix. The solution was mixed gently by pipetting up and down and placed in a thermocycler with the conditions described below.

| Step | Temperature | Time |
| --- | --- | --- |
| 1 | 95° C. | 3 min |
| 2 | 95° C. | 30 sec |
| 3 | 57° C. | 1 min |
| 4 | 72° C. | 1 min |
| 5 | | Go to step 2, 37 times |
| 6 | 72° C. | 10 min |
| 7 | 10° C. | Hold |

Example 10: Library Preparation

In this example, Solid Phase Reversible Immobilization (SPRI) Magnetic Beads were used to purify and quantify one or more of the samples described in Examples 1-9. Briefly, the SPRI beads were removed from 4° C. storage and allowed to reach room temperature for approximately 15 min. About 1 mL of 80% ethanol was prepared by combining 800 μL of ethanol and 200 μL of molecular biology grade water. Equal volumes of each samples amplification product (described in Example 9) was used to obtain at least 100 μL of pooled products, which was purified using the SPRI beads along with standard manufacturing protocols. Briefly, 100 μL of vortexed, pooled PCR product was pipetted into a 0.2 mL PCR tube and add 60 μL of SPRI beads. The tube was mixed thoroughly by pipetting up and down approximately 10 times and incubated at room temperature for 5 min. The sample/bead mixture was placed in a magnetic stand and the beads were allowed to pellet in a ring for approximately 30-60 s, leaving a clear supernatant. The supernatant was discarded by leaving the tube in the magnetic stand while placing the pipette tip to the bottom center of the tube when aspirating to avoid disturbing the beads. 190 μL of 80% ethanol was then added to the tube, and incubated for 5-10 s. The tube was aspirated fully and the ethanol solution discarded. The process was repeated twice. The sample was allowed to dry for 3-5 min at room temperature, or until no visible ethanol remained. Once thoroughly dry, the tube was removed from the magnetic stand and re-suspended in 50 μL of 10 mM RSB into the tube. The tube was mixed thoroughly by gently pipetting up and down approximately 10 times and incubate at room temperature for 2 min. The tube was moved to a magnetic stand and incubated at room temperature for 2 min to allow the beads to pellet. 50 μL of the eluate was removed and retained.

Example 11: End Repair

In this example, the terminal ends of fragment nucleic acids described in Example 10 were repaired as described below. First, the following reagents were combined and mixed well by pipetting up and down approximately 10 times.

| Reagent | Volume |
| --- | --- |
| Purified Pooled Libraries | 45 μL |
| NEB Ultra II end-prep reaction buffer | 7 μL |
| NEB Ultra II End-prep enzyme mix | 3 μL |
| ONT DNA CS (DCS) | 5 μL |
| Total | 60 μL |

The samples were then spun for approximately 5 s using a benchtop minifuge. End-repair was performed in a thermal cycler with the following conditions:

| Step | Temperature | Time |
| --- | --- | --- |
| 1 | 20° C. | 5 min |
| 2 | 65° C. | 5 min |
| 3 | 25° C. | 5 min |

Subsequently, the samples were spun for approximately 5 s using a benchtop minifuge. 60 μL of SPRI beads were added to the end-repaired product and mixed by pipetting up and down approximately 10 times. The samples were incubated for 5 min at room temperature. The sample/bead mixture was placed in a magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. 190 μL of 80% ethanol was added to the samples. The 80% ethanol solution was incubated in the tube for 5-10 s, and the ethanol was aspirated and discarded. This process was repeated twice. The sample was allowed to dry for 5 min at room temperature, or until no visible ethanol remained. The beads were resuspended with 31 μL molecular biology grade water and mixed by gently pipetting up and down approximately 10 times and incubate for 2 min at room temperature. The tube was moved to a magnetic stand and the beads were allowed to pellet for approximately 30-60 s. The eluate was retained as the "end-repaired product".

Example 12: Ligation

In this example, using the end-repaired product of Example 11, the following reagents were combined:

| Reagent | Volume |
| --- | --- |
| End-repaired product | 30 μL |
| ONT Adapter Mix (AMX 1D) | 20 μL |
| NEB Blunt/TA Ligase Master Mix | 50 μL |
| Total | 100 μL |

The reagents were gently mixed by pipetting up and down approximately 10 times and were incubated at room temperature for 10 min. About 40 μL of SPRI beads were added to the mixture, gently mixed, and incubated at room temperature for 5 min. The sample/bead mixture was placed in a magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was removed from the magnetic rack and 140 μL of ONT-Adapter Bead Binding buffer was pipetted onto the beads. The sample was mixed by gently pipetting up and down approximately 10 times to resuspend the pellet. The tube was returned to the magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was removed from the magnetic rack and an additional 140 μL of Adapter Bead Binding buffer was added and pipetted up and down to resuspend the pellet. The sample/bead mixture was placed in a magnetic stand and the beads were allowed to pellet into a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was then removed from the magnetic stand. About 15 μL of Elution Buffer (ELB) was added to the beads, and the beads were mixed thoroughly by pipetting up and down approximately 10 times and incubate for 10 minutes at room temperature for 5 min. The tubes were moved to a magnetic stand and the beads allowed to pellet for approximately 30-60 s. About 15 μL of eluate was remove and retained as the "final ligated product" for sequencing.

Example 13: Pore Sequencing

In this example, a food or an environmental sample was processed by pore sequencing using standard manufacturer protocols. Briefly, one or more flow cells were primed by combining the following reagents per flow cell:

| Reagent | Volume |
|---|---|
| ONT-Running Buffer with Fuel Mix (RBF) | 480 μL |
| Molecular grade H$_2$O | 520 μL |
| Total | 1,000 μL |

A loading library was prepared by combining the following reagents:

| Reagent | Volume |
|---|---|
| ONT-Running Buffer with Fuel Mix (RBF) | 35 μL |
| ONT-Library Loading Beads (LLB) | 25.5 μL |
| Final ligated product | 12 μL |
| Molecular grade H$_2$O | 2.5 μL |
| Total | 75 μL |

Figure 14:
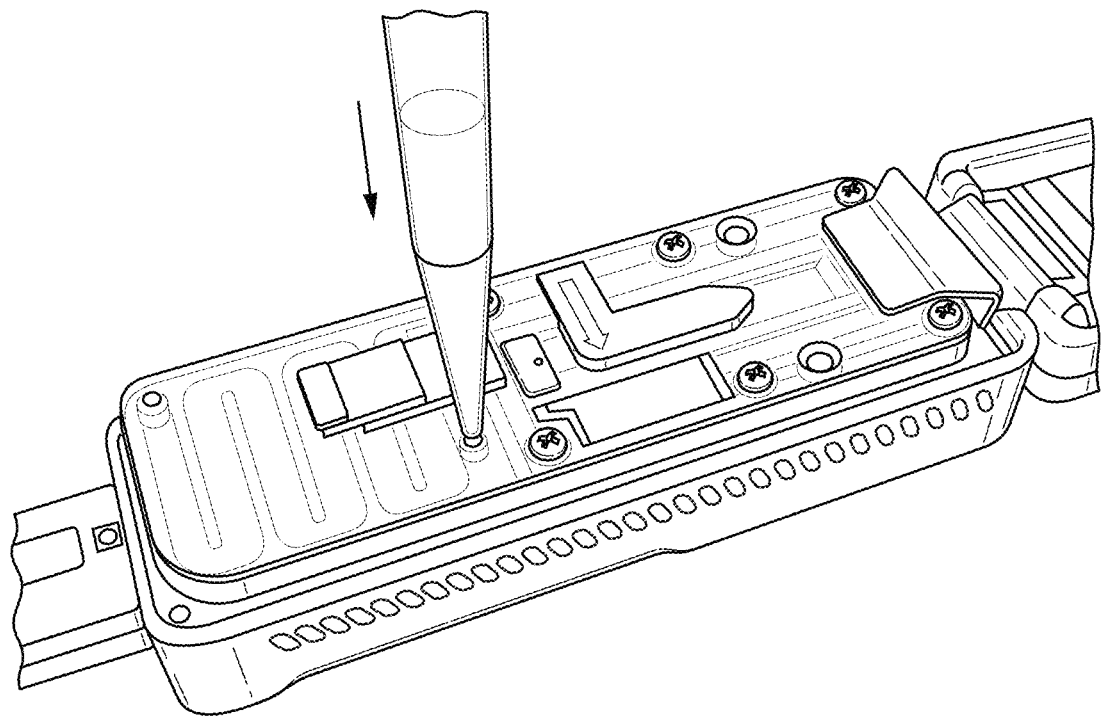
FIG. 14 illustrates a priming port in a flow cell.
Figure 15:
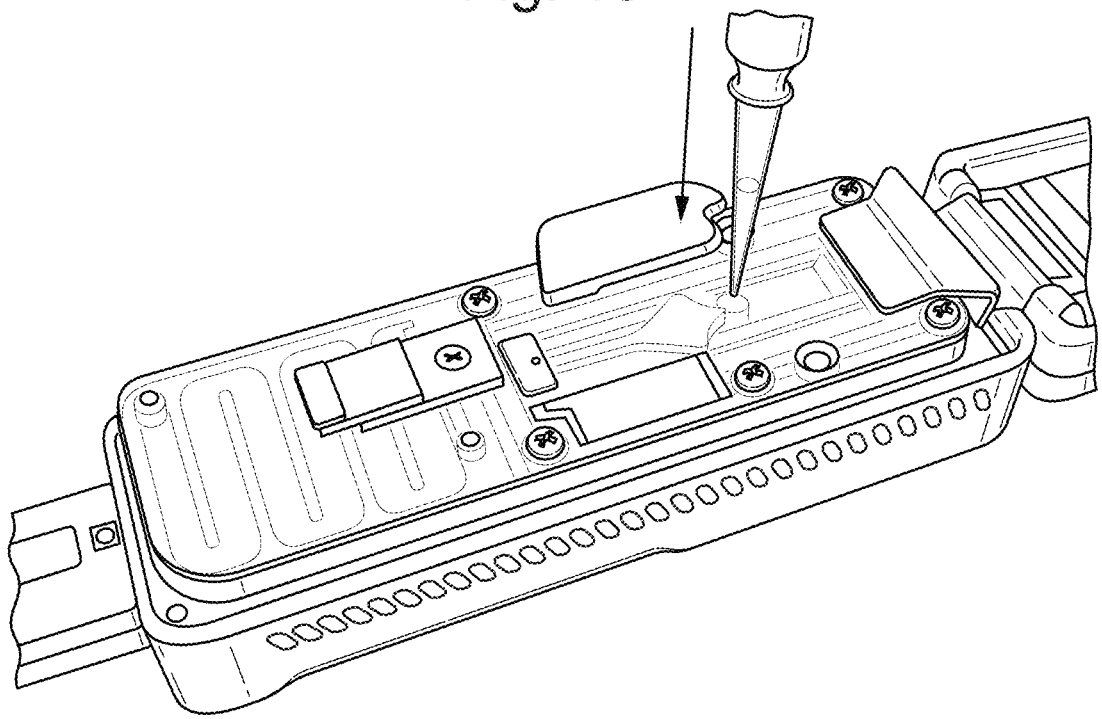
FIG. 15 illustrates a dispensing of a loading library on a flow cell.

The priming port on the Flow Cell was gently opened and approximately 50 μL of the preservative buffer and any small bubbles were removed, as illustrated by FIG. 14. About 800 μL of the priming mix was added into the priming port of the Flow Cell. Subsequently, 200 μL of the priming mix was dispensed into the Priming port. The final loading library was mixed thoroughly and 75 μL were added into the SpotON port, as illustrated by FIG. 15. The lid of the pore sequencing device was closed and the sequencing was executed.

Example 14: Data Analysis and Interpretation

In this example, an electronic communication comprising a data set associated with the sequencing reaction described in Example 13 was transmitted over the cloud for analysis. The results of the analysis were reported back to customer. FIG. 16 in this particular example, the customer requested an analysis of the sample for the presence or absence of *Listeria*, *Salmonella*, *Campylobacter*, and *E. coli*, which required the simultaneous targeting of multiple pathogens.

Example 15: Identification of a Microorganism in a Food, Environmental Sample, or in a Non-Food Associated Sample by Microbiome Metagenomics and Supervised Learning In this example, data from pore sequencing was used to identify foodborne disease-causing microorganisms. Briefly, the methods and processes described in Examples 1-13 were used to identify food or environmental samples comprising one or more of the organism shown below.

TABLE 2

Exemplary Pathogenic Microorganisms Identified by Methods According to This Disclosure

| Organism | Common Name of Illness | Onset Time After Ingesting | Signs & Symptoms | Duration of Illness | Food Sources |
|---|---|---|---|---|---|
| *Bacillus cereus* | *B. cereus* food poisoning | 10-16 hrs | Abdominal cramps, watery diarrhea, nausea | 24-48 hours | Meats, stews, gravies, vanilla sauce |
| *Campylobacter jejuni* | Campylobacteriosis | 2-5 days | Diarrhea, cramps, fever, and vomiting; diarrhea may be bloody | 2-10 days | Raw and undercooked poultry, unpasteurized milk, contaminated water |
| *Clostridium botulinum* | Botulism | 12-72 hours | Vomiting, diarrhea, blurred vision, double vision, difficulty in swallowing, muscle weakness. Can result in respiratory failure and death | Variable | Improperly canned foods, especially home-canned vegetables, fermented fish, baked potatoes in aluminum foil |

TABLE 2-continued

Exemplary Pathogenic Microorganisms Identified by Methods According to This Disclosure

| Organism | Common Name of Illness | Onset Time After Ingesting | Signs & Symptoms | Duration of Illness | Food Sources |
|---|---|---|---|---|---|
| *Perfringens* | Perfringens food poisoning | 8-16 hours | Intense abdominal cramps, watery diarrhea | Usually 24 hours | Meats, poultry, gravy, dried or precooked foods, time and/or temperature-abused foods |
| *Cryptosporidium* | Intestinal cryptosporidiosis | 2-10 days | Diarrhea (usually watery), stomach cramps, upset stomach, slight fever | May be remitting and relapsing over weeks to months | Uncooked food or food contaminated by an ill food handler after cooking, contaminated drinking water |
| *Cyclospora cayetanensis* | Cyclosporiasis | 1-14 days, usually at least 1 week | Diarrhea (usually watery), loss of appetite, substantial loss of weight, stomach cramps, nausea, vomiting, fatigue | May be remitting and relapsing over weeks to months | Various types of fresh produce (imported berries, lettuce, basil) |
| *E. coli* (*Escherichia coli*) producing toxin | *E. coli* infection (common cause of "travelers' diarrhea") | 1-3 days | Watery diarrhea, abdominal cramps, some vomiting | 3-7 or more days | Water or food contaminated with human feces |
| *E. coli* O157:H7 | Hemorrhagic colitis or *E. coli* O157:H7 infection | 1-8 days | Severe (often bloody) diarrhea, abdominal pain and vomiting. Usually, little or no fever is present. More common in children 4 years or younger. Can lead to kidney failure. | 5-10 days | Undercooked beef (especially hamburger), unpasteurized milk and juice, raw fruits and vegetables (e.g. sprouts), and contaminated water |
| Hepatitis A | Hepatitis | 28 days average (15-50 days) | Diarrhea, dark urine, jaundice, and flu-like symptoms, i.e., fever, headache, nausea, and abdominal pain | Variable, 2 weeks-3 months | Raw produce, contaminated drinking water, uncooked foods and cooked foods that are not reheated after contact with an infected food handler; shellfish from contaminated waters |
| *Listeria monocytogenes* | Listeriosis | 9-48 hrs for gastro-intestinal symptoms, 2-6 weeks for invasive disease | Fever, muscle aches, and nausea or diarrhea. Pregnant women may have mild flu-like illness, and infection can lead to premature delivery or stillbirth. The elderly or immuno-compromised patients may develop bacteremia or meningitis. | Variable | Unpasteurized milk, soft cheeses made with unpasteurized milk, ready-to-eat deli meats |
| Noroviruses | Variously called viral gastroenteritis, winter diarrhea, | 12-48 hrs | Nausea, vomiting, abdominal cramping, diarrhea, fever, | 12-60 hrs | Raw produce, contaminated drinking water, uncooked |

TABLE 2-continued

Exemplary Pathogenic Microorganisms Identified by Methods According to This Disclosure

| Organism | Common Name of Illness | Onset Time After Ingesting | Signs & Symptoms | Duration of Illness | Food Sources |
|---|---|---|---|---|---|
| | acute non-bacterial gastroenteritis, food poisoning, and food infection | | headache. Diarrhea is more prevalent in adults, vomiting more common in children. | | foods and cooked foods that are not reheated after contact with an infected food handler; shellfish from contaminated waters |
| Salmonella | Salmonellosis | 6-48 hours | Diarrhea, fever, abdominal cramps, vomiting | 4-7 days | Eggs, poultry, meat, unpasteurized milk or juice, cheese, contaminated raw fruits and vegetables |
| Shigella | Shigellosis or Bacillary dysentery | 4-7 days | Abdominal cramps, fever, and diarrhea. Stools may contain blood and mucus. | 24-48 hrs | Raw produce, contaminated drinking water, uncooked foods and cooked foods that are not reheated after contact with an infected food handler |
| Staphylococcus aureus | Staphylococcal food poisoning | 1-6 hours | Sudden onset of severe nausea and vomiting. Abdominal cramps. Diarrhea and fever may be present. | 24-48 hours | Unrefrigerated or improperly refrigerated meats, potato and egg salads, cream pastries |
| Vibrio parahaemolyticus | V. parahaemolyticus infection | 4-96 hours | Watery (occasionally bloody) diarrhea, abdominal cramps, nausea, vomiting, fever | 2-5 days | Undercooked or raw seafood, such as shellfish |
| Vibrio vulnificus | V. vulnificus infection | 1-7 days | Vomiting, diarrhea, abdominal pain, blood borne infection. Fever, bleeding within the skin, ulcers requiring surgical removal. Can be fatal to persons with liver disease or weakened immune systems. | 2-8 days | Undercooked or raw seafood, such as shellfish (especially oysters) |

First, a database was constructed using data from approximately 35,000 food or environmental samples (of which about 10% contained traces of pathogenic microorganisms as shown in Table 3) using two components: microorganism presence and chemical composition. Pore sequencing in combination with use of characteristic polymorphic gene regions (comprising SNP's, RFLP's, STRs, VNTR's, hypervariable regions, minisatellites, dinucleotide repeats, trinucleotide repeats, tetranucleotide repeats, simple sequence repeats, indels, and insertion elements) associated with a wide diversity of microorganisms were used to analyze each sample for the presence or absence of 17,800 different bacterial species (representing both pathogenic and non-pathogenic bacterial species). Additionally, data on sample composition was collected for 4,600 food ingredients in each environmental/food sample.

The data using the top bacteria associated with pathogen contamination (exemplified in FIG. 5) was used to train a classification model, which was tested for overfitting by machine learning techniques.

We further tested the performance of the model by testing a set of unknown food or environmental samples (50% of each). The full results of and ROC analysis of accuracy and precision of the classification models are presented in Table 3. In the cases of all the pathogens in Table 3, the metagenomics-based classification model had higher than 95% precision and 97% accuracy for pathogen detection.

TABLE 3

Independent Validation of Pathogen Prediction in Unknown Samples

| Pathogen | Accuracy Score | Precision Score |
| --- | --- | --- |
| Vibrio parahaemolyticus | 99.78% | 96.55% |
| Staphylococcus aureus | 99.67% | 100.00% |
| Yersinia pseudotuberculosis | 99.45% | 100.00% |
| Vibrio vulnificus | 99.12% | 100.00% |
| Shigella boydii | 99.12% | 100.00% |
| Salmonella enterica | 96.16% | 94.39% |
| Escherichia coli | 97.48% | 98.40% |

Example 16: In Silico Evaluation of Primer Sensitivity and Specificity

This example describes the in silico evaluation of primer sensitivity and specificity for pathogen detection in PCR assays. First, a candidate primer pair was mapped against inclusion and exclusion sequences in sequence databases. Secondly, the identified hits are tabulated based on predicted amplification patterns in order to then determine the sensitivity and specificity of the primer pair in silico.

Figure 17:
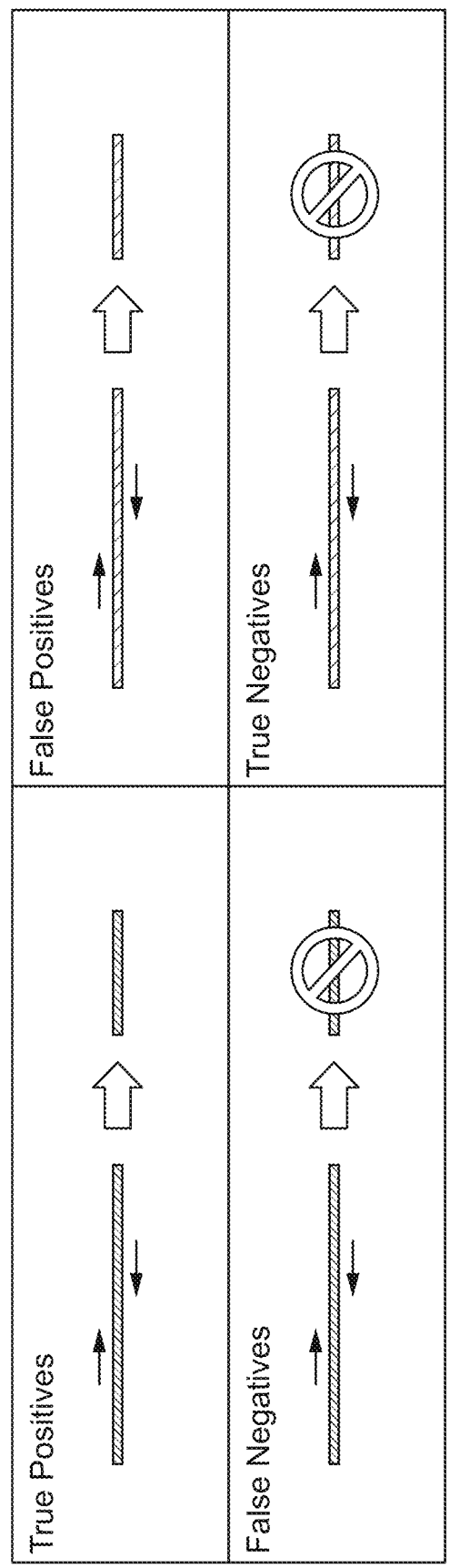
FIG. 17 illustrates the in silico prediction of primer sensitivity/specificity.

Specifically, a primer pair was designed to target *Salmonella* Montevideo and *Salmonella* Oranienburg. The composition of the sequence database for in silico evaluation contained 7705 *Salmonella* genomes, including 98 Montevideo/Oranienburg genomes, and 1707 non-*Salmonella* genomes (total of 9412 genomes). Tabulation of the analysis results showed that the exact number of 98 *Salmonella* Montevideo and Oranienburg genomes was identified as true positive hits. The remaining 9314 (which equals the total number of 9412 genomes minus the 98 true positive hits identified) genomes were characterized as true negative results. The results are shown in FIG. 17.

Example 17: Reuse of Flow Cells

This example shows that the MinION/GridION flow cell can be reused for sequence sample analysis for at least 2 times. Between each sample analysis (50 samples analyzed in each analysis) the flow cell was washed with a buffer system resulting in 30,000 reads and 26,000 reads per sample during the second and third reuse, respectively, compared to 36,000 reads per sample when using a new flow cell (FIG. 18). FIG. 19 illustrates that the number of reads per sample for reused MinION/GridION flow cells was well above the acceptable minimum threshold of 10,000 (10 K) reads per sample.

Example 19: Automated Pathogen Risk Detection

A significant source of confounding data in pathogen risk detection is contamination of samples by resident microorganisms on human handlers. Accordingly, we deployed a biomek-based sample sequencing platform that requires no human handling after enrichment (see FIG. 11 and FIG. 12) to implement the methods of Examples 10-13 and 15. Automation included every step of library preparation post incubation of the samples as in Examples 1-6, and included cell lysis, PCR, clean up, and sequencing. An automated handling system is illustrated in FIG. 11.

To determine the performance of our automated handling system, we analyzed samples spiked with 10 different *Salmonella* serotypes (Enteritidis, Thyphimurium, I 4_[5]_12: i—, Newport, Javiana, Infantis, Montevideo, Heidelberg, Muenchen) by automated or manual handling. The results are presented in FIG. 20. Serotype detection accorded 100% between manual and automatic handling, and a student's T-test of the number of sequencing reads generated indicated no significant difference between manual and automated handling.

Example 20: Detection of Food Product Expiration/Shelf Life by Microbiome Metagenomics A significant limitation of existing environmental pathogen detection methods is that they involve culturing, which involves the use of multiple different specialized media to detect different classes of pathogens (e.g. bacteria autotrophic for one or more nutrient vs those not). This severely limits the ability to detect food contamination during storage. Accordingly, we applied our environmental sampling/pore sequencing technique as outlined in Examples 1-13 on 100 samples of chicken wings and 100 samples of ground chicken. Each sample was analyzed for the presence/absence of 17,800 pathogenic and non-pathogenic bacteria.

Figure 21:
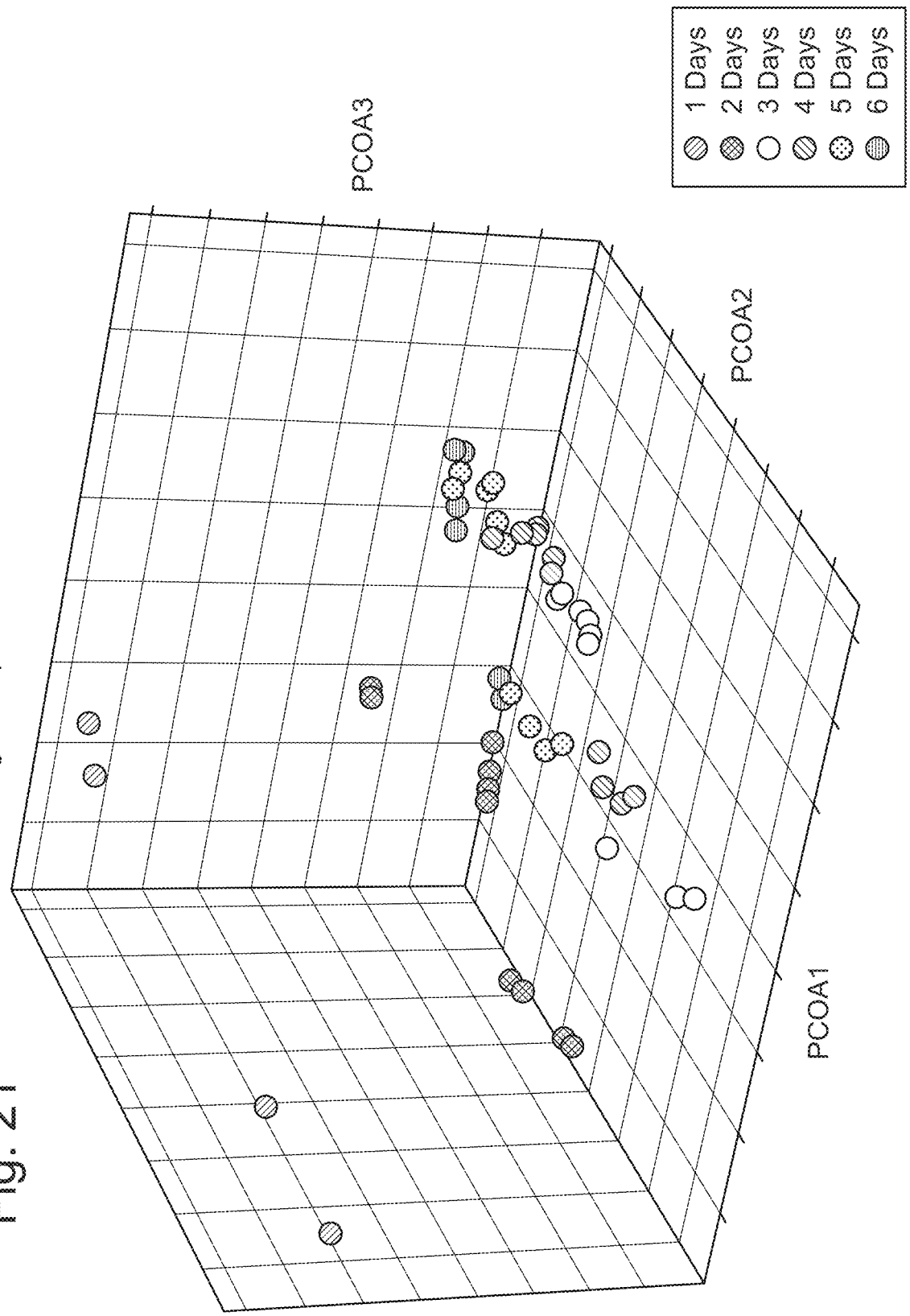
FIG. 21 illustrates a principal component analysis to chicken wing chicken data sets.
Figure 22:
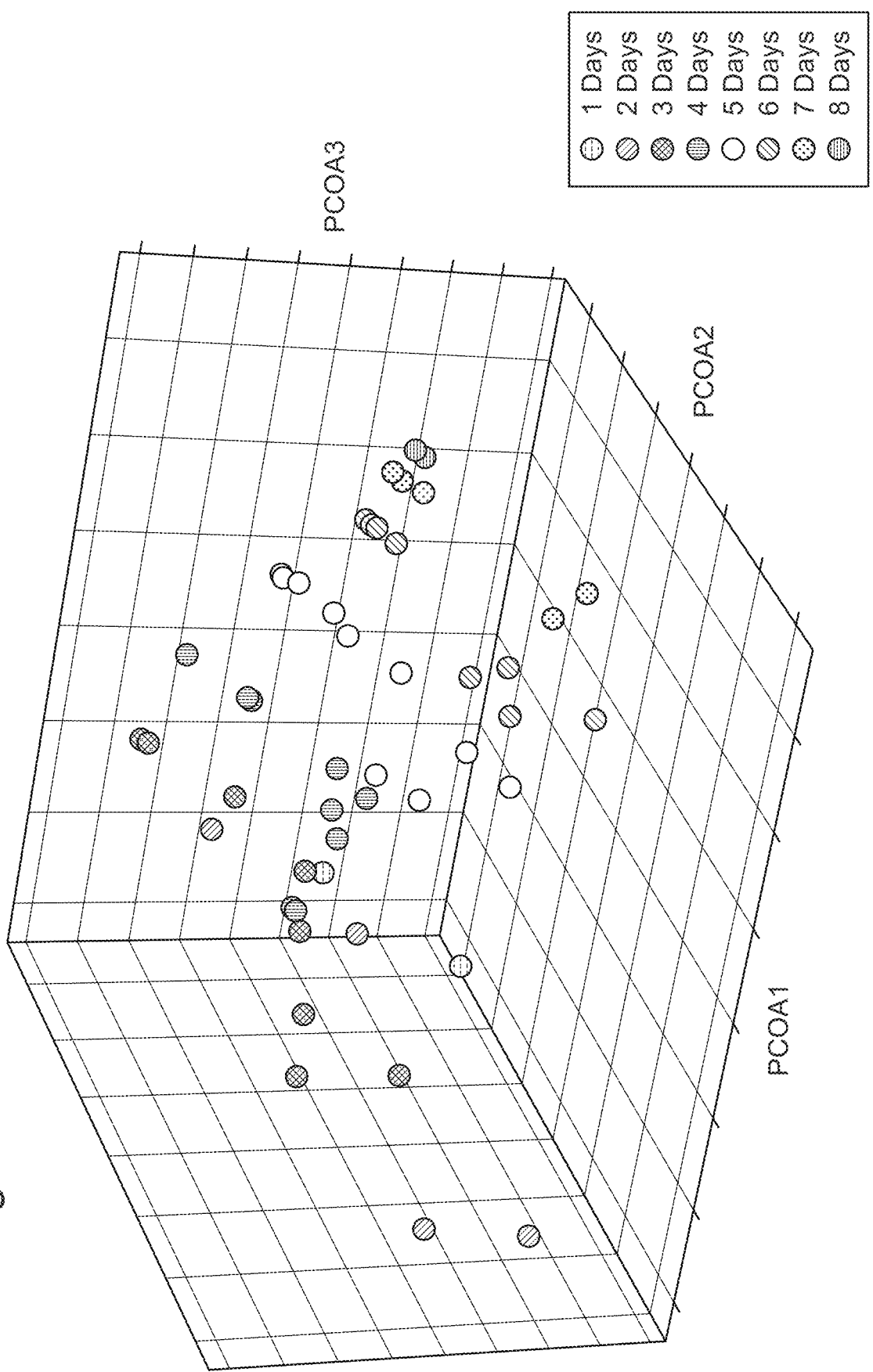
FIG. 22 illustrates a principal component analysis to ground chicken data sets.

We applied a principle components analysis to the whole or ground chicken data sets, which is presented in FIG. 21 and FIG. 22. Data points for both whole and ground chicken samples cluster along a discernable trajectory more than 2 days prior to their expiration date (see movement along PC2 in the whole chicken sample and PC1/PC3 in the ground chicken sample), while data points 1-2 days from expiration begin to rapidly diverge.

The principle components analysis suggested a classification model could be built to detect whether or not a whole or ground chicken sample had expired. The data on the presence/absence of 17,800 pathogenic and non-pathogenic bacteria was used to generate a classification model. When tested on an independent data set of samples, this classifier showed 97% accuracy in detecting samples past their expiration date using an ROC analysis.

Example 21: Comparison of Periodic and Nonperiodic Block Design for Sequencing Sample Barcodes; Reduction of Crosstalk Using Non-Periodic Block Primer Design To improve detection of desired sequences during sequencing runs, we tested the performance of different barcoding designs on sequence detection. We generated unique sequences of nucleotides with maximum Levenshtein distances from each other and used them to generate two formats of barcodes to be applied to sequences during library preparation: a) a periodic block design, in which each barcode consisted of a unique block sequence repeated 3 times, and b) a nonperiodic block design, in which 3 unique blocks were combined in tandem for each barcode sequence.

We tested these nonperiodic and periodic block designs alongside a conventional barcode design (which were designed barcodes provided by our sequencing platform provider) when applied to the same samples in test sequencing runs (see FIG. 23). Briefly, a defined Levenshtein distance between each "building block" or molecular index can be used to form larger barcodes. Such larger barcodes can have a period block design, such as barcodes created by repeating each block multiple times with the largest possible Levenshtein distance between the individual blocks (see FIG. 23). Alternatively, such barcodes can also have a nonperiodic block design, such as barcodes created by concatenative multiple blocks that are unique to each barcode with the largest possible Levenshtein distance between the individual blocks (see FIG. 23).

We performed 10 ONT MinION runs and averaged the % of retained sequences and crosstalk for each run. The results are presented in Table 4. Both periodic and nonperiodic barcode designs showed improvements in retention and crosstalk versus the conventional design, with the nonperiodic design being the best in both metrics.

Both barcode designs present distinct advantages. Both increase the number of retained sequences and allow for adjustable precision by choosing 1, 2, or 3 blocks in demultiplexing, but the periodic design requires fewer repeat blocks and presents less complexity in demultiplexing, whereas the nonperiodic design allows for improved crosstalk prevention. The improved crosstalk prevention of the nonperiodic design suggests a method of reducing crosstalk during highly multiplexed runs or when a flowcell is reused.

TABLE 4

Performance of Conventional Barcode Design vs Periodic and Nonperiodic Block Designs

|  | Conventional Design | Periodic Block Design | Nonperiodic Block Design |
| --- | --- | --- | --- |
| Retained Sequences | 85% | 96% | 98% |
| Crosstalk | 6% | 5% | 2% |

Example 22: Detection of Transient vs Resident Microbes by Metagenomics

Figure 24:
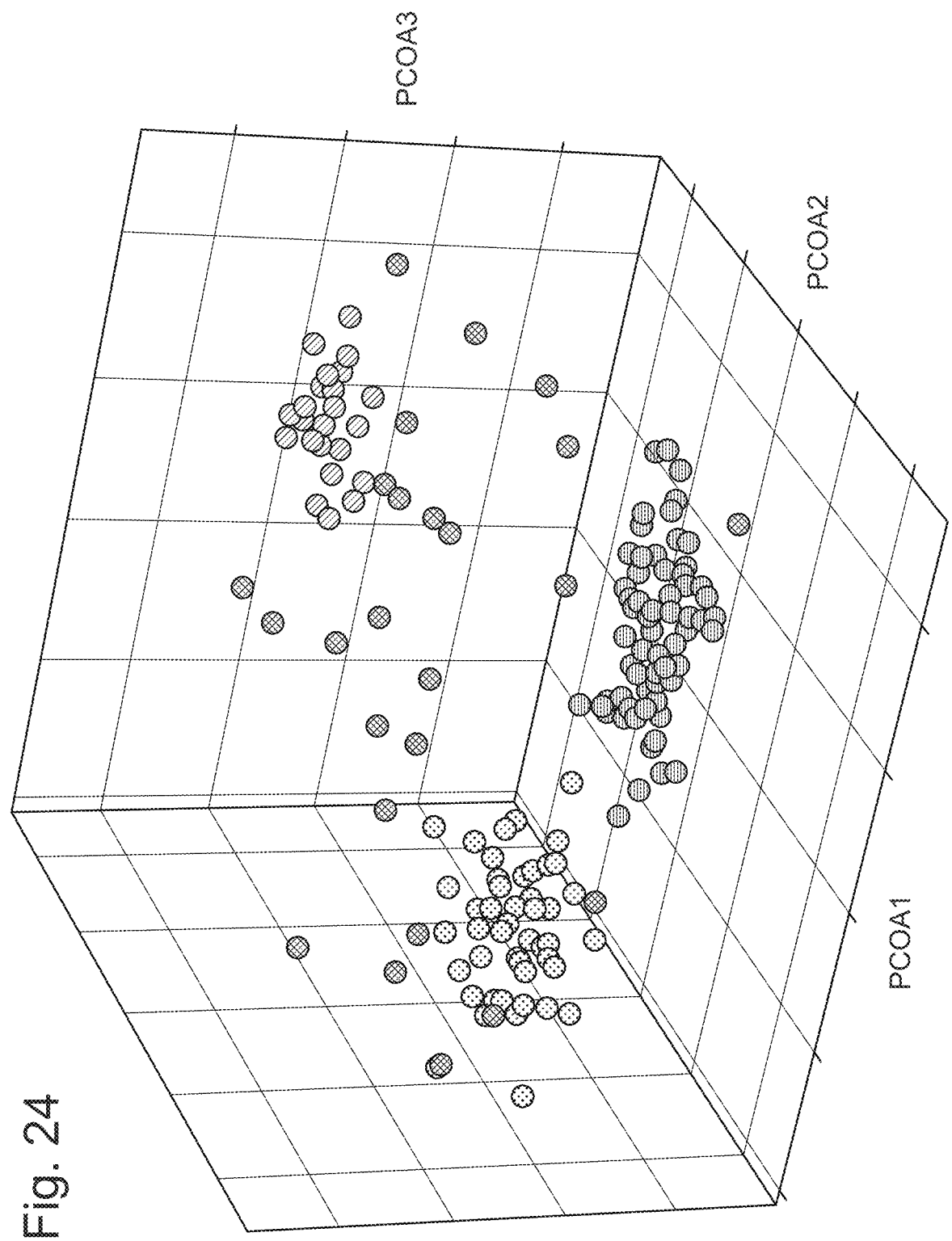
FIG. 24 illustrates a principle component analysis of *Listeria* sequences identifying clusters of closely related bacteria which likely originated from the same source.

*Listeria*-containing food and environmental samples were prepared, libraries were constructed, and sequencing was performed as in Examples 1-13 and 15. Samples were analyzed for the presence of *Listeria* by analyzing highly polymorphic genetic markers. A principle component analysis of the *Listeria* sequences isolated from sequencing (see FIG. 24) identified clusters of closely related bacteria which likely originated from the same source.

Example 23: Detection of Microbial Serotype Early in Sequencing Run

The length of time for a full sequencing run represents a major limitation in the speed of detection or serotyping of pathogenic bacterial strains by high-throughput sequencing. We hypothesized that using "live" detection calls during sequencing runs (which can be performed as early as 1 hour for ONT MinION and GridION, and 5 hours for Illumina MiSeq) would allow for certain bacteria to be detected/serotyped on a preliminary basis based on sequencing, with follow-up confirmation by other non-sequencing-based tests (e.g. Q-PCR).

We performed a test analysis of 50 environmental samples with about 15% positive for one of the pathogens identified in Table 3; positive samples were spiked with *Salmonella, Listeria, E. coli*, and *campylobacter* (2 samples each) from the top known pathogenic top strain/serotypes. Pathogen species was detected by detection of characteristic genomic markers. We compared the accuracy of species detection and serotyping at "live" and complete timepoints for the sequencing runs. The results are presented in Table 5. Early detection (1 hour for ONT MinION, and 5 hours for Illumina MiSeq) was 100% accurate for both formats, while MinION showed improved accuracy for serotyping.

TABLE 5

"Early call" Detection of Bacterial Species and Serotype

| Platform | Sequences at early call | Detection calls | Serotyping calls | Final serotyping call |
| --- | --- | --- | --- | --- |
| MiSeq | 425,000 | 100% | 20% | 100% |
| MinION | 630,000 | 100% | 60% | 100% |

Example 24: Cell Concentration From Prepared Food or Environmental Microbial Samples Food or environmental samples of microbes prepared as in Examples 1-6 are ideally subjected to a concentration step to maximize the concentration of pathogen associated nucleic acids (e.g. represented in CFU/µl) and improve downstream detection by sequencing. A filter-free method involving phase separation is used to maximize throughput in sample preparation.

Figure 27:
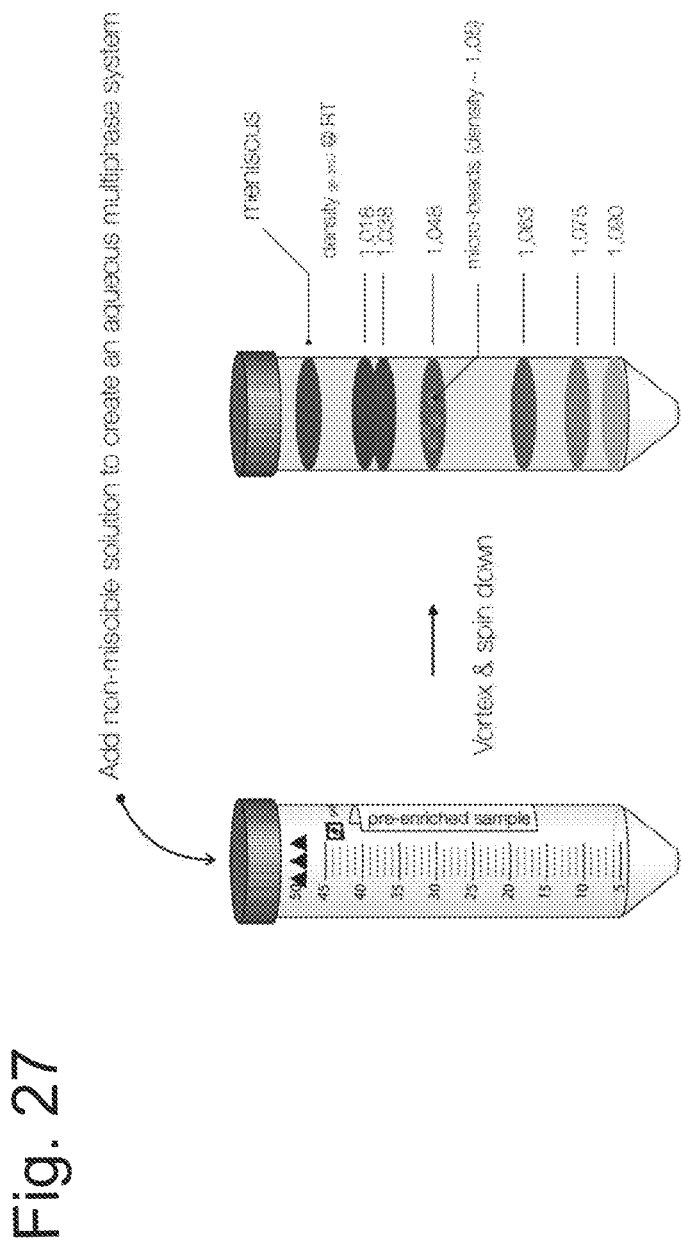
FIG. 27 illustrates the phase-separation microbial concentration method described in Example 23.

Briefly, a small volume of a liquid formulation that is designed to be to a) not be miscible with the enrichment media; b) possess a density of mass similar to that of the desired cell type; c) be unreactive with downstream applications; d) spontaneously separate into a distinct layer after mixing with the enrichment media output from the processes of Examples 1-6 is added to the enrichment media, and the sample is allowed to equilibrate in a conical tube to reach a state shown in FIG. 27, which illustrates the process with microbeads instead of cells. In some embodiments, the equilibration occurs with or without centrifugation-assisted phase separation. The aqueous liquid formulation added can contain a mixture of polymers capable of forming step-gradients in density (e.g. Ficoll, PEG, glycerol). The desired cell material (e.g. microbeads shown in FIG. 27), is then collected by directly pipetting the desired layer and collecting it via a flow-fraction collection method.

Example 25: Re-Using Flow Cells 3 groups of 96 samples (including a mixture of samples either target pathogen positive as positive samples or non-target pathogen as negative samples) were prepared according to the methods described in examples 7-12. Samples were barcoded by transfer of the libraries to 96-well plates containing a uniquely indexed barcode specific to each well of the 96-well plate. Each group of samples from the 96 well plates were pooled into a single solution and each sample was run successively on an Oxford Nanopore flow cell. Each cell was washed with buffer in between the runs. Different numbers of *Salmonella*-positive and -negative samples were provided between the runs to introduce sequence variety into each group. These samples were apportioned into different wells of barcode-indexed plates. The index plates and barcode assignments for each group are presented in the table below. Tables 6-8 illustrate on a 96 well grid the sample assignment (positive or negative) to each well/unique barcode index for each of the 3 successive runs.

Table 6 illustrates index and well assignments of positive and negative *Salmonella* samples for each run on the same nanopore flow cell. Table 6 illustrates a first run, plate IP1.

TABLE 6

|  | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | + | + | + | + | + | + | + | + | + | + | + | + |
| B | − | − | − | − | − | − | − | − | − | − | − | − |

TABLE 6-continued

|   | 1 | 2 | 3 | 4 | 5 | 6 | 7 | 8 | 9 | 10 | 11 | 12 |
|---|---|---|---|---|---|---|---|---|---|----|----|----|
| C | + | + | + | + | + | + | + | + | + | +  | +  | +  |
| D | + | + | + | + | + | + | + | + | + | +  | +  | +  |
| E | + | + | + | + | + | + | + | + | + | +  | +  | +  |
| F | + | + | + | + | + | + | + | + | + | +  | +  | +  |
| G | − | − | − | − | − | − | − | − | − | −  | −  | −  |
| H | + | + | + | + | + | + | + | + | + | +  | +  | +  |

Table 7 illustrates a 2nd run, plate IP2.

TABLE 7

|   | 1 | 2 | 3 | 4 | 5 | 6 | 7 | 8 | 9 | 10 | 11 | 12 |
|---|---|---|---|---|---|---|---|---|---|----|----|----|
| A | + | + | + | + | + | + | + | + | + | +  | +  | +  |
| B | + | + | + | + | + | + | + | + | + | +  | +  | +  |
| C | − | − | − | − | − | − | − | − | − | −  | −  | −  |
| D | − | − | − | − | − | − | − | − | − | −  | −  | −  |
| E | − | − | − | − | − | − | − | − | − | −  | −  | −  |
| F | − | − | − | − | − | − | − | − | − | −  | −  | −  |
| G | + | + | + | + | + | + | + | + | + | +  | +  | +  |
| H | + | + | + | + | + | + | + | + | + | +  | +  | +  |

Table 8 illustrates a 3rd run, plate IP3.

TABLE 8

|   | 1 | 2 | 3 | 4 | 5 | 6 | 7 | 8 | 9 | 10 | 11 | 12 |
|---|---|---|---|---|---|---|---|---|---|----|----|----|
| A | + | + | + | + | + | + | + | + | + | +  | +  | +  |
| B | + | + | + | + | + | + | + | + | + | +  | +  | +  |
| C | + | + | + | + | + | + | + | + | + | +  | +  | +  |
| D | − | − | − | − | − | − | − | − | − | −  | −  | −  |
| E | − | − | − | − | − | − | − | − | − | −  | −  | −  |
| F | + | + | + | + | + | + | + | + | + | +  | +  | +  |
| G | + | + | + | + | + | + | + | + | + | +  | +  | +  |
| H | + | + | + | + | + | + | + | + | + | +  | +  | +  |

Data from the sequencing runs was analyzed and is presented in Table 9. Table 9 summarizes the performance parameters for each run, showing the number of multiplexed samples, whether the samples were identified as positive or negative for *Salmonella*, the number of active nanopore sequencing pores available in each run, the number of total reads generated for each run, and the number of false positive (FP) or false negative (FN) calls for *Salmonella* presence in each run.

Table 9 illustrates sample classification as positive or negative for *Salmonella* and Performance of Nanopore Sequencing for each of 3 successive runs on the same flow cell.

TABLE 9

| Run Id | Total samples | Index plate | Positives | Negatives | Flow cell | Active pores | Total reads | FP | FN |
|--------|---------------|-------------|-----------|-----------|-----------|--------------|-------------|----|-----|
| 1 | 96 | IP1 | 72 | 24 | New | 1485 | 1.85M | 0 | 0 |
| 2 | 96 | IP2 | 48 | 48 | Run1 washed | 1104 | 1.22M | 0 | 0 |
| 3 | 96 | IP3 | 72 | 24 | Run2 washed | 865 | 1.03M | 0 | 0 |

Surprisingly, high numbers of reads (1.03-1.85 million) were generated for each run (well above the minimum acceptable minimum threshold of 10K reads per sample). Additionally, the data from each run allowed for 100% accuracy in correctly calling the samples as positive or negative for *Salmonella* presence (e.g. zero false positive or false negative calls) and the accuracy in calls did not decline between runs.

The results in Table 9 thus demonstrate that, unexpectedly, the claimed method is capable of correctly distinguishing as many as 96 uniquely-barcoded samples stacked/multiplexed together in a single sequencing run on a nanopore flow cell, and that this can be repeated on the same nanopore flow cell as many as 3 times with no functional decline in data quality.

While preferred embodiments of the present invention have been shown and described herein, such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A nucleic acid sequencing apparatus comprising:
   (a) a nucleic acid library preparation compartment comprising two or more chambers configured to prepare a plurality of nucleic acids from a sample for a sequencing reaction, wherein said compartment is operatively connected to a nucleic acid sequencing chamber;
   (b) a nucleic acid sequencing chamber, wherein said nucleic acid sequencing chamber comprises:
      (i) one or more flow cells comprising a plurality of pores or sequencing cartridges configured for the passage of a nucleic acid strand, wherein each said one or more flow cells comprises a sample input port comprising a flow path in fluid communication with a sensing chamber outlet, wherein said sample input port is configured to be robotically opened, wherein said sample input port comprises a plug that projects a sufficient distance above the surface of the flow cell for removal by a robotic tool; and
   (c) an automated platform, wherein said automated platform is programmed to robotically move a sample from said nucleic acid library preparation compartment into said sample input port in said nucleic acid sequencing chamber.

2. The nucleic acid sequencing apparatus of claim 1, wherein said automated platform moves a second sample from said nucleic acid library preparation compartment into said nucleic acid sequencing chamber upon detecting a failure of a sequencing reaction.

3. The nucleic acid sequencing apparatus of claim 1, wherein said automated platform moves a second sample from said nucleic acid library preparation compartment into said nucleic acid sequencing chamber upon detecting a completion of a sequencing reaction.

4. The nucleic acid sequencing apparatus of claim 1, further comprising adding a barcode to a plurality of nucleic acids in said two or more chambers of (a), thereby providing a plurality of barcoded nucleic acids for said sequencing reaction.

5. The nucleic acid sequencing apparatus of claim 1, further comprising adding a plurality of mutually exclusive barcodes to a plurality of nucleic acids in said two or more chambers of (a), thereby providing a plurality of mutually exclusive barcoded nucleic acids.

6. The nucleic acid sequencing apparatus of claim 5, wherein said automated platform robotically moves two or more of said mutually exclusive barcoded nucleic acids into said nucleic acid sequencing chamber.

7. The nucleic acid sequencing apparatus of claim 5, wherein said automated platform robotically moves two or more of said mutually exclusive barcoded nucleic acids into a same flow cell of said one or more flow cells.

8. The nucleic acid sequencing apparatus of claim 5, wherein said sample is a food or an environmental sample.

9. The nucleic acid sequencing apparatus of claim 5, wherein said sample is a non-food sample.

10. The nucleic acid sequencing apparatus of claim 9, wherein said sample comprise blood, plasma, urine, tissue, faces, bone marrow, saliva or cerebrospinal fluid.

11. The nucleic acid apparatus of claim 1, wherein said automated platform is programmed to robotically open said plug.

12. The nucleic acid apparatus of claim 1, wherein said automated platform is programmed to flush at least one of said one or more flow cells.

13. The nucleic acid apparatus of claim 1, wherein said automated platform is programmed to move a liquid sample of about 0.1 µl to about 1000 µl from said nucleic acid library preparation compartment into said sample input port.

* * * * *